(12) United States Patent
Saadat et al.

(10) Patent No.: US 10,390,685 B2
(45) Date of Patent: Aug. 27, 2019

(54) OFF-AXIS VISUALIZATION SYSTEMS

(71) Applicant: Intuitive Surgical Operations, Inc., Sunnyvale, CA (US)

(72) Inventors: Vahid Saadat, Atherton, CA (US); Chris A. Rothe, San Mateo, CA (US); Ruey-Feng Peh, Singapore (SG); Edmund A. Tam, Mountain View, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

(21) Appl. No.: 14/959,109

(22) Filed: Dec. 4, 2015

(65) Prior Publication Data

US 2016/0095501 A1 Apr. 7, 2016

Related U.S. Application Data

(63) Continuation of application No. 11/961,995, filed on Dec. 20, 2007, now Pat. No. 9,226,648.
(Continued)

(51) Int. Cl.
*A61B 1/04* (2006.01)
*A61B 1/00* (2006.01)
(Continued)

(52) U.S. Cl.
CPC .......... *A61B 1/00096* (2013.01); *A61B 1/005* (2013.01); *A61B 1/0008* (2013.01);
(Continued)

(58) Field of Classification Search
USPC ................. 600/106–107, 121–125, 127, 129
See application file for complete search history.

(56) References Cited

U.S. PATENT DOCUMENTS 623,022 A 4/1899 Johnson
2,305,462 A 12/1942 Wolf
(Continued)

FOREIGN PATENT DOCUMENTS

DE 2853466 A1 6/1979
DE 10028155 A1 12/2000
(Continued)

OTHER PUBLICATIONS

Avitall B., et al., "Right-Sided Driven Atrial Fibrillation in a Sterile Pericarditis Dog Model," Pacing and Clinical Electrophysiology, 1994, vol. 17, pp. 774.
(Continued)

*Primary Examiner* — Matthew J Kasztejna
(74) *Attorney, Agent, or Firm* — Haynes and Boone, LLP

(57) ABSTRACT

A system comprises a deployment catheter defining at least one lumen and a hood projecting distally from the deployment catheter and defining an open area. The open area is in direct fluid communication with the at least one lumen. The system also comprises an elongate channel directly coupled to the hood such that the elongate channel terminates distally into the open area. The elongate channel extends proximally from an outer surface of the hood and is bounded proximally at a proximal pocket surface. The system also comprises an imaging element. The imaging element is sized to pass into the elongated channel at a distal end of the elongate channel. Proximal movement within the elongated channel is restricted by the proximal pocket surface. The system also comprises a control member extending within the elongate channel and through the proximal pocket surface for moving the imaging element through the elongate channel.

10 Claims, 43 Drawing Sheets

Related U.S. Application Data

(60) Provisional application No. 60/871,415, filed on Dec. 21, 2006, provisional application No. 60/871,424, filed on Dec. 21, 2006.

(51) Int. Cl.

| | | |
|---|---|---|
| *A61B 1/005* | (2006.01) | |
| *A61B 1/015* | (2006.01) | |
| *A61B 1/018* | (2006.01) | |
| *A61B 5/02* | (2006.01) | |
| *A61B 5/00* | (2006.01) | |
| *A61B 18/00* | (2006.01) | |

(52) U.S. Cl.
CPC ...... *A61B 1/00082* (2013.01); *A61B 1/00085* (2013.01); *A61B 1/00089* (2013.01); *A61B 1/00135* (2013.01); *A61B 1/00154* (2013.01); *A61B 1/015* (2013.01); *A61B 1/018* (2013.01); *A61B 1/04* (2013.01); *A61B 5/02007* (2013.01); *A61B 5/6882* (2013.01); *A61B 5/0031* (2013.01); *A61B 2018/00577* (2013.01)

(56) References Cited

U.S. PATENT DOCUMENTS

| | | | |
|---|---|---|---|
| 2,453,862 A | | 11/1948 | Salisbury |
| 3,559,651 A | | 2/1971 | Moss |
| 3,831,587 A | | 8/1974 | Boyd |
| 3,874,388 A | | 4/1975 | King et al. |
| 3,903,877 A | | 9/1975 | Terada |
| 4,175,545 A | | 11/1979 | Termanini |
| 4,326,529 A | | 4/1982 | Doss et al. |
| 4,403,612 A | | 9/1983 | Fogarty |
| 4,445,892 A | | 5/1984 | Hussein et al. |
| 4,470,407 A | | 9/1984 | Hussein |
| 4,517,976 A | | 5/1985 | Murakoshi et al. |
| 4,569,335 A | | 2/1986 | Tsuno |
| 4,576,146 A | | 3/1986 | Kawazoe et al. |
| 4,615,333 A | | 10/1986 | Taguchi |
| 4,619,247 A | | 10/1986 | Inoue et al. |
| 4,676,258 A | | 6/1987 | Inokuchi et al. |
| 4,681,093 A | | 7/1987 | Ono et al. |
| 4,709,698 A | | 12/1987 | Johnston et al. |
| 4,710,192 A | | 12/1987 | Liotta et al. |
| 4,727,418 A | | 2/1988 | Kato et al. |
| 4,772,260 A | | 9/1988 | Heyden |
| 4,784,133 A | | 11/1988 | Mackin |
| 4,838,246 A | | 6/1989 | Hahn et al. |
| 4,848,323 A | | 7/1989 | Marijnissen et al. |
| 4,880,015 A | | 11/1989 | Nierman |
| 4,911,148 A | | 3/1990 | Sosnowski et al. |
| 4,914,521 A | | 4/1990 | Adair |
| 4,943,290 A | | 7/1990 | Rexroth et al. |
| 4,950,285 A | | 8/1990 | Wilk |
| 4,957,484 A | | 9/1990 | Murtfeldt |
| 4,960,411 A | | 10/1990 | Buchbinder |
| 4,961,738 A | | 10/1990 | Mackin |
| 4,976,710 A | | 12/1990 | Mackin |
| 4,991,578 A | | 2/1991 | Cohen |
| 4,994,069 A | | 2/1991 | Ritchart et al. |
| 4,998,916 A | | 3/1991 | Hammerslag et al. |
| 4,998,972 A | | 3/1991 | Chin et al. |
| 5,025,778 A | * | 6/1991 | Silverstein ............ A61B 1/0008 600/104 |
| 5,047,028 A | | 9/1991 | Qian |
| 5,057,106 A | | 10/1991 | Kasevich et al. |
| 5,090,959 A | | 2/1992 | Samson et al. |
| 5,123,428 A | | 6/1992 | Schwarz |
| RE34,002 E | | 7/1992 | Adair |
| 5,156,141 A | | 10/1992 | Krebs et al. |
| 5,171,259 A | | 12/1992 | Inoue |
| 5,197,457 A | | 3/1993 | Adair |
| 5,281,238 A | | 1/1994 | Chin et al. |
| 5,282,827 A | | 2/1994 | Kensey et al. |
| 5,306,234 A | | 4/1994 | Johnson |
| 5,313,934 A | | 5/1994 | Wiita et al. |
| 5,313,943 A | | 5/1994 | Houser et al. |
| 5,330,496 A | | 7/1994 | Alferness |
| 5,334,159 A | | 8/1994 | Turkel |
| 5,334,193 A | | 8/1994 | Nardella |
| 5,336,252 A | | 8/1994 | Cohen |
| 5,339,800 A | | 8/1994 | Wiita et al. |
| 5,345,927 A | | 9/1994 | Bonutti |
| 5,348,554 A | | 9/1994 | Imran et al. |
| 5,353,792 A | | 10/1994 | Luebbers et al. |
| 5,370,647 A | | 12/1994 | Graber et al. |
| 5,373,840 A | | 12/1994 | Knighton |
| 5,375,612 A | | 12/1994 | Cottenceau et al. |
| 5,385,146 A | | 1/1995 | Goldreyer |
| 5,385,148 A | | 1/1995 | Lesh et al. |
| 5,391,182 A | | 2/1995 | Chin |
| 5,403,326 A | | 4/1995 | Harrison et al. |
| 5,405,360 A | | 4/1995 | Tovey |
| 5,405,376 A | | 4/1995 | Mulier et al. |
| 5,409,483 A | * | 4/1995 | Campbell ............ A61N 5/0601 606/13 |
| 5,411,016 A | * | 5/1995 | Kume ................ A61B 1/00082 600/114 |
| 5,413,104 A | | 5/1995 | Buijs et al. |
| 5,421,338 A | | 6/1995 | Crowley et al. |
| 5,431,649 A | | 7/1995 | Mulier et al. |
| 5,453,785 A | | 9/1995 | Lenhardt et al. |
| 5,462,521 A | | 10/1995 | Brucker et al. |
| 5,471,515 A | | 11/1995 | Fossum et al. |
| 5,498,230 A | | 3/1996 | Adair |
| 5,505,730 A | | 4/1996 | Edwards |
| 5,515,853 A | | 5/1996 | Smith et al. |
| 5,527,338 A | | 6/1996 | Purdy |
| 5,549,603 A | | 8/1996 | Feiring |
| 5,558,619 A | | 9/1996 | Kami et al. |
| 5,571,088 A | | 11/1996 | Lennox et al. |
| 5,575,756 A | | 11/1996 | Karasawa et al. |
| 5,575,810 A | | 11/1996 | Swanson et al. |
| 5,584,872 A | | 12/1996 | LaFontaine et al. |
| 5,591,119 A | | 1/1997 | Adair |
| 5,593,405 A | | 1/1997 | Osypka |
| 5,593,422 A | | 1/1997 | Muijs et al. |
| 5,593,424 A | | 1/1997 | Northrup, III |
| 5,643,282 A | | 7/1997 | Kieturakis |
| 5,653,677 A | * | 8/1997 | Okada ................ A61B 1/00016 600/112 |
| 5,662,671 A | | 9/1997 | Barbut et al. |
| 5,665,062 A | | 9/1997 | Houser |
| 5,672,153 A | | 9/1997 | Lax et al. |
| 5,676,693 A | | 10/1997 | LaFontaine |
| 5,681,308 A | | 10/1997 | Edwards et al. |
| 5,695,448 A | | 12/1997 | Kimura et al. |
| 5,697,281 A | | 12/1997 | Eggers et al. |
| 5,697,882 A | | 12/1997 | Eggers et al. |
| 5,709,224 A | | 1/1998 | Behl et al. |
| 5,713,907 A | | 2/1998 | Hogendijk et al. |
| 5,713,946 A | | 2/1998 | Ben-Haim |
| 5,716,321 A | | 2/1998 | Kerin et al. |
| 5,716,325 A | | 2/1998 | Bonutti |
| 5,722,403 A | | 3/1998 | McGee et al. |
| 5,725,523 A | | 3/1998 | Mueller |
| 5,743,851 A | * | 4/1998 | Moll ................ A61B 17/0218 600/116 |
| 5,746,747 A | | 5/1998 | McKeating |
| 5,749,846 A | | 5/1998 | Edwards et al. |
| 5,749,889 A | * | 5/1998 | Bacich ............... A61B 17/3417 600/104 |
| 5,749,890 A | | 5/1998 | Shaknovich |
| 5,754,313 A | | 5/1998 | Pelchy et al. |
| 5,766,137 A | | 6/1998 | Omata |
| 5,769,846 A | | 6/1998 | Edwards et al. |
| 5,792,045 A | | 8/1998 | Adair |
| 5,797,903 A | | 8/1998 | Swanson et al. |
| 5,823,947 A | | 10/1998 | Yoon et al. |
| 5,827,175 A | * | 10/1998 | Tanaka ..................... A61B 8/12 600/104 |
| 5,827,268 A | | 10/1998 | Laufer |
| 5,829,447 A | | 11/1998 | Stevens et al. |

(56) References Cited

U.S. PATENT DOCUMENTS

| | | | |
|---|---|---|---|
| 5,842,973 A | 12/1998 | Bullard | |
| 5,843,118 A | 12/1998 | Sepetka et al. | |
| 5,846,221 A | 12/1998 | Snoke et al. | |
| 5,848,969 A | 12/1998 | Panescu et al. | |
| 5,860,974 A | 1/1999 | Abele | |
| 5,860,991 A | 1/1999 | Klein et al. | |
| 5,865,791 A | 2/1999 | Whayne et al. | |
| 5,873,815 A | 2/1999 | Kerin et al. | |
| 5,879,366 A | 3/1999 | Shaw et al. | |
| 5,895,417 A | 4/1999 | Pomeranz et al. | |
| 5,897,487 A | 4/1999 | Ouchi | |
| 5,897,553 A | 4/1999 | Mulier et al. | |
| 5,902,328 A | 5/1999 | LaFontaine et al. | |
| 5,904,651 A | 5/1999 | Swanson et al. | |
| 5,908,445 A | 6/1999 | Whayne et al. | |
| 5,916,147 A | 6/1999 | Boury | |
| 5,925,038 A | 7/1999 | Panescu et al. | |
| 5,928,250 A | 7/1999 | Koike et al. | |
| 5,929,901 A | 7/1999 | Adair et al. | |
| 5,937,614 A * | 8/1999 | Watkins | B29C 65/745 53/374.8 |
| 5,941,845 A | 8/1999 | Tu et al. | |
| 5,944,690 A | 8/1999 | Falwell et al. | |
| 5,964,755 A | 10/1999 | Edwards | |
| 5,968,053 A | 10/1999 | Revelas | |
| 5,971,983 A | 10/1999 | Lesh | |
| 5,980,484 A * | 11/1999 | Ressemann | A61M 25/1002 604/164.13 |
| 5,985,307 A | 11/1999 | Hanson et al. | |
| 5,986,693 A | 11/1999 | Adair et al. | |
| 5,997,571 A | 12/1999 | Farr et al. | |
| 6,004,269 A | 12/1999 | Crowley et al. | |
| 6,007,521 A | 12/1999 | Bidwell et al. | |
| 6,012,457 A | 1/2000 | Lesh | |
| 6,013,024 A | 1/2000 | Mitsuda et al. | |
| 6,024,740 A | 2/2000 | Lesh et al. | |
| 6,027,501 A | 2/2000 | Goble et al. | |
| 6,036,685 A | 3/2000 | Mueller | |
| 6,043,839 A | 3/2000 | Adair et al. | |
| 6,047,218 A | 4/2000 | Whayne et al. | |
| 6,063,077 A | 5/2000 | Schaer | |
| 6,063,081 A | 5/2000 | Mulier et al. | |
| 6,068,653 A | 5/2000 | LaFontaine | |
| 6,071,279 A | 6/2000 | Whayne et al. | |
| 6,071,302 A | 6/2000 | Sinofsky et al. | |
| 6,081,740 A | 6/2000 | Gombrich et al. | |
| 6,086,528 A | 7/2000 | Adair | |
| 6,086,534 A | 7/2000 | Kesten | |
| 6,099,498 A | 8/2000 | Addis | |
| 6,099,514 A | 8/2000 | Sharkey et al. | |
| 6,102,905 A | 8/2000 | Baxter et al. | |
| 6,112,123 A | 8/2000 | Kelleher et al. | |
| 6,115,626 A | 9/2000 | Whayne et al. | |
| 6,123,703 A | 9/2000 | Tu et al. | |
| 6,123,718 A | 9/2000 | Tu et al. | |
| 6,129,724 A | 10/2000 | Fleischman et al. | |
| 6,139,508 A | 10/2000 | Simpson et al. | |
| 6,142,993 A | 11/2000 | Whayne et al. | |
| 6,152,144 A | 11/2000 | Lesh et al. | |
| 6,156,350 A | 12/2000 | Constantz | |
| 6,159,203 A | 12/2000 | Sinofsky | |
| 6,161,543 A | 12/2000 | Cox et al. | |
| 6,164,283 A | 12/2000 | Lesh | |
| 6,167,297 A | 12/2000 | Benaron | |
| 6,168,591 B1 | 1/2001 | Sinofsky | |
| 6,168,594 B1 | 1/2001 | LaFontaine et al. | |
| 6,174,307 B1 | 1/2001 | Daniel et al. | |
| 6,178,346 B1 | 1/2001 | Amundson et al. | |
| 6,190,381 B1 | 2/2001 | Olsen et al. | |
| 6,211,904 B1 | 4/2001 | Adair et al. | |
| 6,224,553 B1 | 5/2001 | Nevo | |
| 6,231,561 B1 | 5/2001 | Frazier et al. | |
| 6,234,995 B1 | 5/2001 | Peacock, III | |
| 6,235,044 B1 | 5/2001 | Root et al. | |
| 6,237,605 B1 | 5/2001 | Vaska et al. | |
| 6,238,393 B1 | 5/2001 | Mulier et al. | |
| 6,240,312 B1 | 5/2001 | Alfano et al. | |
| 6,254,598 B1 | 7/2001 | Edwards et al. | |
| 6,258,083 B1 | 7/2001 | Daniel et al. | |
| 6,263,224 B1 | 7/2001 | West | |
| 6,266,551 B1 | 7/2001 | Osadchy et al. | |
| 6,270,492 B1 | 8/2001 | Sinofsky | |
| 6,275,255 B1 | 8/2001 | Adair et al. | |
| 6,280,450 B1 | 8/2001 | McGuckin, Jr. | |
| 6,290,689 B1 | 9/2001 | Delaney et al. | |
| 6,306,081 B1 | 10/2001 | Ishikawa et al. | |
| 6,310,642 B1 | 10/2001 | Adair et al. | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,315,777 B1 | 11/2001 | Comben | |
| 6,315,778 B1 | 11/2001 | Gambale et al. | |
| 6,322,536 B1 | 11/2001 | Rosengart et al. | |
| 6,325,797 B1 | 12/2001 | Stewart et al. | |
| 6,328,727 B1 | 12/2001 | Frazier et al. | |
| 6,358,247 B1 | 3/2002 | Altman et al. | |
| 6,358,248 B1 | 3/2002 | Mulier et al. | |
| 6,375,654 B1 | 4/2002 | McIntyre | |
| 6,379,345 B1 | 4/2002 | Constantz | |
| 6,383,195 B1 | 5/2002 | Richard | |
| 6,385,476 B1 | 5/2002 | Osadchy et al. | |
| 6,387,043 B1 | 5/2002 | Yoon | |
| 6,387,071 B1 | 5/2002 | Constantz | |
| 6,394,096 B1 | 5/2002 | Constantz | |
| 6,396,873 B1 | 5/2002 | Goldstein et al. | |
| 6,398,780 B1 | 6/2002 | Farley et al. | |
| 6,401,719 B1 | 6/2002 | Farley et al. | |
| 6,409,722 B1 | 6/2002 | Hoey et al. | |
| 6,416,511 B1 | 7/2002 | Lesh et al. | |
| 6,419,669 B1 | 7/2002 | Frazier et al. | |
| 6,423,051 B1 | 7/2002 | Kaplan et al. | |
| 6,423,055 B1 | 7/2002 | Farr et al. | |
| 6,423,058 B1 | 7/2002 | Edwards et al. | |
| 6,428,536 B2 | 8/2002 | Panescu et al. | |
| 6,436,118 B1 | 8/2002 | Kayan | |
| 6,440,061 B1 | 8/2002 | Wenner et al. | |
| 6,440,119 B1 | 8/2002 | Nakada et al. | |
| 6,458,151 B1 | 10/2002 | Saltiel | |
| 6,461,327 B1 | 10/2002 | Addis et al. | |
| 6,464,697 B1 | 10/2002 | Edwards et al. | |
| 6,474,340 B1 | 11/2002 | Vaska et al. | |
| 6,475,223 B1 | 11/2002 | Werp et al. | |
| 6,478,769 B1 | 11/2002 | Parker | |
| 6,482,162 B1 | 11/2002 | Moore | |
| 6,484,727 B1 | 11/2002 | Vaska et al. | |
| 6,485,489 B2 | 11/2002 | Teirstein et al. | |
| 6,488,671 B1 | 12/2002 | Constantz et al. | |
| 6,494,902 B2 | 12/2002 | Hoey et al. | |
| 6,497,651 B1 * | 12/2002 | Kan | A61B 17/0218 600/114 |
| 6,497,705 B2 | 12/2002 | Comben | |
| 6,500,174 B1 | 12/2002 | Maguire et al. | |
| 6,502,576 B1 | 1/2003 | Lesh | |
| 6,514,249 B1 | 2/2003 | Maguire et al. | |
| 6,517,533 B1 | 2/2003 | Swaminathan | |
| 6,527,979 B2 | 3/2003 | Constantz et al. | |
| 6,532,380 B1 | 3/2003 | Close et al. | |
| 6,533,767 B2 | 3/2003 | Johansson et al. | |
| 6,537,272 B2 | 3/2003 | Christopherson et al. | |
| 6,540,733 B2 | 4/2003 | Constantz et al. | |
| 6,540,744 B2 | 4/2003 | Hassett et al. | |
| 6,544,195 B2 | 4/2003 | Wilson et al. | |
| 6,547,780 B1 | 4/2003 | Sinofsky | |
| 6,549,800 B1 | 4/2003 | Atalar et al. | |
| 6,558,375 B1 | 5/2003 | Sinofsky et al. | |
| 6,558,382 B2 | 5/2003 | Jahns et al. | |
| 6,562,020 B1 | 5/2003 | Constantz et al. | |
| 6,572,609 B1 | 6/2003 | Farr et al. | |
| 6,579,285 B2 | 6/2003 | Sinofsky | |
| 6,585,732 B2 | 7/2003 | Mulier et al. | |
| 6,587,709 B2 | 7/2003 | Solf et al. | |
| 6,593,884 B1 | 7/2003 | Gilboa et al. | |
| 6,605,055 B1 | 8/2003 | Sinofsky et al. | |
| 6,613,062 B1 | 9/2003 | Leckrone et al. | |

(56) References Cited

U.S. PATENT DOCUMENTS

| | | | |
|---|---|---|---|
| 6,622,732 B2 | 9/2003 | Constantz | |
| 6,626,855 B1 | 9/2003 | Weng et al. | |
| 6,626,899 B2 | 9/2003 | Houser et al. | |
| 6,626,900 B1 | 9/2003 | Sinofsky et al. | |
| 6,632,171 B2 * | 10/2003 | Iddan | A61B 1/00147 600/101 |
| 6,635,070 B2 | 10/2003 | Leeflang et al. | |
| 6,645,202 B1 | 11/2003 | Pless et al. | |
| 6,650,923 B1 | 11/2003 | Lesh et al. | |
| 6,658,279 B2 | 12/2003 | Swanson et al. | |
| 6,659,940 B2 | 12/2003 | Adler | |
| 6,673,090 B2 | 1/2004 | Root et al. | |
| 6,676,656 B2 | 1/2004 | Sinofsky | |
| 6,679,836 B2 | 1/2004 | Couvillon, Jr. | |
| 6,682,526 B1 | 1/2004 | Jones et al. | |
| 6,689,051 B2 * | 2/2004 | Nakada | A61B 1/00089 600/129 |
| 6,689,128 B2 | 2/2004 | Sliwa et al. | |
| 6,692,430 B2 | 2/2004 | Adler | |
| 6,701,581 B2 | 3/2004 | Senovich et al. | |
| 6,701,931 B2 | 3/2004 | Sliwa et al. | |
| 6,702,780 B1 | 3/2004 | Gilboa et al. | |
| 6,704,043 B2 | 3/2004 | Goldstein et al. | |
| 6,706,039 B2 | 3/2004 | Mulier et al. | |
| 6,712,798 B2 | 3/2004 | Constantz | |
| 6,719,747 B2 | 4/2004 | Constantz et al. | |
| 6,719,755 B2 | 4/2004 | Sliwa et al. | |
| 6,730,063 B2 | 5/2004 | Delaney et al. | |
| 6,736,810 B2 | 5/2004 | Hoey et al. | |
| 6,749,617 B1 | 6/2004 | Palasis et al. | |
| 6,751,492 B2 | 6/2004 | Ben-Haim | |
| 6,755,790 B2 | 6/2004 | Stewart et al. | |
| 6,755,811 B1 | 6/2004 | Constantz | |
| 6,764,487 B2 | 7/2004 | Mulier et al. | |
| 6,770,070 B1 | 8/2004 | Balbierz | |
| 6,771,996 B2 | 8/2004 | Bowe et al. | |
| 6,773,402 B2 | 8/2004 | Govari et al. | |
| 6,780,151 B2 | 8/2004 | Grabover et al. | |
| 6,805,128 B1 | 10/2004 | Pless et al. | |
| 6,805,129 B1 | 10/2004 | Pless et al. | |
| 6,811,562 B1 | 11/2004 | Pless | |
| 6,833,814 B2 | 12/2004 | Gilboa et al. | |
| 6,840,923 B1 | 1/2005 | Lapcevic | |
| 6,840,936 B2 | 1/2005 | Sliwa et al. | |
| 6,849,073 B2 | 2/2005 | Hoey et al. | |
| 6,858,005 B2 | 2/2005 | Ohline et al. | |
| 6,858,026 B2 | 2/2005 | Sliwa et al. | |
| 6,858,905 B2 | 2/2005 | Hsu et al. | |
| 6,863,668 B2 | 3/2005 | Gillespie et al. | |
| 6,866,651 B2 | 3/2005 | Constantz | |
| 6,887,237 B2 | 5/2005 | McGaffigan | |
| 6,892,091 B1 | 5/2005 | Ben-Haim et al. | |
| 6,896,690 B1 | 5/2005 | Lambrecht et al. | |
| 6,899,672 B2 | 5/2005 | Chin et al. | |
| 6,915,154 B1 | 7/2005 | Docherty et al. | |
| 6,916,284 B2 | 7/2005 | Moriyama | |
| 6,916,286 B2 | 7/2005 | Kazakevich | |
| 6,923,805 B1 | 8/2005 | LaFontaine et al. | |
| 6,929,010 B2 | 8/2005 | Vaska et al. | |
| 6,932,809 B2 | 8/2005 | Sinofsky | |
| 6,939,348 B2 | 9/2005 | Malecki et al. | |
| 6,942,657 B2 | 9/2005 | Sinofsky et al. | |
| 6,949,095 B2 | 9/2005 | Vaska et al. | |
| 6,953,457 B2 | 10/2005 | Farr et al. | |
| 6,955,173 B2 | 10/2005 | Lesh | |
| 6,958,069 B2 | 10/2005 | Shipp et al. | |
| 6,962,589 B2 | 11/2005 | Mulier et al. | |
| 6,971,394 B2 | 12/2005 | Sliwa et al. | |
| 6,974,464 B2 | 12/2005 | Quijano et al. | |
| 6,979,290 B2 | 12/2005 | Mourlas et al. | |
| 6,982,740 B2 | 1/2006 | Adair et al. | |
| 6,984,232 B2 | 1/2006 | Vanney et al. | |
| 6,994,094 B2 | 2/2006 | Schwartz | |
| 7,001,329 B2 * | 2/2006 | Kobayashi | A61B 1/00016 348/E7.087 |
| 7,019,610 B2 | 3/2006 | Creighton et al. | |
| 7,025,746 B2 | 4/2006 | Tal | |
| 7,030,904 B2 | 4/2006 | Adair et al. | |
| 7,041,098 B2 | 5/2006 | Farley et al. | |
| 7,042,487 B2 | 5/2006 | Nakashima | |
| 7,044,135 B2 | 5/2006 | Lesh | |
| 7,052,493 B2 | 5/2006 | Vaska et al. | |
| 7,090,683 B2 | 8/2006 | Brock et al. | |
| 7,118,566 B2 | 10/2006 | Jahns | |
| 7,156,845 B2 | 1/2007 | Mulier et al. | |
| 7,163,534 B2 | 1/2007 | Brucker et al. | |
| 7,166,537 B2 | 1/2007 | Jacobsen et al. | |
| 7,169,144 B2 | 1/2007 | Hoey et al. | |
| 7,179,224 B2 | 2/2007 | Willis | |
| 7,186,214 B2 | 3/2007 | Ness | |
| 7,207,984 B2 | 4/2007 | Farr et al. | |
| 7,217,268 B2 | 5/2007 | Eggers et al. | |
| 7,242,832 B2 | 7/2007 | Carlin et al. | |
| 7,247,155 B2 | 7/2007 | Hoey et al. | |
| 7,261,711 B2 | 8/2007 | Mulier et al. | |
| 7,263,397 B2 | 8/2007 | Hauck et al. | |
| 7,276,061 B2 | 10/2007 | Schaer et al. | |
| 7,309,328 B2 | 12/2007 | Kaplan et al. | |
| 7,322,934 B2 * | 1/2008 | Miyake | A61B 1/05 600/114 |
| 7,323,001 B2 | 1/2008 | Clubb et al. | |
| 7,416,552 B2 | 8/2008 | Paul et al. | |
| 7,435,248 B2 | 10/2008 | Taimisto et al. | |
| 7,527,625 B2 | 5/2009 | Knight et al. | |
| 7,534,204 B2 | 5/2009 | Starksen et al. | |
| 7,534,294 B1 | 5/2009 | Gaynor et al. | |
| 7,569,052 B2 | 8/2009 | Phan et al. | |
| 7,569,952 B1 | 8/2009 | Bono et al. | |
| 7,736,347 B2 | 6/2010 | Kaplan et al. | |
| 7,758,499 B2 | 7/2010 | Adler | |
| 7,860,555 B2 | 12/2010 | Saadat | |
| 7,860,556 B2 | 12/2010 | Saadat | |
| 7,918,787 B2 | 4/2011 | Saadat | |
| 7,919,610 B2 | 4/2011 | Serebriiskii et al. | |
| 7,930,016 B1 | 4/2011 | Saadat | |
| 8,050,746 B2 | 11/2011 | Saadat et al. | |
| 8,078,266 B2 | 12/2011 | Saadat et al. | |
| 8,131,350 B2 | 3/2012 | Saadat et al. | |
| 8,137,333 B2 | 3/2012 | Saadat et al. | |
| 8,221,310 B2 | 7/2012 | Saadat et al. | |
| 8,235,985 B2 | 8/2012 | Saadat et al. | |
| 8,333,012 B2 | 12/2012 | Rothe et al. | |
| 8,417,321 B2 | 4/2013 | Saadat et al. | |
| 8,419,613 B2 | 4/2013 | Saadat et al. | |
| 8,475,361 B2 * | 7/2013 | Barlow | A61B 1/0005 600/109 |
| 8,657,805 B2 | 2/2014 | Peh et al. | |
| 8,758,229 B2 | 6/2014 | Saadat et al. | |
| 8,814,845 B2 | 8/2014 | Saadat et al. | |
| 8,934,962 B2 | 1/2015 | Saadat et al. | |
| 9,055,906 B2 | 6/2015 | Saadat et al. | |
| 9,192,287 B2 | 11/2015 | Saadat et al. | |
| 9,226,648 B2 | 1/2016 | Saadat et al. | |
| 9,332,893 B2 | 5/2016 | Saadat et al. | |
| 9,510,732 B2 | 12/2016 | Miller et al. | |
| 9,526,401 B2 | 12/2016 | Saadat et al. | |
| 1,000,438 A1 | 6/2018 | Saadat et al. | |
| 1,006,454 A1 | 9/2018 | Saadat et al. | |
| 1,007,077 A1 | 9/2018 | Peh et al. | |
| 1,009,217 A1 | 10/2018 | Peh et al. | |
| 2001/0020126 A1 | 9/2001 | Swanson et al. | |
| 2001/0039416 A1 | 11/2001 | Moorman et al. | |
| 2001/0047136 A1 | 11/2001 | Domanik et al. | |
| 2001/0047184 A1 | 11/2001 | Connors | |
| 2002/0004644 A1 | 1/2002 | Koblish | |
| 2002/0026145 A1 | 2/2002 | Bagaoisan et al. | |
| 2002/0035311 A1 | 3/2002 | Ouchi | |
| 2002/0054852 A1 | 5/2002 | Cate | |
| 2002/0065455 A1 | 5/2002 | Ben-Haim et al. | |
| 2002/0077642 A1 | 6/2002 | Patel et al. | |
| 2002/0087169 A1 | 7/2002 | Brock et al. | |
| 2002/0091304 A1 | 7/2002 | Ogura et al. | |
| 2002/0138088 A1 | 9/2002 | Nash et al. | |
| 2002/0161377 A1 | 10/2002 | Rabkin et al. | |

(56) References Cited

U.S. PATENT DOCUMENTS

| | | |
|---|---|---|
| 2002/0165598 A1 | 11/2002 | Wahr et al. |
| 2002/0169377 A1 | 11/2002 | Khairkhahan et al. |
| 2003/0009085 A1 | 1/2003 | Arai et al. |
| 2003/0014010 A1 | 1/2003 | Carpenter et al. |
| 2003/0018358 A1 | 1/2003 | Saadat |
| 2003/0035156 A1 | 2/2003 | Cooper |
| 2003/0036698 A1 | 2/2003 | Kohler et al. |
| 2003/0065267 A1 | 4/2003 | Smith |
| 2003/0069593 A1 | 4/2003 | Tremulis et al. |
| 2003/0120142 A1 | 6/2003 | Dubuc et al. |
| 2003/0130572 A1 | 7/2003 | Phan et al. |
| 2003/0144657 A1 | 7/2003 | Bowe et al. |
| 2003/0171741 A1 | 9/2003 | Ziebol et al. |
| 2003/0181939 A1 | 9/2003 | Bonutti |
| 2003/0208222 A1 | 11/2003 | Zadno-Azizi |
| 2003/0212394 A1 | 11/2003 | Pearson et al. |
| 2003/0220574 A1 | 11/2003 | Markus et al. |
| 2003/0222325 A1 | 12/2003 | Jacobsen et al. |
| 2003/0236493 A1 | 12/2003 | Mauch |
| 2004/0044350 A1 | 3/2004 | Martin et al. |
| 2004/0049211 A1 | 3/2004 | Tremulis et al. |
| 2004/0054335 A1 | 3/2004 | Lesh et al. |
| 2004/0054389 A1 | 3/2004 | Osypka |
| 2004/0082833 A1 | 4/2004 | Adler et al. |
| 2004/0097792 A1 | 5/2004 | Moll et al. |
| 2004/0098031 A1 | 5/2004 | Van Der Burg et al. |
| 2004/0117032 A1 | 6/2004 | Roth |
| 2004/0133113 A1 | 7/2004 | Krishnan |
| 2004/0138707 A1 | 7/2004 | Greenhalgh |
| 2004/0147806 A1 | 7/2004 | Adler |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0158143 A1 | 8/2004 | Flaherty et al. |
| 2004/0158289 A1 | 8/2004 | Girouard et al. |
| 2004/0165766 A1 | 8/2004 | Goto |
| 2004/0167503 A1 | 8/2004 | Sinofsky |
| 2004/0181237 A1 | 9/2004 | Forde et al. |
| 2004/0199052 A1 | 10/2004 | Banik et al. |
| 2004/0210111 A1* | 10/2004 | Okada .............. A61B 1/00087 600/127 |
| 2004/0210239 A1 | 10/2004 | Nash et al. |
| 2004/0215180 A1 | 10/2004 | Starkebaum et al. |
| 2004/0220471 A1 | 11/2004 | Schwartz |
| 2004/0230131 A1 | 11/2004 | Kassab et al. |
| 2004/0248837 A1 | 12/2004 | Raz et al. |
| 2004/0249367 A1 | 12/2004 | Saadat et al. |
| 2004/0254523 A1 | 12/2004 | Fitzgerald et al. |
| 2004/0260182 A1 | 12/2004 | Zuluaga et al. |
| 2005/0015048 A1 | 1/2005 | Chiu et al. |
| 2005/0020914 A1 | 1/2005 | Amundson et al. |
| 2005/0027163 A1 | 2/2005 | Chin et al. |
| 2005/0038419 A9 | 2/2005 | Arnold et al. |
| 2005/0059862 A1 | 3/2005 | Phan |
| 2005/0059954 A1 | 3/2005 | Constantz |
| 2005/0059965 A1 | 3/2005 | Eberl et al. |
| 2005/0059984 A1 | 3/2005 | Chanduszko et al. |
| 2005/0065504 A1 | 3/2005 | Melsky et al. |
| 2005/0090818 A1 | 4/2005 | Pike et al. |
| 2005/0096502 A1 | 5/2005 | Khalili |
| 2005/0096643 A1 | 5/2005 | Brucker et al. |
| 2005/0101984 A1 | 5/2005 | Chanduszko et al. |
| 2005/0107736 A1 | 5/2005 | Landman et al. |
| 2005/0124969 A1 | 6/2005 | Fitzgerald et al. |
| 2005/0131401 A1 | 6/2005 | Malecki et al. |
| 2005/0154252 A1 | 7/2005 | Sharkey et al. |
| 2005/0159702 A1 | 7/2005 | Sekiguchi et al. |
| 2005/0165272 A1* | 7/2005 | Okada .............. A61B 1/0008 600/114 |
| 2005/0165279 A1 | 7/2005 | Adler et al. |
| 2005/0165391 A1 | 7/2005 | Maguire et al. |
| 2005/0165466 A1 | 7/2005 | Morris et al. |
| 2005/0197530 A1 | 9/2005 | Wallace et al. |
| 2005/0197623 A1 | 9/2005 | Leeflang et al. |
| 2005/0215895 A1 | 9/2005 | Popp et al. |
| 2005/0222554 A1 | 10/2005 | Wallace et al. |
| 2005/0222557 A1 | 10/2005 | Baxter et al. |
| 2005/0222558 A1 | 10/2005 | Baxter et al. |
| 2005/0228452 A1 | 10/2005 | Mourlas et al. |
| 2005/0234436 A1 | 10/2005 | Baxter et al. |
| 2005/0234437 A1 | 10/2005 | Baxter et al. |
| 2005/0267328 A1 | 12/2005 | Blumzvig et al. |
| 2006/0009715 A1 | 1/2006 | Khairkhahan et al. |
| 2006/0009737 A1 | 1/2006 | Whiting et al. |
| 2006/0015096 A1 | 1/2006 | Hauck et al. |
| 2006/0022234 A1 | 2/2006 | Adair et al. |
| 2006/0025651 A1 | 2/2006 | Adler et al. |
| 2006/0025787 A1 | 2/2006 | Morales et al. |
| 2006/0069303 A1 | 3/2006 | Couvillon, Jr. |
| 2006/0074398 A1 | 4/2006 | Whiting et al. |
| 2006/0084839 A1* | 4/2006 | Mourlas .............. A61B 1/00082 600/116 |
| 2006/0084945 A1 | 4/2006 | Moll et al. |
| 2006/0089637 A1 | 4/2006 | Werneth et al. |
| 2006/0111614 A1 | 5/2006 | Saadat et al. |
| 2006/0122587 A1 | 6/2006 | Sharareh |
| 2006/0146172 A1 | 7/2006 | Jacobsen et al. |
| 2006/0149129 A1* | 7/2006 | Watts .................. A61B 1/00135 600/113 |
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kalser et al. |
| 2006/0183992 A1 | 8/2006 | Kawashima |
| 2006/0217755 A1 | 9/2006 | Eversull et al. |
| 2006/0224167 A1 | 10/2006 | Weisenburgh et al. |
| 2006/0253113 A1 | 11/2006 | Arnold et al. |
| 2006/0258909 A1 | 11/2006 | Saadat et al. |
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043413 A1 | 2/2007 | Eversull et al. |
| 2007/0049923 A1 | 3/2007 | Jahns |
| 2007/0055142 A1 | 3/2007 | Webler |
| 2007/0078451 A1 | 4/2007 | Arnold et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100324 A1 | 5/2007 | Tempel et al. |
| 2007/0106146 A1 | 5/2007 | Altmann et al. |
| 2007/0106214 A1 | 5/2007 | Gray et al. |
| 2007/0106287 A1 | 5/2007 | O'Sullivan |
| 2007/0135826 A1 | 6/2007 | Zaver et al. |
| 2007/0167801 A1 | 7/2007 | Webler et al. |
| 2007/0239010 A1 | 10/2007 | Johnson |
| 2007/0265609 A1 | 11/2007 | Thapliyal et al. |
| 2007/0265610 A1 | 11/2007 | Thapliyal et al. |
| 2007/0270639 A1 | 11/2007 | Long |
| 2007/0270686 A1 | 11/2007 | Ritter et al. |
| 2007/0282371 A1 | 12/2007 | Lee et al. |
| 2007/0293724 A1 | 12/2007 | Saadat et al. |
| 2008/0009747 A1 | 1/2008 | Saadat et al. |
| 2008/0009859 A1 | 1/2008 | Auth et al. |
| 2008/0015563 A1 | 1/2008 | Hoey et al. |
| 2008/0015569 A1 | 1/2008 | Saadat et al. |
| 2008/0027464 A1 | 1/2008 | Moll et al. |
| 2008/0033241 A1 | 2/2008 | Peh et al. |
| 2008/0057106 A1 | 3/2008 | Erickson et al. |
| 2008/0058590 A1 | 3/2008 | Saadat et al. |
| 2008/0058650 A1 | 3/2008 | Saadat et al. |
| 2008/0058836 A1 | 3/2008 | Moll et al. |
| 2008/0097476 A1 | 4/2008 | Peh et al. |
| 2008/0183081 A1 | 7/2008 | Lys et al. |
| 2008/0214889 A1 | 9/2008 | Saadat et al. |
| 2008/0228032 A1 | 9/2008 | Starksen et al. |
| 2008/0275300 A1 | 11/2008 | Rothe et al. |
| 2008/0287790 A1 | 11/2008 | Li |
| 2008/0287805 A1 | 11/2008 | Li |
| 2009/0030276 A1 | 1/2009 | Saadat et al. |
| 2009/0030412 A1 | 1/2009 | Willis et al. |
| 2009/0048480 A1 | 2/2009 | Klenk et al. |
| 2009/0062790 A1 | 3/2009 | Malchano et al. |

(56) References Cited

U.S. PATENT DOCUMENTS

| | | |
|---|---|---|
| 2009/0076489 A1 | 3/2009 | Welches et al. |
| 2009/0082623 A1 | 3/2009 | Rothe et al. |
| 2009/0125022 A1 | 5/2009 | Saadat et al. |
| 2009/0143640 A1 | 6/2009 | Saadat et al. |
| 2009/0187074 A1 | 7/2009 | Saadat et al. |
| 2009/0203962 A1 | 8/2009 | Miller et al. |
| 2009/0221871 A1 | 9/2009 | Peh et al. |
| 2009/0227999 A1 | 9/2009 | Willis et al. |
| 2009/0264727 A1 | 10/2009 | Markowitz et al. |
| 2009/0267773 A1 | 10/2009 | Markowitz et al. |
| 2009/0299363 A1 | 12/2009 | Saadat et al. |
| 2009/0326572 A1 | 12/2009 | Peh et al. |
| 2010/0004506 A1 | 1/2010 | Saadat |
| 2010/0004633 A1 | 1/2010 | Rothe et al. |
| 2010/0004661 A1 | 1/2010 | Verin et al. |
| 2010/0010311 A1 | 1/2010 | Miller et al. |
| 2010/0130836 A1 | 5/2010 | Malchano et al. |
| 2011/0060227 A1 | 3/2011 | Saadat |
| 2011/0060298 A1 | 3/2011 | Saadat |
| 2011/0144576 A1 | 6/2011 | Rothe et al. |
| 2012/0016221 A1 | 1/2012 | Saadat et al. |
| 2012/0059366 A1 | 3/2012 | Drews et al. |
| 2012/0150046 A1 | 6/2012 | Watson et al. |
| 2013/0023731 A1 | 1/2013 | Saadat et al. |
| 2013/0131448 A1 | 5/2013 | Saadat et al. |
| 2014/0012074 A1 | 1/2014 | Vazales et al. |
| 2014/0114129 A1 | 4/2014 | Peh et al. |
| 2014/0350412 A1 | 11/2014 | Saadat et al. |
| 2015/0094577 A1 | 4/2015 | Saadat et al. |
| 2015/0190036 A1 | 7/2015 | Saadat |
| 2015/0250382 A1 | 9/2015 | Saadat et al. |
| 2016/0038005 A1 | 2/2016 | Saadat et al. |
| 2016/0095501 A1 | 4/2016 | Saadat et al. |
| 2016/0227989 A1 | 8/2016 | Saadat et al. |
| 2017/0071460 A1 | 3/2017 | Miller et al. |
| 2018/0228350 A1 | 8/2018 | Saadat et al. |

FOREIGN PATENT DOCUMENTS

| | | |
|---|---|---|
| EP | 0283661 A2 | 9/1988 |
| EP | 0301288 A1 | 2/1989 |
| EP | 0842673 A | 5/1998 |
| JP | S5993413 A | 5/1984 |
| JP | S59181315 A | 10/1984 |
| JP | H01221133 A | 9/1989 |
| JP | H03284265 A | 12/1991 |
| JP | H05103746 A | 4/1993 |
| JP | H06507809 A | 9/1994 |
| JP | H0951897 A | 2/1997 |
| JP | H11299725 A | 11/1999 |
| JP | 2001504363 A | 4/2001 |
| JP | 2001258822 A | 9/2001 |
| WO | WO-9221292 A2 | 12/1992 |
| WO | WO-9407413 A1 | 4/1994 |
| WO | WO-9503843 A1 | 2/1995 |
| WO | WO-9740880 A1 | 11/1997 |
| WO | WO-9818388 A1 | 5/1998 |
| WO | WO-0024310 A | 5/2000 |
| WO | WO-0149356 A | 7/2001 |
| WO | WO-0172368 A | 10/2001 |
| WO | WO-0230310 A1 | 4/2002 |
| WO | WO-03037416 A1 | 5/2003 |
| WO | WO-03039350 A2 | 5/2003 |
| WO | WO-03053491 A2 | 7/2003 |
| WO | WO-03073942 A2 | 9/2003 |
| WO | WO-03101287 A2 | 12/2003 |
| WO | WO-2004043272 A1 | 5/2004 |
| WO | WO-2004080508 A2 | 9/2004 |
| WO | WO-2005070330 A1 | 8/2005 |
| WO | WO-2005077435 A1 | 8/2005 |
| WO | WO-2005081202 A1 | 9/2005 |
| WO | WO-2006017517 A2 | 2/2006 |
| WO | WO-2006024015 A1 | 3/2006 |
| WO | WO-2006083794 A2 | 8/2006 |
| WO | WO-2006091597 A1 | 8/2006 |
| WO | WO-2006126979 A2 | 11/2006 |
| WO | WO-2007067323 A2 | 6/2007 |
| WO | WO-2007079268 A2 | 7/2007 |
| WO | WO-2007133845 A2 | 11/2007 |
| WO | WO-2007134258 A2 | 11/2007 |
| WO | WO-2008015625 A2 | 2/2008 |
| WO | WO-2008021994 A2 | 2/2008 |
| WO | WO-2008021997 A2 | 2/2008 |
| WO | WO-2008021998 A2 | 2/2008 |
| WO | WO-2008024261 A2 | 2/2008 |
| WO | WO-2008079828 A2 | 7/2008 |
| WO | WO-2009112262 A2 | 9/2009 |

OTHER PUBLICATIONS

Avitall, et al. "A Catheter System to Ablate Atrial Fibrillation in a Sterile Pericarditis Dog Model," Pacing and Clinical Electrophysiology, 1994, vol. 17, pp. 774.

Avitall, "Vagally Mediated Atrial Fibrillation in a Dog Model can be Ablated by Placing Linear Radiofrequency Lesions at the Junction of the Right Atrial Appendage and the Superior Vena Cava." Pacing and Clinical Electrophysiology, 1995, vol. 18, pp. 857.

Baker B.M., et al., "Nonpharmacologic Approaches to the Treatment of Atrial Fibrillation and Atrial Flutter," Journal of Cardiovascular Electrophysiology, 1995, vol. 6, (10 Pt 2), pp. 972-978.

Bhakta D., et al., "Principles of Electroanatomic Mapping," Indian Pacing and Electrophysiology Journal, 2008, vol. 8(1), pp. 32-50.

Bidoggia H., et al., "Transseptal Left Heart Catheterization: Usefulness of the Intracavitary Electrocardiogram in the Localization of the Fossa Ovalis," Cathet Cardiovasc Diagn, 1991, vol. 24 (3), pp. 221-225, PMID: 1764747 [online], [retrieved Feb. 15, 2010]. Retrieved from the Internet: &It;URL: http://www.ncbi.nlm.nih.gov/sites/entrez >.

Bredikis J.J., et al., "Surgery of Tachyarrhythmia: Intracardiac Closed Heart Cryoablation," Pacing and Clinical Electrophysiology, 1990, vol. 13 (Part 2), pp. 1980-1984.

Communication from the Examining Division for Application No. EP06734083.6 dated Nov. 12, 2010, 3 pages.

Communication from the Examining Division for Application No. EP06734083.6 dated Oct. 23, 2009, 1 page.

Communication from the Examining Division for Application No. EP08746822.9 dated Jul. 13, 2010, 1 page.

U.S. Appl. No. 61/286,283, filed Dec. 14, 2009.

U.S. Appl. No. 61/297,462, filed Jan. 22, 2010.

Cox J.L., "Cardiac Surgery for Arrhythmias," Journal of Cardiovascular Electrophysiology, 2004, vol. 15, pp. 250-262.

Cox J.L., et al., "Five-Year Experience With the Maze Procedure for Atrial Fibrillation," The Annals of Thoracic Surgery, 1993, vol. 56, pp. 814-824.

Cox J.L., et al., "Modification of the Maze Procedure for Atrial Flutter and Atrial Fibrillation," The Journal of Thoracic and Cardiovascular Surgery, 1995, vol. 110, pp. 473-484.

Cox J.L., "The Status of Surgery for Cardiac Arrhythmias," Circulation, 1985, vol. 71, pp. 413-417.

Cox J.L., "The Surgical Treatment of Atrial Fibrillation," The Journal of Thoracic and Cardiovascular Surgery, 1991, vol. 101, pp. 584-592.

Elvan A., et al., "Radiofrequency Catheter Ablation of the Atria Reduces Inducibility and Duration of Atrial Fibrillation in Dogs," Circulation, vol. 91, 1995, pp. 2235-2244 [online], [retrieved Feb. 4, 2013]. Retrieved from the Internet: URL: http://circ.ahajournals.org/cgi/content/full/91/8/2235.

Elvan A., et al., "Radiofrequency Catheter Ablation (RFCA) of the Atria Effectively Abolishes Pacing Induced Chronic Atrial Fibrillation," Pacing and Clinical Electrophysiology, 1995, vol. 18, pp. 856.

Elvan, et al., "Replication of the 'Maze' Procedure by Radiofrequency Catheter Ablation Reduces the Ability to Induce Atrial Fibrillation," Pacing and Clinical Electrophysiology, 1994, vol. 17, pp. 774.

European Search Report for Application No. EP07799466.3 dated Nov. 16, 2010, 9 pages.

European Search Report for Application No. EP08746822.9 dated Mar. 29, 2010, 7 Pages.

(56) References Cited

OTHER PUBLICATIONS

Examination Communication for Application No. EP06734083.6 dated May 18, 2010, 3 Pages.
Extended European Search Report for Application No. EP06734083.6 dated Jul. 1, 2009, 6 pages.
Extended European search report for Application No. EP20070758716 dated Feb. 28, 2011, 8 Pages.
Extended European search report for Application No. EP20070799466 dated Nov. 18, 2010, 9 Pages.
Fieguth H.G., et al., "Inhibition of Atrial Fibrillation by Pulmonary Vein Isolation and Auricular Resection—Experimental Study in a Sheep Model," The European Journal of Cardio-Thoracic Surgery, 1997, vol. 11, pp. 714-721.
Final Office Action dated Mar. 1, 2010 for U.S. Appl. No. 12/117,655, filed May 8, 2008.
Final Office Action dated Jun. 2, 2011 for U.S. Appl. No. 12/117,655, filed May 8, 2008.
Final Office Action dated Oct. 5, 2010 for U.S. Appl. No. 11/810,850, filed Jun. 7, 2007.
Final Office Action dated May 12, 2011 for U.S. Appl. No. 11/775,771, filed Jul. 10, 2007.
Final Office Action dated Sep. 16, 2010 for U.S. Appl. No. 11/828,267, filed Jul. 25, 2007.
Hoey M.F., et al., "Intramural Ablation Using Radiofrequency Energy via Screw-Tip Catheter and Saline Electrode," Pacing and Clinical Electrophysiology, 1995, vol. 18, Part II, 487.
Huang, "Increase in the Lesion Size and Decrease in the Impedance Rise with a Saline Infusion Electrode Catheter for Radiofrequency," Circulation, 1989, vol. 80 (4), II-324.
International Search Report and Written Opinion for Application No. PCT/US2007/073184, dated Aug. 12, 2012, 7 pages.
International Search Report for Application No. PCT/US2006/003288, dated Aug. 9, 2007, 1 page.
International Search Report for Application No. PCT/US2007/064195, dated Dec. 7, 2007, 1 page.
International Search Report for Application No. PCT/US2007/071226, dated Sep. 4, 2008, 1 page.
International Search Report for Application No. PCT/US2007/077429, dated Apr. 7, 2008, 1 page.
Moser K.M., et al., "Angioscopic Visualization of Pulmonary Emboli," Chest. 1980, vol. 77 (2), pp. 198-201.
Nakamura F., et al., "Percutaneous Intracardiac Surgery With Cardioscopic Guidance," SPIE, 1992, vol. 1642, pp. 214-216.
Non-Final Office Action dated Jun. 7, 2011 for U.S. Appl. No. 12/323,281, filed Nov. 25, 2008.
Non-Final Office Action dated Aug. 8, 2011 for U.S. Appl. No. 12/464,800, filed May 12, 2009.
Non-Final Office Action dated Jun. 8, 2009 for U.S. Appl. No. 12/117,655, filed May 8, 2008.
Non-Final Office Action dated May 9, 2011 for U.S. Appl. No. 11/961,950, filed Dec. 20, 2007.
Non-Final Office Action dated May 9, 2011 for U.S. Appl. No. 11/961,995, filed Dec. 20, 2007.
Non-Final Office Action dated May 9, 2011 for U.S. Appl. No. 11/962,029, filed Dec. 20, 2007.
Non-Final Office Action dated Jun. 10, 2010 for U.S. Appl. No. 11/560,742, filed Nov. 16, 2006.
Non-Final Office Action dated Apr. 11, 2011 for U.S. Appl. No. 11/763,399, filed Jun. 14, 2007.
Non-Final Office Action dated Mar. 11, 2011 for U.S. Appl. No. 11/848,202, filed Aug. 30, 2007.
Non-Final Office Action dated May 11, 2011 for U.S. Appl. No. 11/828,267, filed Jul. 25, 2007.
Non-Final Office Action dated Apr. 12, 2011 for U.S. Appl. No. 12/499,011, filed Jul. 7, 2009.
Non-Final Office Action dated Jan. 14, 2010 for U.S. Appl. No. 11/828,267, filed Jul. 25, 2007.
Non-Final Office Action dated Dec. 16, 2010 for U.S. Appl. No. 12/117,655, filed May 8, 2008.
Non-Final Office Action dated Mar. 16, 2010 for U.S. Appl. No. 11/810,850, filed Jun. 7, 2007.
Non-Final Office Action dated Feb. 18, 2011 for U.S. Appl. No. 12/947,198, filed Nov. 16, 2010.
Non-Final Office Action dated Feb. 18, 2011 for U.S. Appl. No. 12/947,246, filed Nov. 16, 2006.
Non-Final Office Action dated May 20, 2011 for U.S. Appl. No. 11/775,819, filed Jul. 10, 2007.
Non-Final Office Action dated May 20, 2011 for U.S. Appl. No. 11/877,366, filed Oct. 23, 2007.
Non-Final Office Action dated Jul. 21, 2010 for U.S. Appl. No. 11/687,597, filed Mar. 16, 2007.
Non-Final Office Action dated Apr. 22, 2011 for U.S. Appl. No. 12/367,019, filed Feb. 6, 2009.
Non-Final Office Action dated May 23, 2011 for U.S. Appl. No. 11/775,837, filed Jul. 10, 2007.
Non-Final Office Action dated Nov. 24, 2010 for U.S. Appl. No. 11/848,429, filed Aug. 31, 2007.
Non-Final Office Action dated Nov. 24, 2010 for U.S. Appl. No. 12/464,800, filed May 12, 2009.
Non-Final Office Action dated Apr. 25, 2011 for U.S. Appl. No. 11/959,158, filed Dec. 18, 2007.
Non-Final Office Action dated Feb. 25, 2010 for U.S. Appl. No. 11/259,498, filed Oct. 25, 2005.
Non-Final Office Action dated Feb. 25, 2011 for U.S. Appl. No. 11/848,207, filed Aug. 30, 2007.
Non-Final Office Action dated Apr. 26, 2011 for U.S. Appl. No. 11/848,532, filed Aug. 31, 2007.
Non-Final Office Action dated Apr. 27, 2011 for U.S. Appl. No. 11/828,281, filed Jul. 25, 2007.
Non-Final Office Action dated Apr. 27, 2010 for U.S. Appl. No. 11/775,771, filed Jul. 10, 2007.
Non-Final Office Action dated Dec. 27, 2010 for U.S. Appl. No. 12/026,455, filed Feb. 5, 2008.
Notice of Allowance dated Feb. 3, 2011 for U.S. Appl. No. 11/560,732, filed Nov. 16, 2006.
Notice of Allowance dated Jun. 13, 2011 for Japanese Application No. 2007-554156 filed Jan. 30, 2006.
Notice of Allowance dated Nov. 15, 2010 for U.S. Appl. No. 11/259,498, filed Oct. 25, 2005.
Notice of Allowance dated Nov. 15, 2010 for U.S. Appl. No. 11/560,742, filed Nov. 16, 2006.
Notice of Allowance dated Feb. 24, 2011 for U.S. Appl. No. 11/560,732, filed Mar. 16, 2007.
Notice of Allowance dated Feb. 24, 2011 for U.S. Appl. No. 11/687,597, filed Mar. 16, 2007.
Office Action dated Feb. 15, 2011 for Japanese Application No. 2007-554156 filed Jan. 30, 2006.
Office Action dated Apr. 27, 2011 for Japanese Application No. 2009-500630 filed Mar. 16, 2007.
Pappone C., et al., "Circumferential Radiofrequency Ablation of Pulmonary Vein Ostia," Circulation, 2000, vol. 102, pp. 2619-2628.
Sethi K.K., et al., "Transseptal catheterization for the electrophysiologist: modification with a 'view'," Journal of Interventional Cardiac Electrophysiology, 2001, vol. 5 (1), pp. 97-99.
Supplemental European Search Report for Application No. EP07758716 dated Feb. 28, 2011, 8 Pages.
Supplementary European search report for Application No. EP07812146.4 dated Nov. 18, 2010, 8 Pages.
Supplementary European Search Report for Application No. EP07841754, dated Jun. 30, 2010, 6 pages.
Thiagalingam A., et al., "Cooled Needle Catheter Ablation Creates Deeper and Wider Lesions than Irrigated Tip Catheter Ablation," Journal of Cardiovascular Electrophysiology, 2005, vol. 16 (5), pp. 1-8.
Uchida Y., "Developmental History of Cardioscopes", in: Coronary Angioscopy. Chapter 19, Futura Publishing Company, Inc., 2001, pp. 187-197.
Willkampf F.H., et al., "Radiofrequency Ablation with a Cooled Porous Electrode Catheter," JACC, Abstract, 1988, vol. 11 (2), pp. 17A.
Written Opinion for Application No. PCT/US2006/003288, dated Aug. 9, 2007, 6 pages.

(56) References Cited

OTHER PUBLICATIONS

Written Opinion for Application No. PCT/US2007/064195, dated Dec. 7, 2007, 5 pages.
Written Opinion for Application No. PCT/US2007/071226, dated Sep. 4, 2008, 4 page.
Written Opinion for Application No. PCT/US2007/077429, dated Apr. 7, 2008, 5 pages.
Tse HF., et al., "Angiogenesis in Ischaemic Myocardium by Intramyocardial Autologous Bone Marrow Mononuclear Cell Implantation," LANCET, 2003, vol. 361, pp. 47-49.

\* cited by examiner

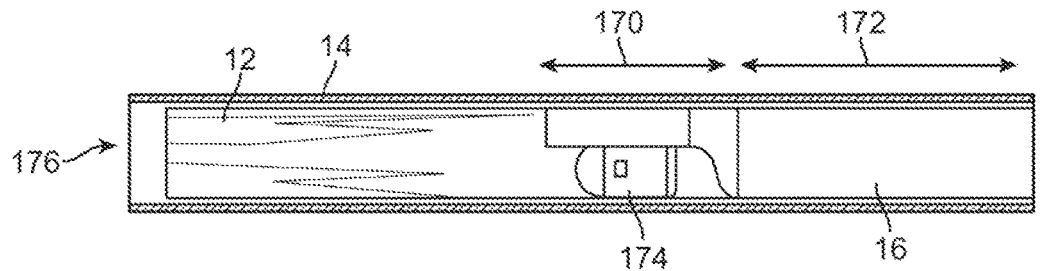
FIG. 11A
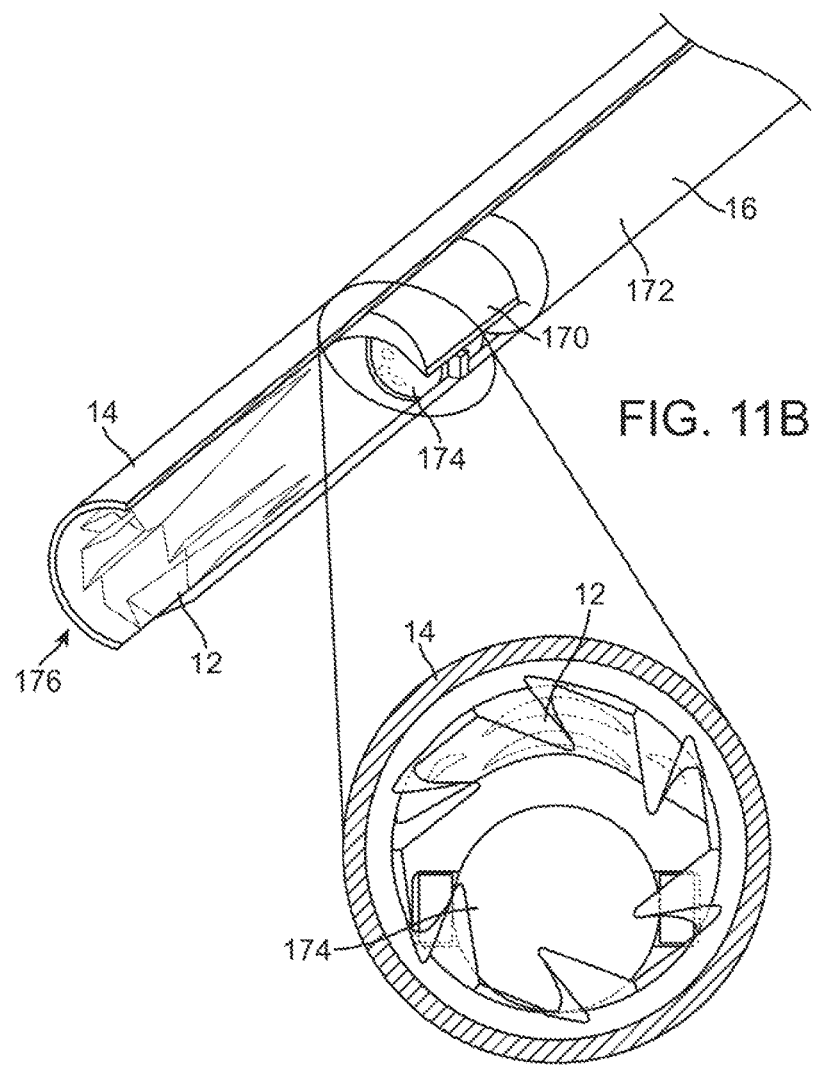
FIG. 11B
FIG. 11C

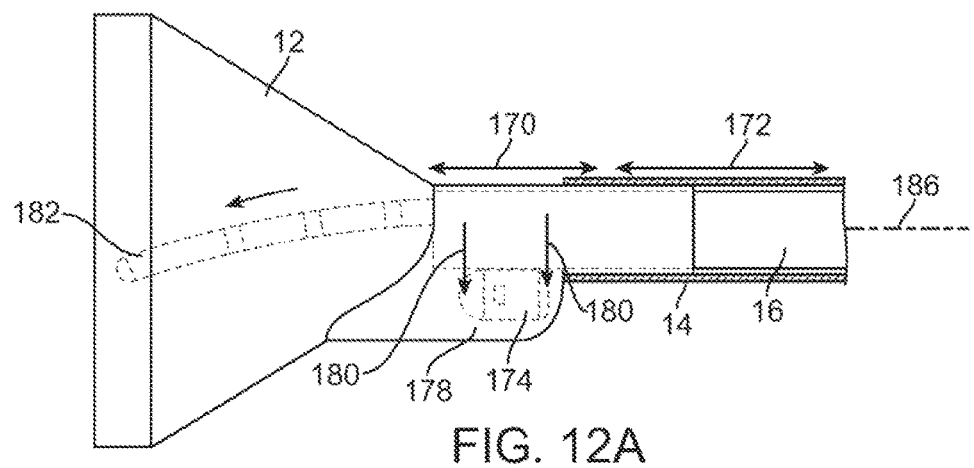
FIG. 12A
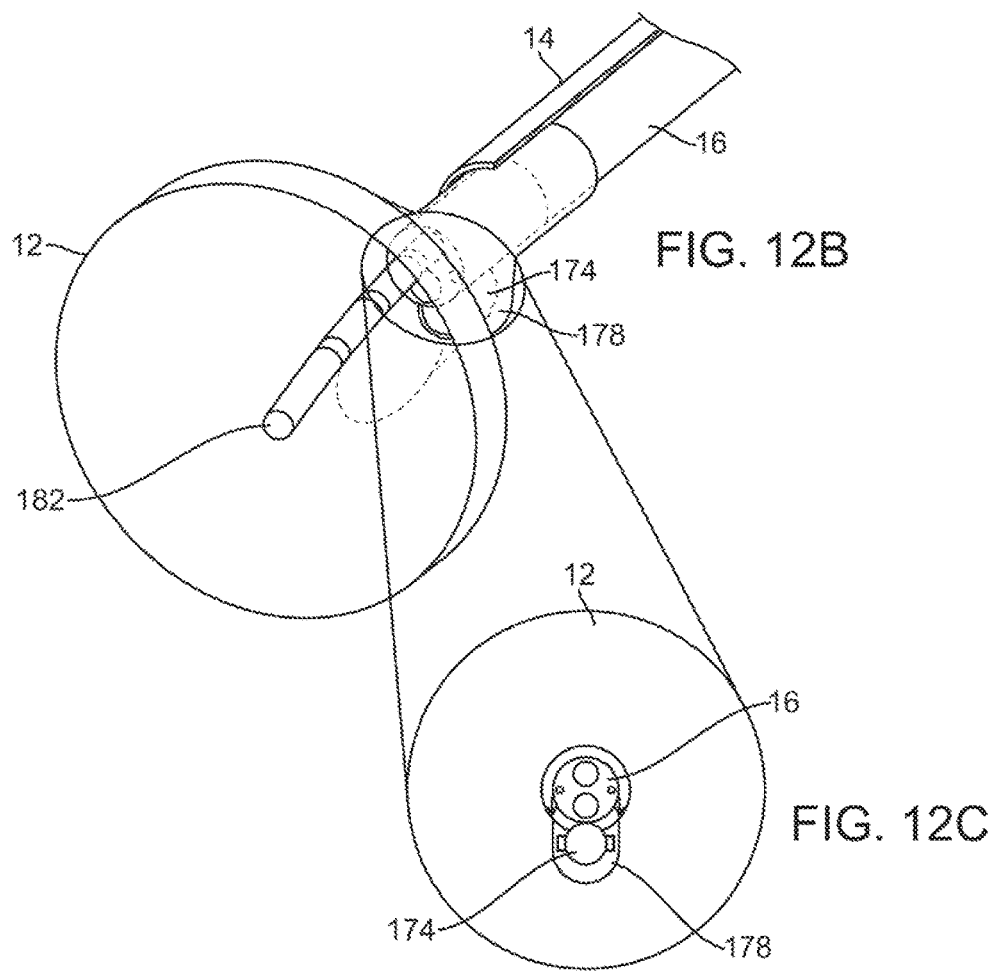
FIG. 12B
FIG. 12C

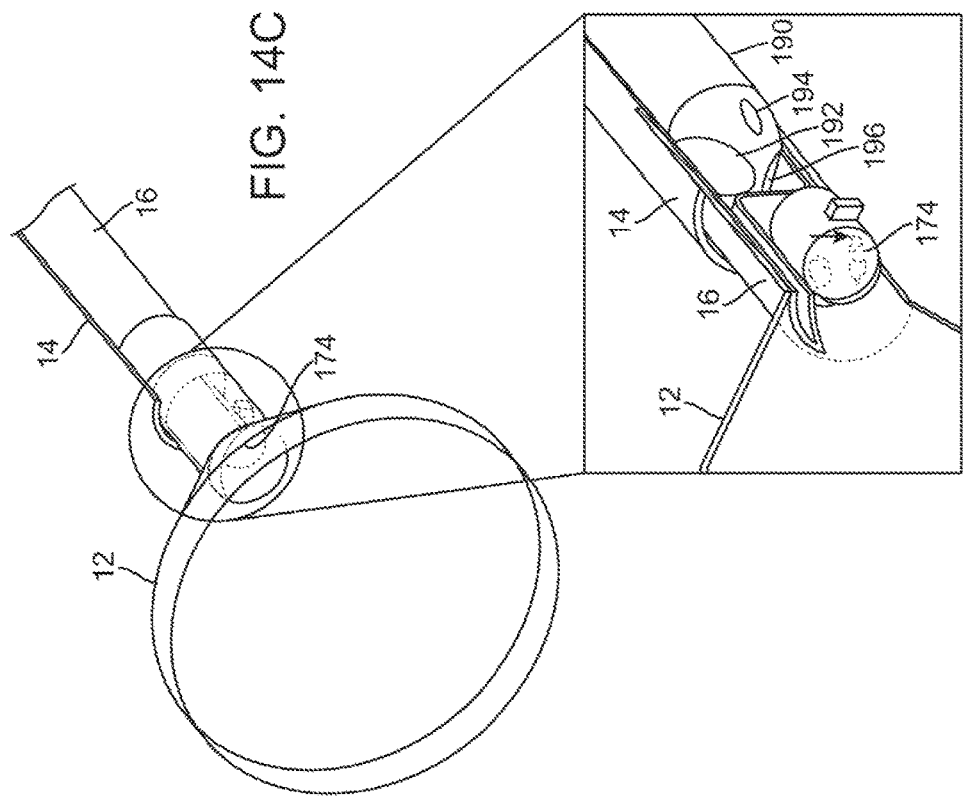
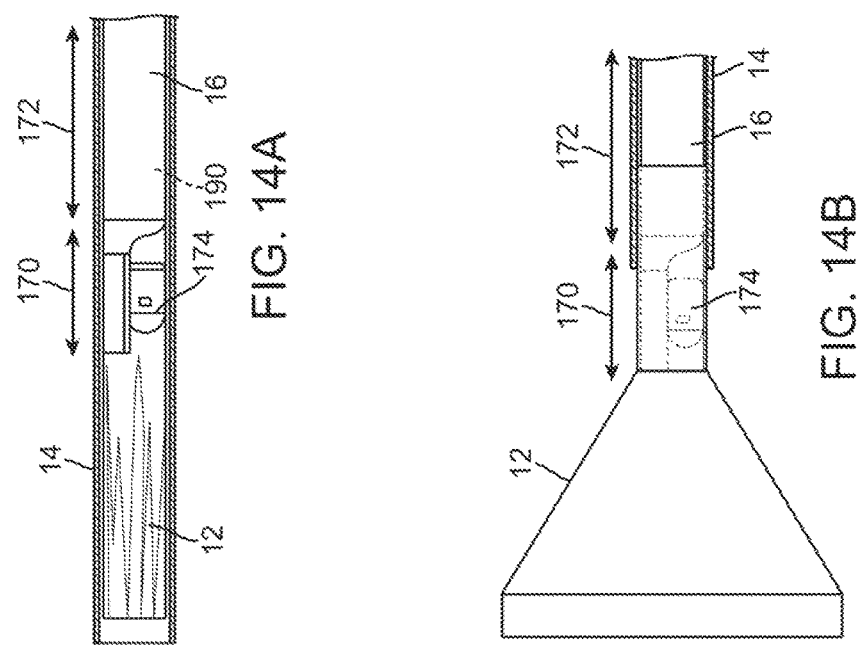

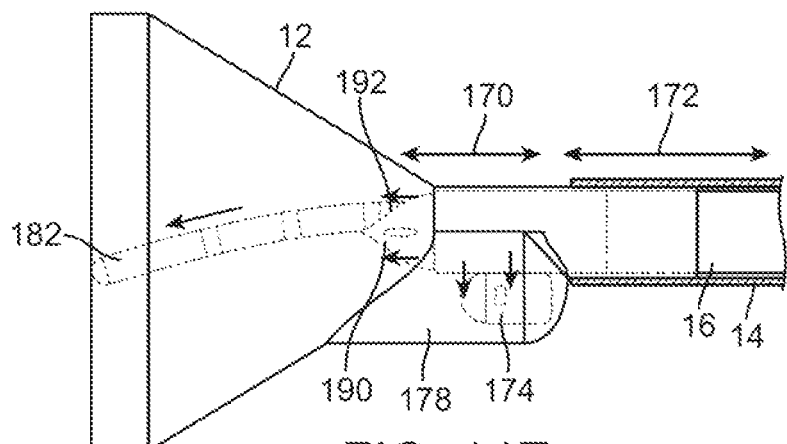
FIG. 14E
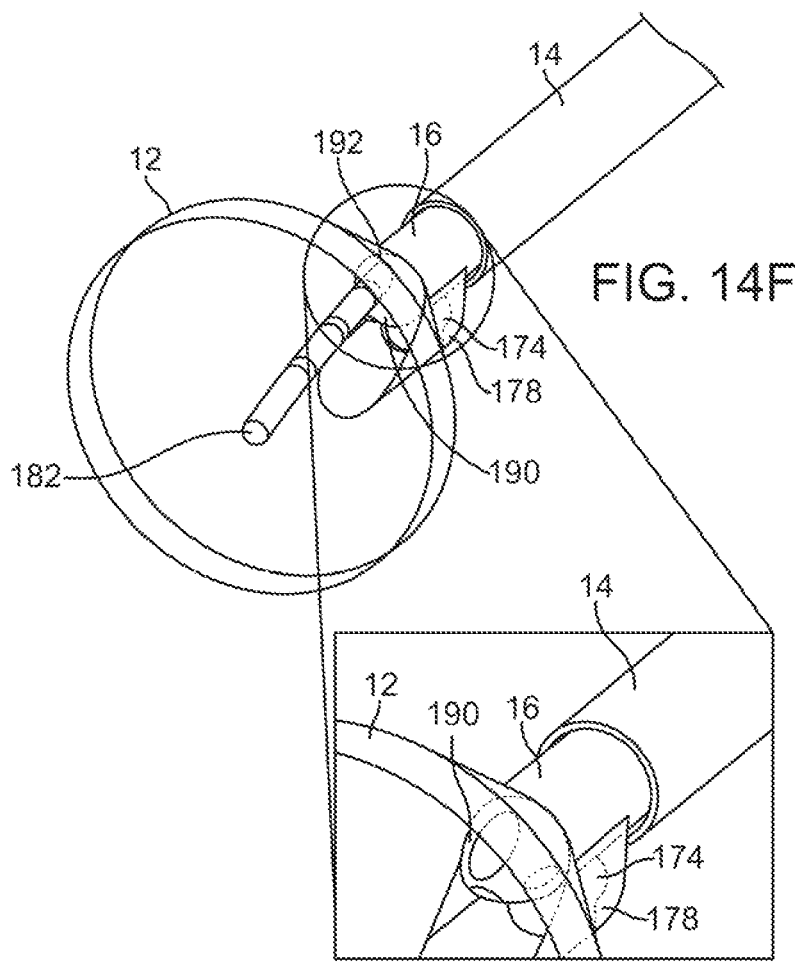
FIG. 14F
FIG. 14G

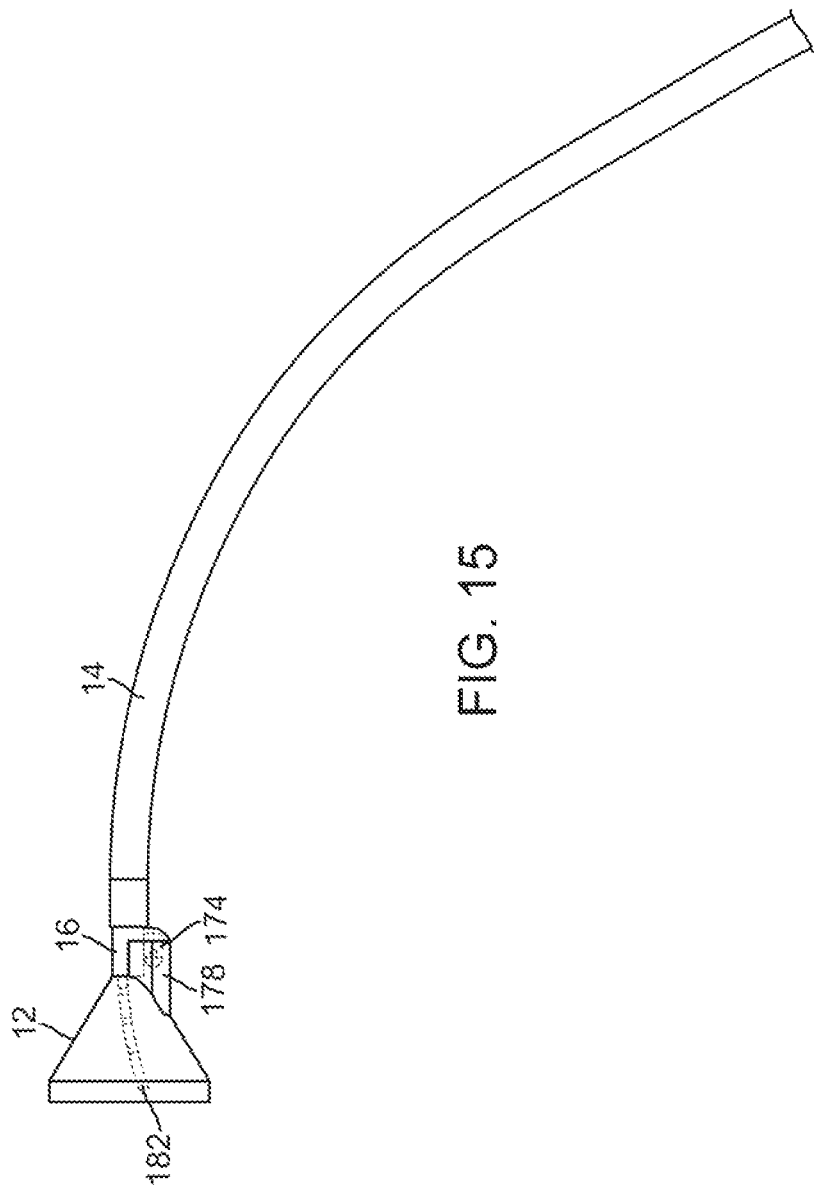

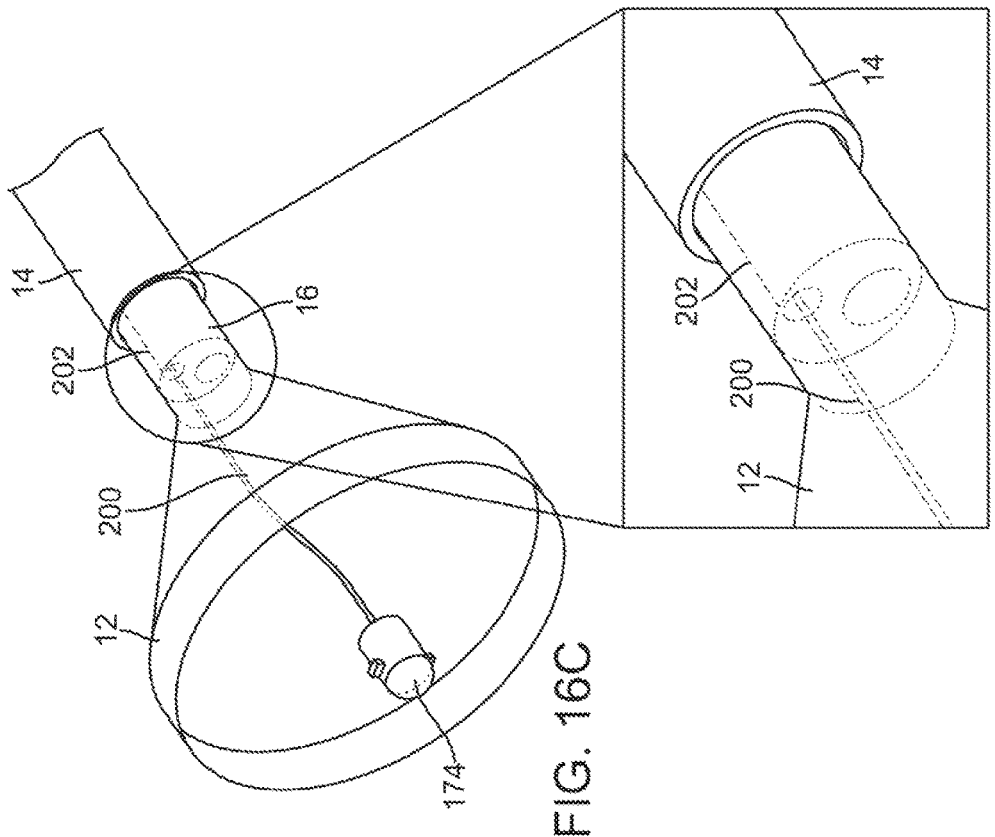
FIG. 16D
FIG. 16C
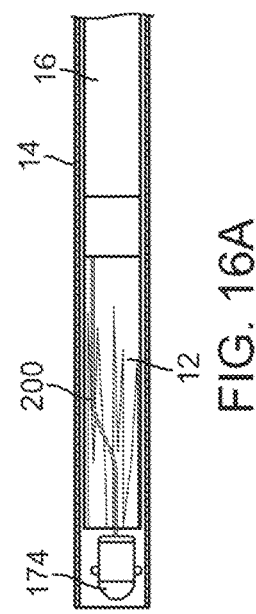
FIG. 16A
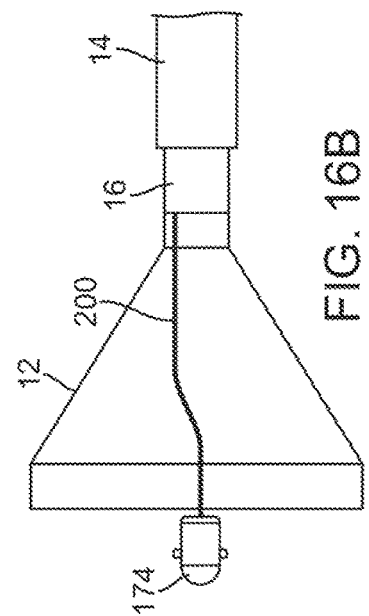
FIG. 16B

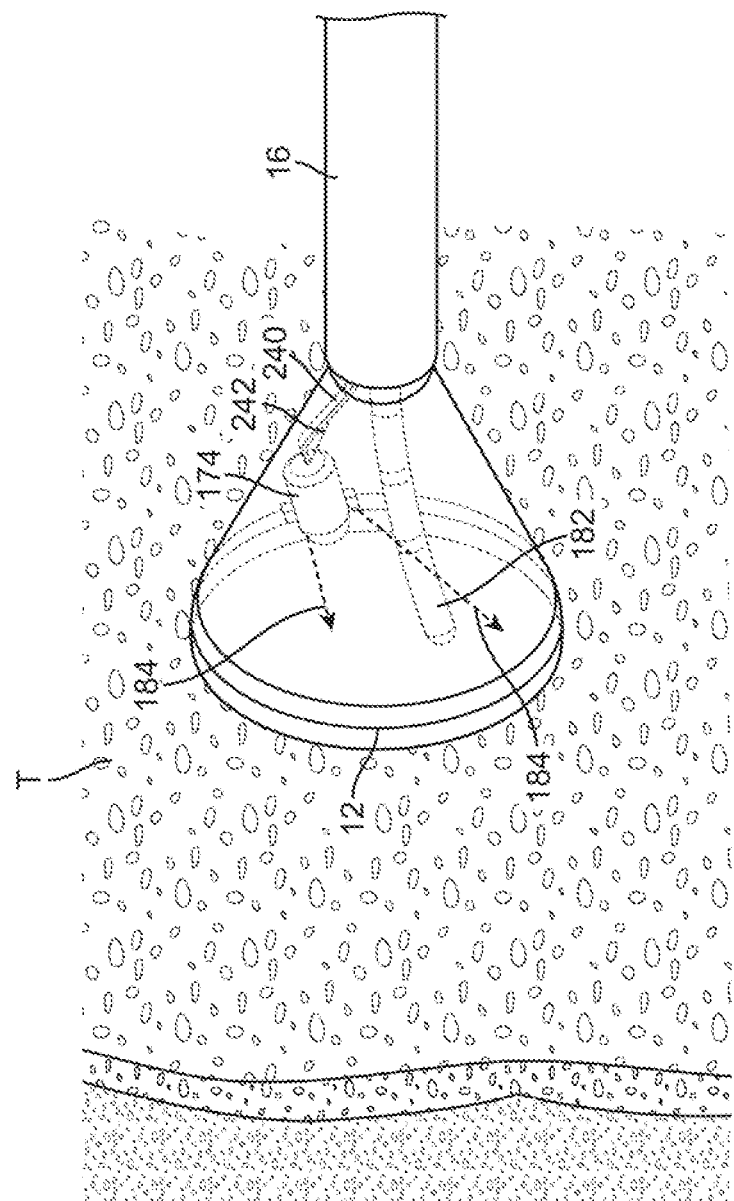

OFF-AXIS VISUALIZATION SYSTEMS

CROSS-REFERENCE TO RELATED APPLICATIONS

This application is a continuation application of U.S. Pat. No. 9,226,648, filed Dec. 20, 2007 which claims the benefit of priority to U.S. Prov. Pat. Apps. 60/871,415 and 60/871,424 both filed Dec. 21, 2006, each of which is incorporated herein by reference in its entirety.

FIELD OF THE INVENTION

The present invention relates generally to medical devices used for visualizing and/or treating regions of tissue within a body. More particularly, the present invention relates to methods and apparatus for directly visualizing tissue regions via imaging systems which are off-axis relative to a longitudinal axis of a deployment catheter and/or treating the issue regions under visualization.

BACKGROUND OF THE INVENTION

Conventional devices for accessing and visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult.

Other external imaging modalities are also conventionally utilized. For example, computed tomography (CT) and magnetic resonance imaging (MRI) are typical modalities which are widely used to obtain images of body lumens such as the interior chambers of the heart. However, such imaging modalities fail to provide real-time imaging for intra-operative therapeutic procedures. Fluoroscopic imaging, for instance, is widely used to identify anatomic landmarks within the heart and other regions of the body. However, fluoroscopy fails to provide an accurate image of the tissue quality or surface and also fails to provide for instrumentation for performing tissue manipulation or other therapeutic procedures upon the visualized tissue regions. In addition, fluoroscopy provides a shadow of the intervening tissue onto a plate or sensor when it may be desirable to view the intraluminal surface of the tissue to diagnose pathologies or to perform some form of therapy on it.

Moreover, many of the conventional imaging systems lack the capability to provide therapeutic treatments or are difficult to manipulate in providing effective therapies. For instance, the treatment in a patient's heart for atrial fibrillation is generally made difficult by a number of factors, such as visualization of the target tissue, access to the target tissue, and instrument articulation and management, amongst others.

Conventional catheter techniques and devices, for example such as those described in U.S. Pat. Nos. 5,895,417; 5,941,845; and 6,129,724, used on the epicardial surface of the heart may be difficult in assuring a transmural lesion or complete blockage of electrical signals. In addition, current devices may have difficulty dealing with varying thickness of tissue through which a transmural lesion desired.

Conventional accompanying imaging devices, such as fluoroscopy, are unable to detect perpendicular electrode orientation, catheter movement during the cardiac cycle, and image catheter position throughout lesion formation. Without real-time visualization, it is difficult to reposition devices to another area that requires transmural lesion ablation. The absence of real-time visualization also poses the risk of incorrect placement and ablation of critical structures such as sinus node tissue which can lead to fatal consequences.

Thus, a tissue imaging system which is able to provide real-time in vivo access to and images of tissue regions within body lumens such as the heart through opaque media such as blood and which also provides instruments for therapeutic procedures are desirable.

SUMMARY OF THE INVENTION

The tissue-imaging apparatus described relates to variations of a device and/or method to provide real-time images in vivo of tissue regions within a body lumen such as a heart, which is filled with blood flowing dynamically therethrough. Such an apparatus may be utilized for many procedures, e.g., mitral valvuloplasty, left atrial appendage closure, arrhythmia ablation, transseptal access and patent foramen ovale closure among other procedures. Further details of such a visualization catheter and methods of use are shown and described in U.S. Pat. Pub. 2006/0184048 A1, which is incorporated herein by reference in its entirety.

A tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or electronic imaging assembly may be disposed for imaging tissue. When deployed, the imaging hood may be expanded into any number of shapes, e.g., cylindrical, conical as shown, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

The imaging hood may be deployed into an expanded shape and retracted within a catheter utilizing various mechanisms. Moreover, the imaging element, such as a CCD or CMOS imaging camera, may be positioned distally or proximally of the imaging hood when collapsed into its low-profile configuration. Such a configuration may reduce or eliminate friction during deployment and retraction as well as increase the available space within the catheter not only for the imaging unit but also for the hood.

Moreover, the imaging element may be introduced along or within the hood into an off-axis position relative to a longitudinal axis of the catheter and/or hood for providing direct visualization of the underlying tissue to be visually examined and/or treated. For example, one variation may utilize a flexible section located at a distal end of the catheter which may be configured from various flexible materials coupled or integrated with a relatively rigid section located proximally of flexible section. The imaging element may be positioned and/or attached to a lateral inner wall of the flexible section such that when the section is collapsed within the sheath, the imaging element may be placed in an in-line or axially positioned relative to the catheter and hood to provide for a low-profile delivery configuration.

Upon deployment of the hood from the constraints of the sheath, the hood and flexible section may be advanced distal to the sheath such that the hood is free to expand or to be expanded and the flexible section is also unconstrained to expand or to be expanded as well such that a portion of the flexible section extends laterally relative to the hood and the catheter to form an imager retaining channel or pocket. The retaining channel or pocket may extend laterally a sufficient distance, either self-expanding or pushed open via the imager being urged laterally into the space, such that the space distal to the catheter is unobstructed by the imager or retaining channel. Alternatively, if the flexible section is self-expanding when pushed out of the sheath such that it expands to its original lateral configuration when not constrained by the sheath, the section may urge imager into its off-axis position if attached to one another.

Because the imager is positioned laterally, the catheter and hood may accommodate a variety of sizes for different types of imagers. For instance, relatively larger, more economical, and/or relatively more powerful CCD or CMOS imagers may be utilized with the system as the hood may accommodate a range of sizes and configurations for the imaging system. With the imager positioned in its off-axis location relative to the hood and/or catheter, the user may obtain a better angle of visualization of the entire operating landscape, including both the movements of the tools and the target tissue surface during any number of therapeutic and/or diagnostic procedures. Moreover, the unobstructed opening of the catheter may allow for various instruments, such as RF ablation probes, graspers, needles, etc., to be deployed through the catheter and past the imager into the open area defined by the hood for treatment upon the underlying imaged tissue.

Various other configurations for positioning the imaging element off-axis may include us of instruments such as a dilator positioned proximal to the flexible segment. The dilator may be translatable through the deployment catheter and may also define one or more working lumens therethrough for the introduction of one or more instruments. With the imaging element attached laterally within the channel or pocket, the hood and flexible section may be advanced out of the sheath with the imaging element still in its low-profile axial position. The dilator may be pushed distally to expand the collapsed section to its expanded volume to form the channel or pocket, consequently pushing the imaging element laterally to the side where the imaging element may bulge out and stretch the channel or pocket.

Yet other variations may utilize an imager support member which is extendable through the deployment catheter and the collapsed imaging hood to position the imaging element distally of the hood. When the hood is deployed and expanded, the imaging element may be pulled proximally into the hood and into its off-axis position via the support member, which may include one or more curved or linked sections or which may be made from a shape memory alloy which reconfigures itself. In yet another variation, the imaging element may include a tapered or angled proximal surface which is forced to slide against an angled surface which is complementary to the imaging element surface. Proximal actuation of the imager may force the imaging element to slide into an off-axis position. In yet other variations, the imaging element may be urged into its off-axis position via an inflatable elongate balloon which pushes the imager along or within the hood.

BRIEF DESCRIPTION OF THE DRAWINGS

FIGS. 11A to 11C show side, perspective, and end views, respectively, of one variation of the tissue visualization catheter having a collapsed flexible section proximal to or along the hood or barrier or membrane.

FIGS. 12A to 12C show side, perspective, and end views, respectively, of the catheter having the hood expanded and an imaging element positioned off-axis relative to a longitudinal axis of the catheter into the expanded flexible section which forms a retaining channel or pocket.

FIGS. 14A and 14B show another variation where the imaging element is positionable in its off-axis configuration via an instrument such as a dilator positioned proximal to the flexible segment.

FIGS. 14C and 14D show partial cross-sectional side views of the dilator positioned proximally of the imaging element.

FIGS. 14E to 14G show side, perspective, and detail perspective views, respectively, of the dilator pushed distally through the flexible segment to expand the work channel allowing tools to pass through and also pushing the imaging element off-axis relative to the catheter longitudinal axis.

FIG. 15 shows a side view of a visualization catheter where the dilator instrument may be preformed into a curved or arcuate shape such that the sheath and/or deployment catheter conforms into the curved or arcuate shape.

FIGS. 16A and 16B show side views of another variation having the flexible section proximal to the hood and defining a slit near or along a distal end of the work channel for expandably receiving the imaging element which protrudes distally from the sheath when in its low-profile configuration.

FIGS. 16C and 16D show perspective and detailed perspective views, respectively, of the visualization catheter where the slit and flexible portion may protrude distally of the sheath for deployment.

FIG. 25 shows a perspective view of the visualization catheter placed against a tissue surface with the off-axis imaging element providing an elevated off-axis image to better estimate tool movements during therapeutic procedures.

DETAILED DESCRIPTION OF THE INVENTION

A tissue-imaging and manipulation apparatus described below is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures. Further examples of tissue visualization catheters which may be utilized are shown and described in further detail in U.S. patent application Ser. No. 11/259,498 filed Oct. 25, 2005, which has been incorporated hereinabove by reference in its entirety.

Figure 1A:
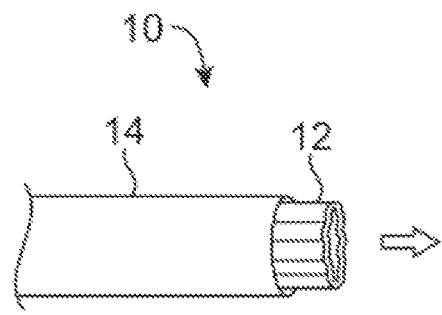
FIG. 1A shows a side view of one variation of a tissue imaging apparatus during deployment from a sheath or delivery catheter.
Figure 1B:
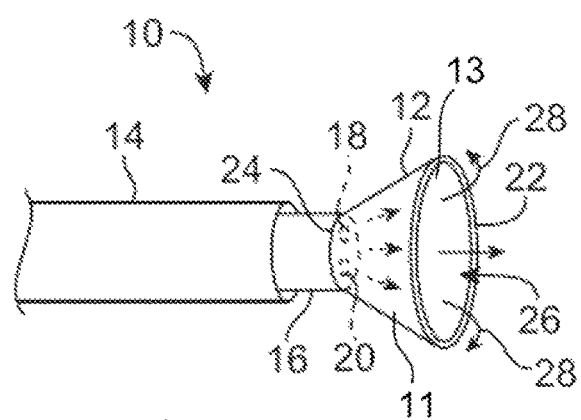
FIG. 1B shows the deployed tissue imaging apparatus of FIG. 1A having an optionally expandable hood or sheath attached to an imaging and/or diagnostic catheter.
Figure 1C:
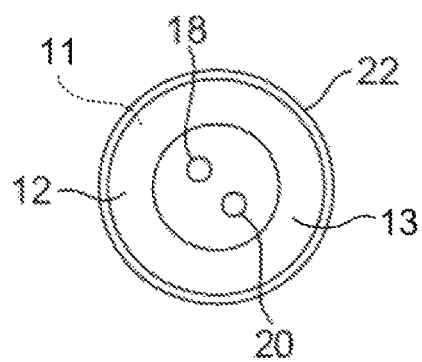
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, such as the mitral valve located at the outflow tract of the left atrium of the heart, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 1D:
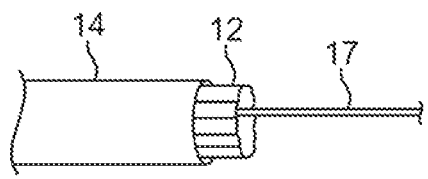
FIGS. 1D to 1F show the apparatus of FIGS. 1A to 1C with an additional lumen, e.g., for passage of a guidewire therethrough.
Figure 1E:
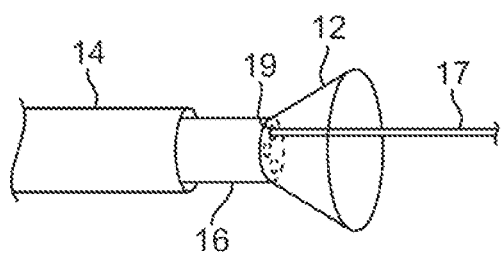
Figure 1F:
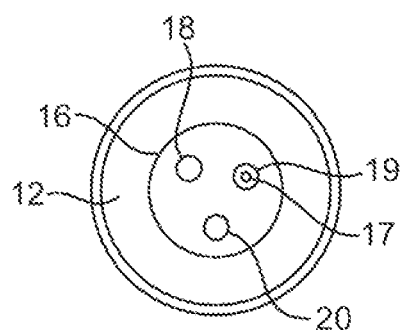

The imaging and manipulation assembly 10 may additionally define a guidewire lumen therethrough, e.g., a concentric or eccentric lumen, as shown in the side and end views, respectively, of FIGS. 1D to 1F. The deployment catheter 16 may define guidewire lumen 19 for facilitating the passage of the system over or along a guidewire 17, which may be advanced intravascularly within a body lumen. The deployment catheter 16 may then be advanced over the guidewire 17, as generally known in the art.

In operation, after imaging hood 12 has been deployed, as in FIG. 1B, and desirably positioned against the tissue region to be imaged along contact edge 22, the displacing fluid may be pumped at positive pressure through fluid delivery lumen 18 until the fluid fills open area 26 completely and displaces any fluid 28 from within open area 26. The displacing fluid flow may be laminarized to improve its clearing effect and to help prevent blood from re-entering the imaging hood 12. Alternatively, fluid flow may be started before the deployment takes place. The displacing fluid, also described herein as imaging fluid, may comprise any biocompatible fluid, e.g., saline, water, plasma, etc., which is sufficiently transparent to allow for relatively undistorted visualization through the fluid. Alternatively or additionally, any number of therapeutic drugs may be suspended within the fluid or may comprise the fluid itself which is pumped into open area 26 and which is subsequently passed into and through the heart and the patient body.

Figure 2A:
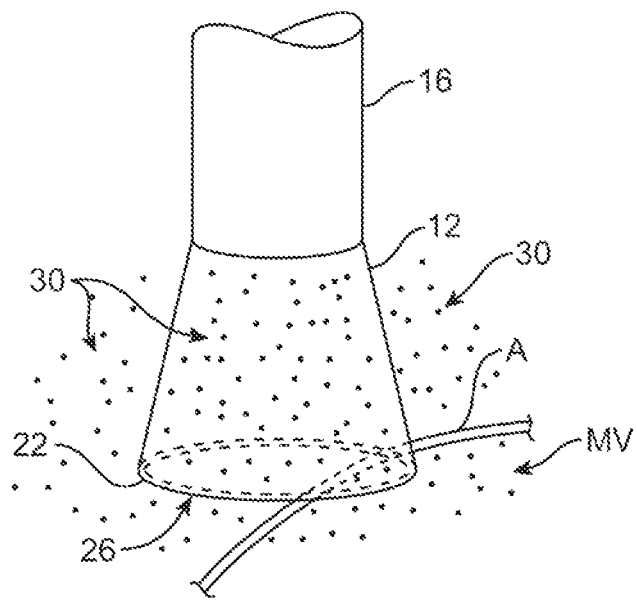
FIGS. 2A and 2B show one example of a deployed tissue imager positioned against or adjacent to the tissue to be imaged and a flow of fluid, such as saline, displacing blood from within the expandable hood.
Figure 2B:
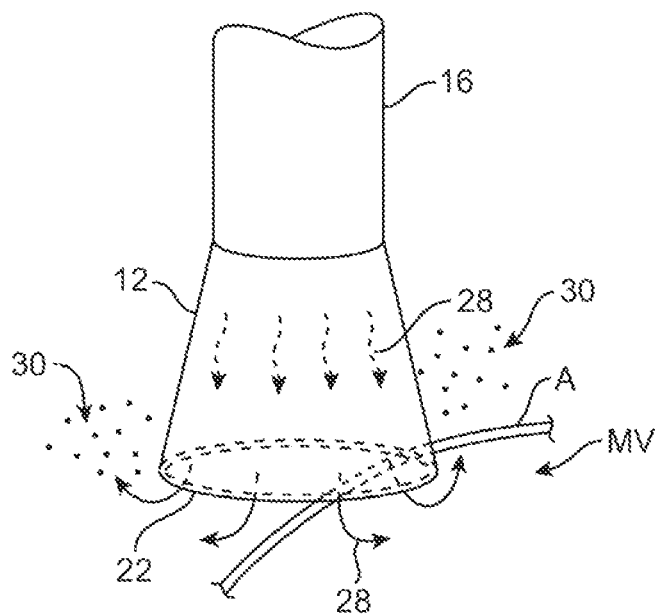

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
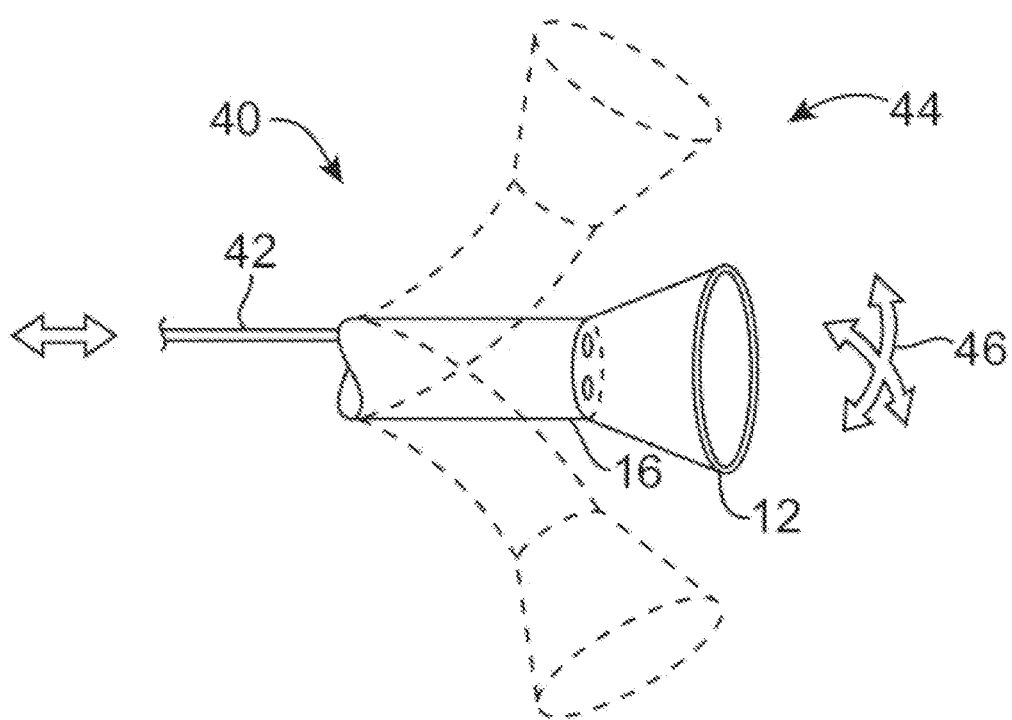
FIG. 3A shows an articulatable imaging assembly which may be manipulated via push-pull wires or by computer control.

In desirably positioning the assembly at various regions within the patient body, a number of articulation and manipulation controls may be utilized. For example, as shown in the articulatable imaging assembly 40 in FIG. 3A, one or more push-pull wires 42 may be routed through deployment catheter 16 for steering the distal end portion of the device in various directions 46 to desirably position the imaging hood 12 adjacent to a region of tissue to be visualized. Depending upon the positioning and the number of push-pull wires 42 utilized, deployment catheter 16 and imaging hood 12 may be articulated into any number of configurations 44. The push-pull wire or wires 42 may be articulated via their proximal ends from outside the patient body manually utilizing one or more controls. Alternatively, deployment catheter 16 may be articulated by computer control, as further described below.

Figure 3B:
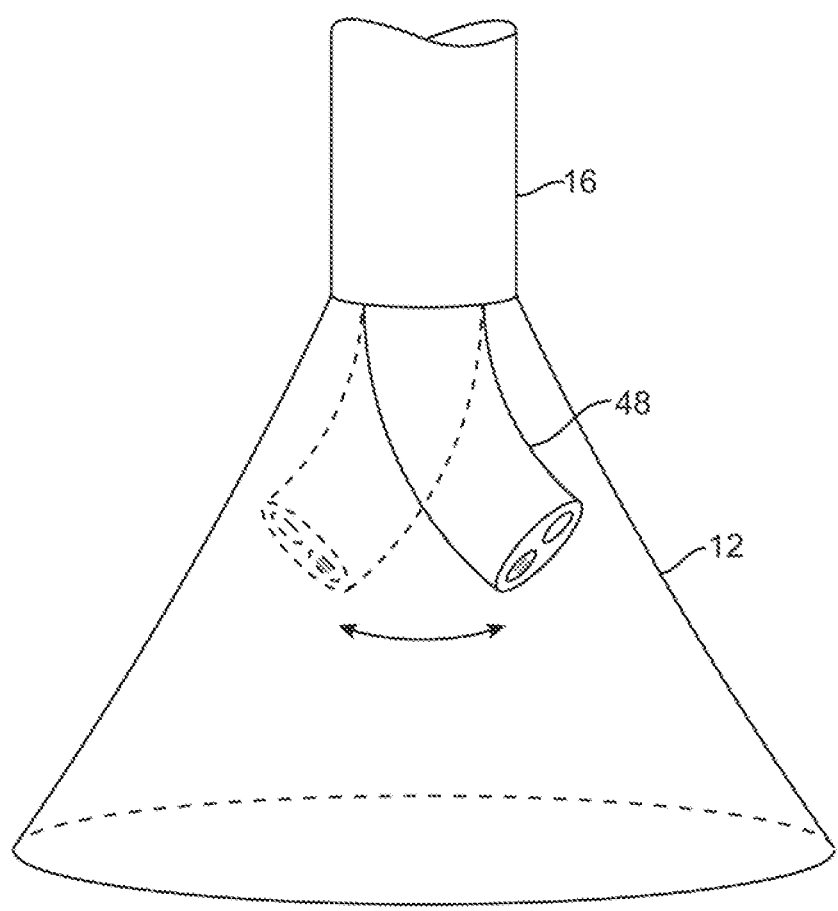
FIGS. 3B and 3C show steerable instruments, respectively, where an articulatable delivery catheter may be steered within the imaging hood or a distal portion of the deployment catheter itself may be steered.

Additionally or alternatively, an articulatable delivery catheter 48, which may be articulated via one or more push-pull wires and having an imaging lumen and one or more working lumens, may be delivered through the deployment catheter 16 and into imaging hood 12. With a distal portion of articulatable delivery catheter 48 within imaging hood 12, the clear displacing fluid may be pumped through delivery catheter 48 or deployment catheter 16 to clear the field within imaging hood 12. As shown in FIG. 3B, the articulatable delivery catheter 48 may be articulated within the imaging hood to obtain a better image of tissue adjacent to the imaging hood 12. Moreover, articulatable delivery catheter 48 may be articulated to direct an instrument or tool passed through the catheter 48, as described in detail below, to specific areas of tissue imaged through imaging hood 12 without having to reposition deployment catheter 16 and re-clear the imaging field within hood 12.

Figure 3C:
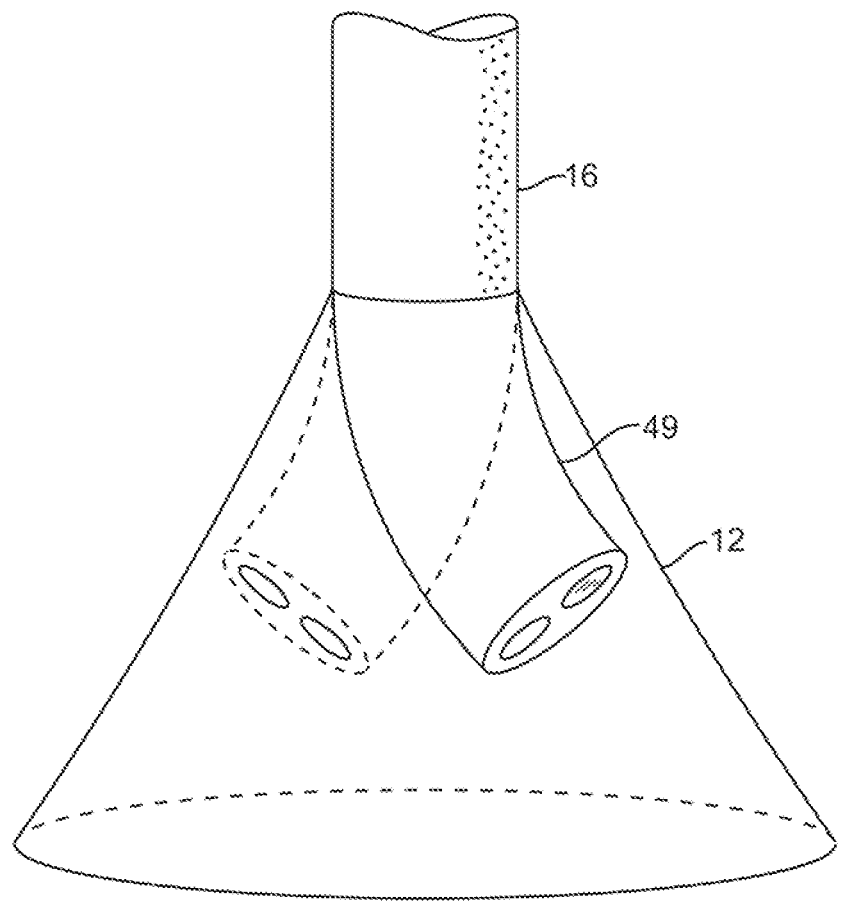

Alternatively, rather than passing an articulatable delivery catheter 48 through the deployment catheter 16, a distal portion of the deployment catheter 16 itself may comprise a distal end 49 which is articulatable within imaging hood 12, as shown in FIG. 3C. Directed imaging, instrument delivery, etc., may be accomplished directly through one or more lumens within deployment catheter 16 to specific regions of the underlying tissue imaged within imaging hood 12.

Figure 4A:
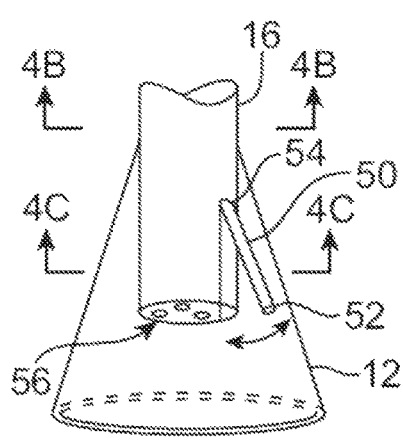
FIGS. 4A to 4C show side and cross-sectional end views, respectively, of another variation having an off-axis imaging capability.

Visualization within the imaging hood 12 may be accomplished through an imaging lumen 20 defined through deployment catheter 16, as described above. In such a configuration, visualization is available in a straight-line manner, i.e., images are generated from the field distally along a longitudinal axis defined by the deployment catheter 16. Alternatively or additionally, an articulatable imaging assembly having a pivotable support member 50 may be connected to, mounted to, or otherwise passed through deployment catheter 16 to provide for visualization off-axis relative to the longitudinal axis defined by deployment catheter 16, as shown in FIG. 4A. Support member 50 may have an imaging element 52, e.g., a CCD or CMOS imager or optical fiber, attached at its distal end with its proximal end connected to deployment catheter 16 via a pivoting connection 54.

Figure 4B:
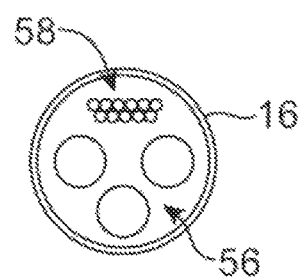
Figure 4C:
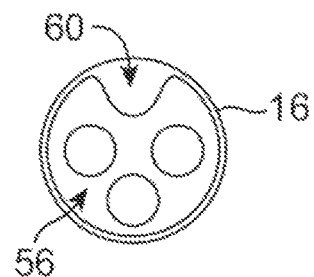

If one or more optical fibers are utilized for imaging, the optical fibers 58 may be passed through deployment catheter 16, as shown in the cross-section of FIG. 4B, and routed through the support member 50. The use of optical fibers 58 may provide for increased diameter sizes of the one or several lumens 56 through deployment catheter 16 for the passage of diagnostic and/or therapeutic tools therethrough. Alternatively, electronic chips, such as a charge coupled device (CCD) or a CMOS imager, which are typically known, may be utilized in place of the optical fibers 58, in which case the electronic imager may be positioned in the distal portion of the deployment catheter 16 with electric wires being routed proximally through the deployment catheter 16. Alternatively, the electronic imagers may be wirelessly coupled to a receiver for the wireless transmission of images. Additional optical fibers or light emitting diodes (LEDs) can be used to provide lighting for the image or operative theater, as described below in further detail. Support member 50 may be pivoted via connection 54 such that the member 50 can be positioned in a low-profile configuration within channel or groove 60 defined in a distal portion of catheter 16, as shown in the cross-section of FIG. 4C. During intravascular delivery of deployment catheter 16 through the patient body, support member 50 can be positioned within channel or groove 60 with imaging hood 12 also in its low-profile configuration. During visualization, imaging hood 12 may be expanded into its deployed configuration and support member 50 may be deployed into its off-axis configuration for imaging the tissue adjacent to hood 12, as in FIG. 4A. Other configurations for support member 50 for off-axis visualization may be utilized, as desired.

Figure 4D:
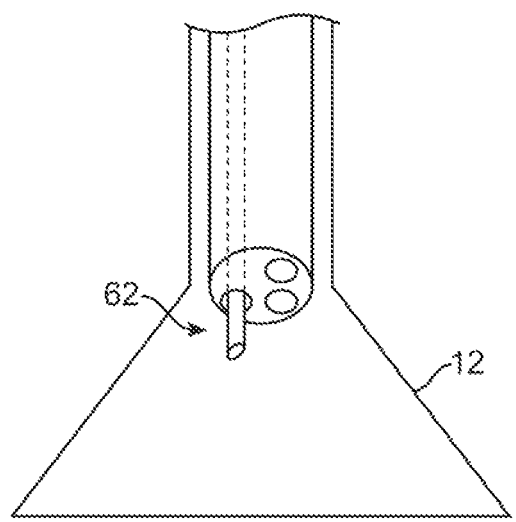
FIGS. 4D and 4E show examples of various visualization imagers which may be utilized within or along the imaging hood.
Figure 4E:
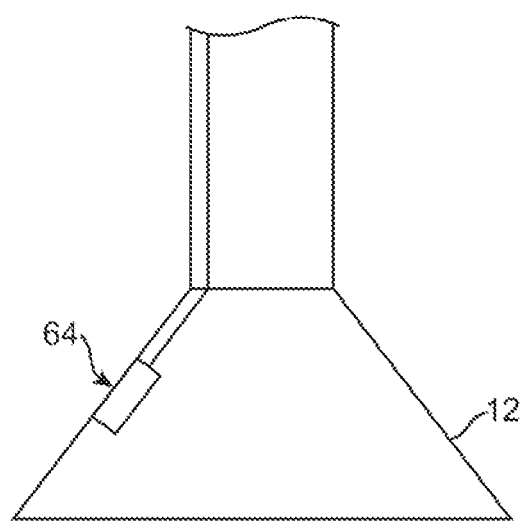

FIG. 4D shows a partial cross-sectional view of an example where one or more optical fiber bundles 62 may be positioned within the catheter and within imaging hood 12 to provide direct in-line imaging of the open area within hood 12. FIG. 4E shows another example where an imaging element 64 (e.g., CCD or CMOS electronic imager) may be placed along an interior surface of imaging hood 12 to provide imaging of the open area such that the imaging element 64 is off-axis relative to a longitudinal axis of the hood 12. The off-axis position of element 64 may provide for direct visualization and uninhibited access by instruments from the catheter to the underlying tissue during treatment.

Figure 5:
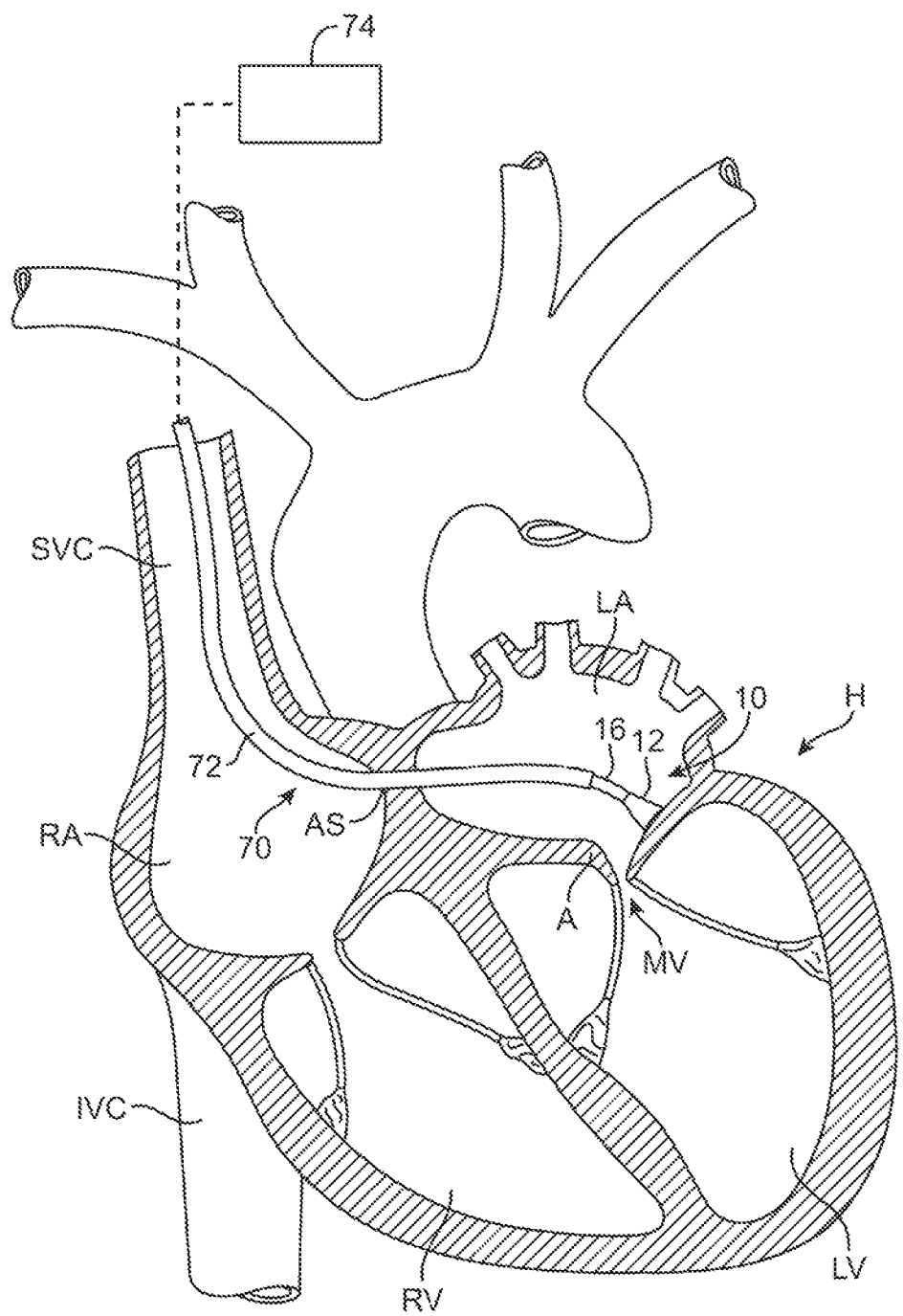
FIG. 5 shows an illustrative view of an example of a tissue imager advanced intravascularly within a heart for imaging tissue regions within an atrial chamber.

FIG. 5 shows an illustrative cross-sectional view of a heart H having tissue regions of interest being viewed via an imaging assembly 10. In this example, delivery catheter assembly 70 may be introduced percutaneously into the patient's vasculature and advanced through the superior vena cava SVC and into the right atrium RA. The delivery catheter or sheath 72 may be articulated through the atrial septum AS and into the left atrium LA for viewing or treating the tissue, e.g., the annulus A, surrounding the mitral valve MV. As shown, deployment catheter 16 and imaging hood 12 may be advanced out of delivery catheter 72 and brought into contact or in proximity to the tissue region of interest. In other examples, delivery catheter assembly 70 may be advanced through the inferior vena cava IVC, if so desired. Moreover, other regions of the heart H, e.g., the right ventricle RV or left ventricle LV, may also be accessed and imaged or treated by imaging assembly 10.

In accessing regions of the heart H or other parts of the body, the delivery catheter or sheath 14 may comprise a conventional intra-vascular catheter or an endoluminal delivery device. Alternatively, robotically-controlled delivery catheters may also be optionally utilized with the imaging assembly described herein, in which case a computer-controller 74 may be used to control the articulation and positioning of the delivery catheter 14. An example of a robotically-controlled delivery catheter which may be utilized is described in further detail in US Pat. Pub. 2002/0087169 A 1 to Brock et al. entitled "Flexible Instrument", which is incorporated herein by reference in its entirety. Other robotically-controlled delivery catheters manufactured by Hansen Medical, Inc. (Mountain View, Calif.) may also be utilized with the delivery catheter 14.

Figure 6A:
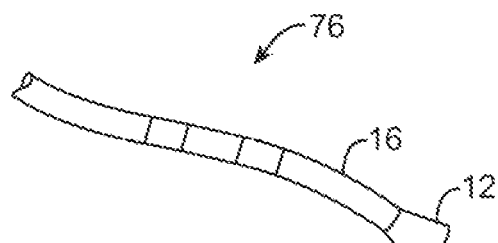
FIGS. 6A to 6C illustrate deployment catheters having one or more optional inflatable balloons or anchors for stabilizing the device during a procedure.
Figure 6B:
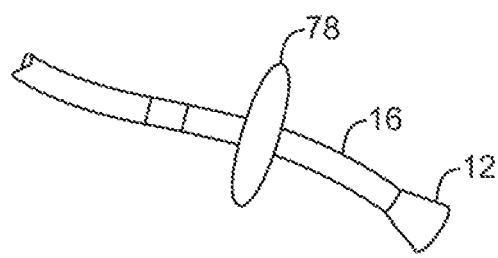
Figure 6C:
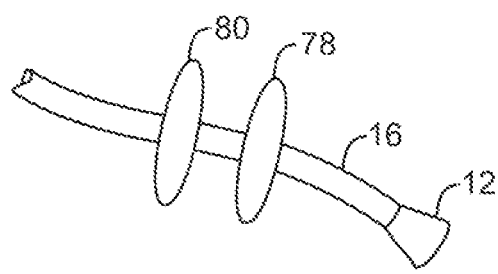

To facilitate stabilization of the deployment catheter 16 during a procedure, one or more inflatable balloons or anchors 76 may be positioned along the length of catheter 16, as shown in FIG. 6A. For example, when utilizing a transseptal approach across the atrial septum AS into the left atrium LA, the inflatable balloons 76 may be inflated from a low-profile into their expanded configuration to temporarily anchor or stabilize the catheter 16 position relative to the heart H. FIG. 6B shows a first balloon 78 inflated while FIG. 6C also shows a second balloon 80 inflated proximal to the first balloon 78. In such a configuration, the septal wall AS may be wedged or sandwiched between the balloons 78, 80 to temporarily stabilize the catheter 16 and imaging hood 12. A single balloon 78 or both balloons 78, 80 may be used. Other alternatives may utilize expandable mesh members, malecots, or any other temporary expandable structure. After a procedure has been accomplished, the balloon assembly 76 may be deflated or re-configured into a low-profile for removal of the deployment catheter 16.

Figure 7A:
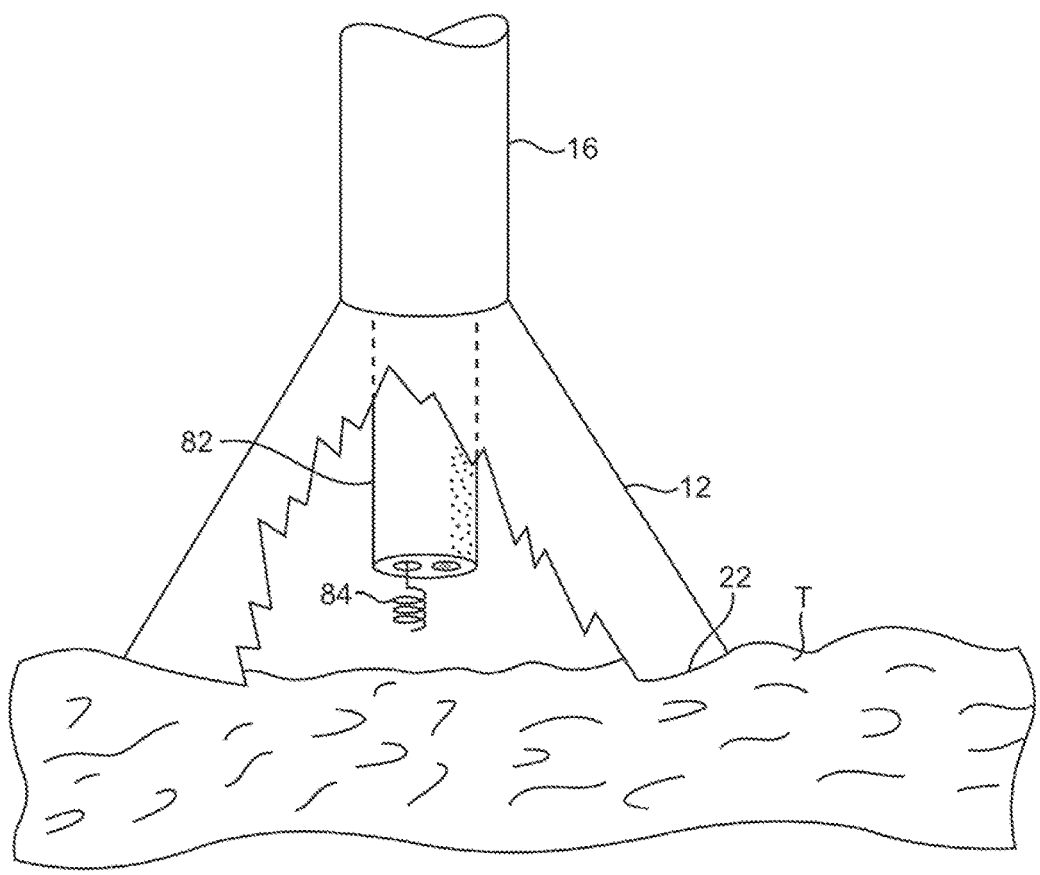
FIGS. 7A and 7B illustrate a variation of an anchoring mechanism such as a helical tissue piercing device for temporarily stabilizing the imaging hood relative to a tissue surface.

To further stabilize a position of the imaging hood 12 relative to a tissue surface to be imaged, various anchoring mechanisms may be optionally employed for temporarily holding the imaging hood 12 against the tissue. Such anchoring mechanisms may be particularly useful for imaging tissue which is subject to movement, e.g., when imaging tissue within the chambers of a beating heart. A tool delivery catheter 82 having at least one instrument lumen and an optional visualization lumen may be delivered through deployment catheter 16 and into an expanded imaging hood 12. As the imaging hood 12 is brought into contact against a tissue surface T to be examined, anchoring mechanisms such as a helical tissue piercing device 84 may be passed through the tool , delivery catheter 82, as shown in FIG. 7A, and into imaging hood 12.

Figure 7B:
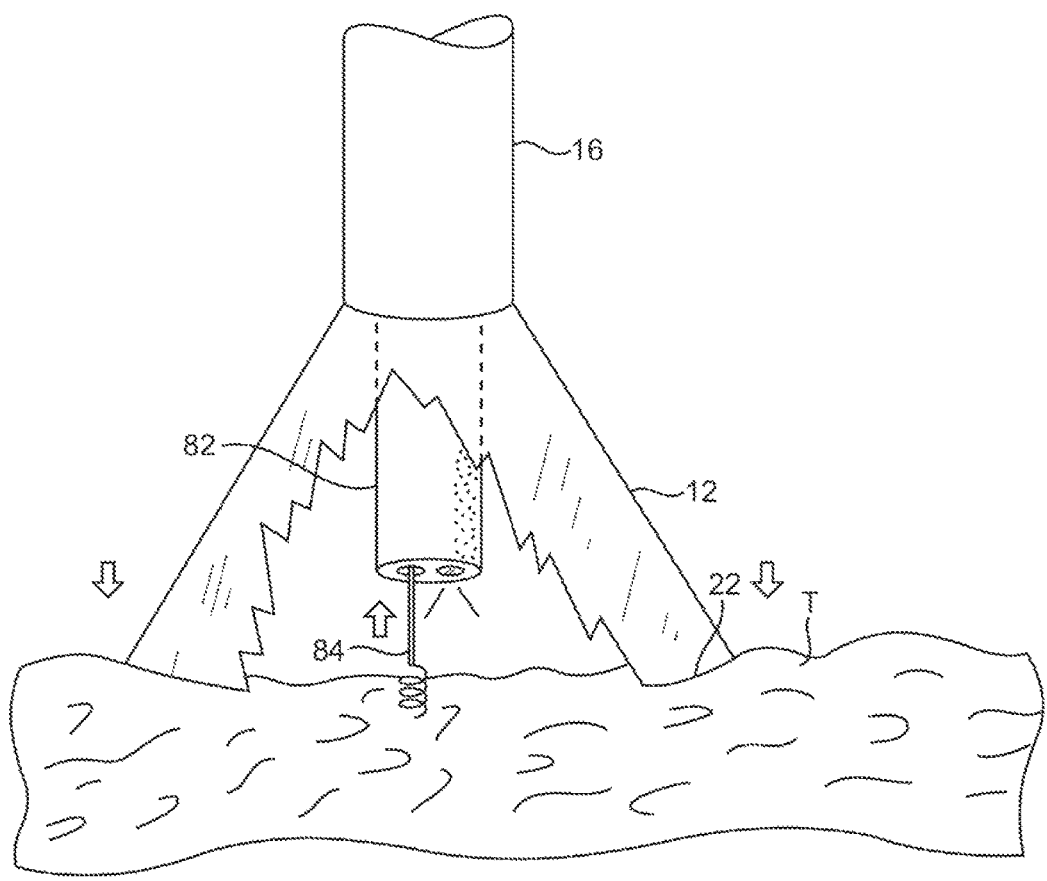

The helical tissue engaging device 84 may be torqued from its proximal end outside the patient body to temporarily anchor itself into the underlying tissue surface T. Once embedded within the tissue T, the helical tissue engaging device 84 may be pulled proximally relative to deployment catheter 16 while the deployment catheter 16 and imaging hood 12 are pushed distally, as indicated by the arrows in FIG. 7B, to gently force the contact edge or lip 22 of imaging hood against the tissue T. The positioning of the tissue engaging device 84 may be locked temporarily relative to the deployment catheter 16 to ensure secure positioning of the imaging hood 12 during a diagnostic or therapeutic procedure within the imaging hood 12. After a procedure, tissue engaging device 84 may be disengaged from the tissue by torquing its proximal end in the opposite direction to remove the anchor form the tissue T and the deployment catheter 16 may be repositioned to another region of tissue where the anchoring process may be repeated or removed from the patient body. The tissue engaging device 84 may also be constructed from other known tissue engaging devices such as vacuum-assisted engagement or grasper-assisted engagement tools, among others.

Although a helical anchor 84 is shown, this is intended to be illustrative and other types of temporary anchors may be utilized, e.g., hooked or barbed anchors, graspers, etc. Moreover, the tool delivery catheter 82 may be omitted entirely and the anchoring device may be delivered directly through a lumen defined through the deployment catheter 16.

Figure 7C:
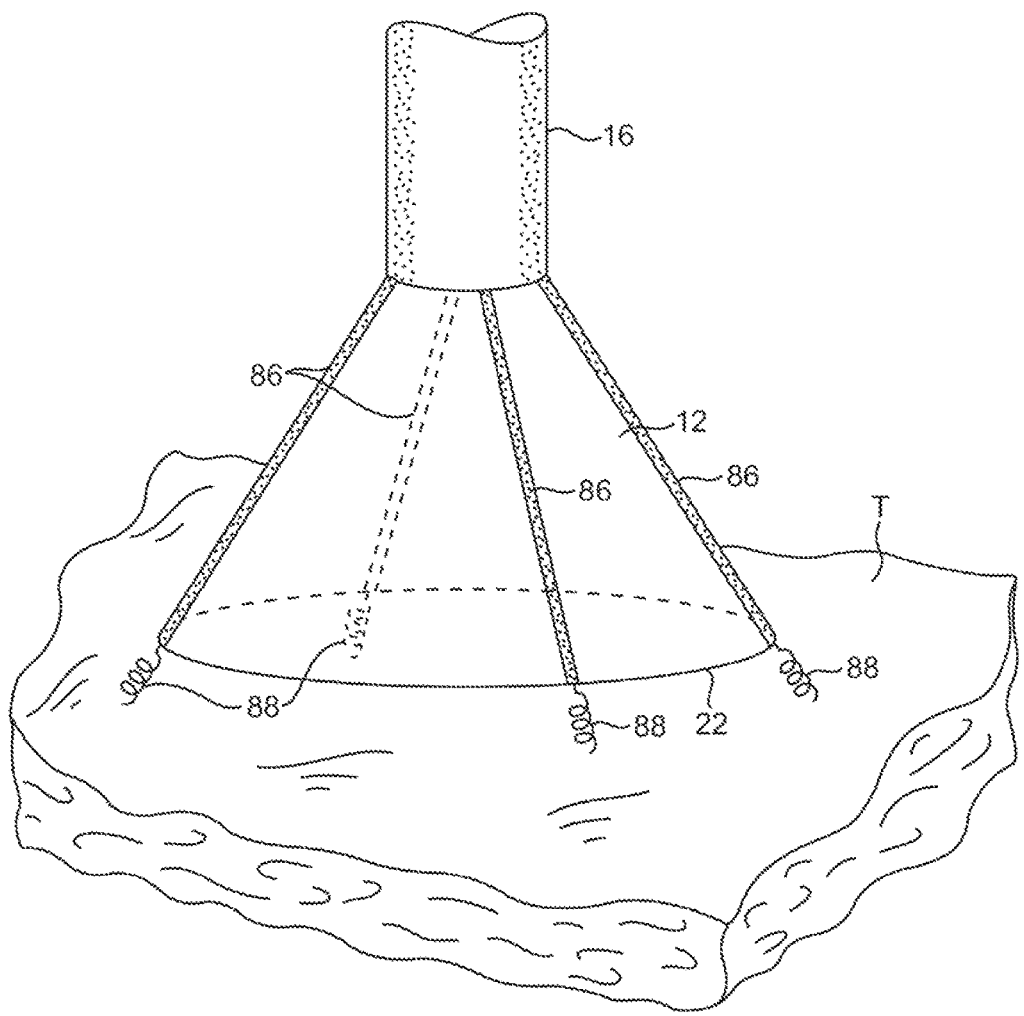
FIG. 7C shows another variation for anchoring the imaging hood having one or more tubular support members integrated with the imaging hood; each support members may define a lumen therethrough for advancing a helical tissue anchor within.

In another variation where the tool delivery catheter 82 may be omitted entirely to temporarily anchor imaging hood 12, FIG. 7C shows an imaging hood 12 having one or more tubular support members 86, e.g., four support members 86 as shown, integrated with the imaging hood 12. The tubular support members 86 may define lumens therethrough each having helical tissue engaging devices 88 positioned within. When an expanded imaging hood 12 is to be temporarily anchored to the tissue, the helical tissue engaging devices 88 may be urged distally to extend from imaging hood 12 and each may be torqued from its proximal end to engage the underlying tissue T. Each of the helical tissue engaging devices 88 may be advanced through the length of deployment catheter 16 or they may be positioned within tubular support members 86 during the delivery and deployment of imaging hood 12. Once the procedure within imaging hood 12 is finished, each of the tissue engaging devices 88 may be disengaged from the tissue and the imaging hood 12 may be repositioned to another region of tissue or removed from the patient body.

Figure 8A:
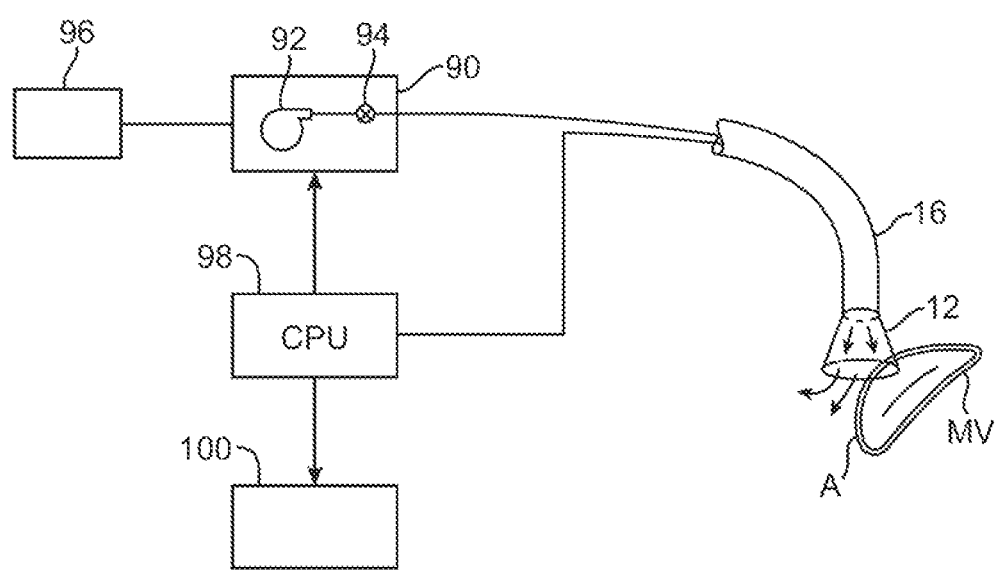
FIG. 8A shows an illustrative example of one variation of how a tissue imager may be utilized with an imaging device.

An illustrative example is shown in FIG. 8A of a tissue imaging assembly connected to a fluid delivery system 90 and to an optional processor 98 and image recorder and/or viewer 100. The fluid delivery system 90 may generally comprise a pump 92 and an optional valve 94 for controlling the flow rate of the fluid into the system. A fluid reservoir 96, fluidly connected to pump 92, may hold the fluid to be pumped through imaging hood 12. An optional central processing unit or processor 98 may be in electrical communication with fluid delivery system 90 for controlling flow parameters such as the flow rate and/or velocity of the pumped fluid. The processor 98 may also be in electrical communication with an image recorder and/or viewer 100 for directly viewing the images of tissue received from within imaging hood 12. Imager recorder and/or viewer 100 may also be used not only to record the image but also the location of the viewed tissue region, if so desired.

Optionally, processor 98 may also be utilized to coordinate the fluid flow and the image capture. For instance, processor 98 may be programmed to provide for fluid flow from reservoir 96 until the tissue area has been displaced of blood to obtain a clear image. Once the image has been determined to be sufficiently clear, either visually by a practitioner or by computer, an image of the tissue may be captured automatically by recorder 100 and pump 92 may be automatically stopped or slowed by processor 98 to cease the fluid flow into the patient. Other variations for fluid delivery and image capture are, of course, possible and the aforementioned configuration is intended only to be illustrative and not limiting.

Figure 8B:
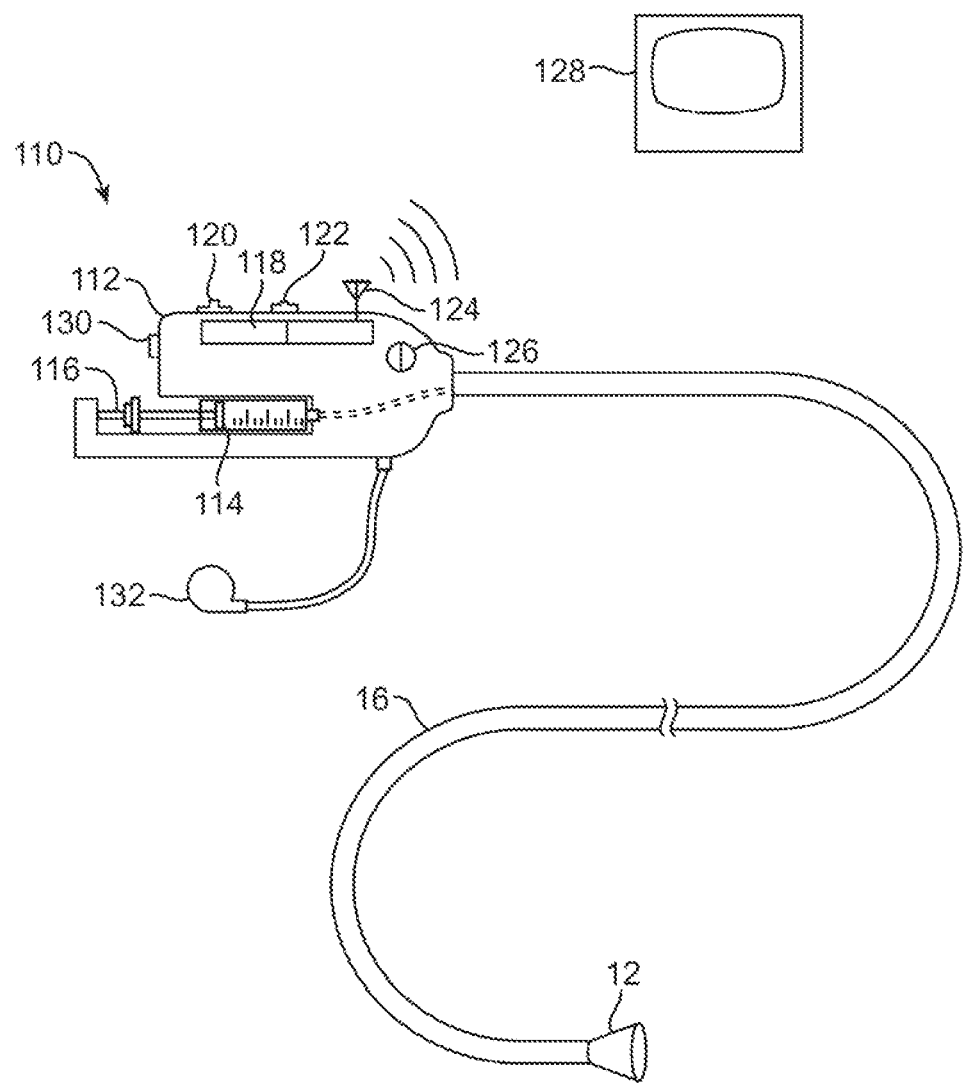
FIG. 8B shows a further illustration of a hand-held variation of the fluid delivery and tissue manipulation system.

FIG. 8B shows a further illustration of a hand-held variation of the fluid delivery and tissue manipulation system 110. In this variation, system 110 may have a housing or handle assembly 112 which can be held or manipulated by the physician from outside the patient body. The fluid reservoir 114, shown in this variation as a syringe, can be fluidly coupled to the handle assembly 112 and actuated via a pumping mechanism 116, e.g., lead screw. Fluid reservoir 114 may be a simple reservoir separated from the handle assembly 112 and fluidly coupled to handle assembly 112 via one or more tubes. The fluid flow rate and other mechanisms may be metered by the electronic controller 118.

Deployment of imaging hood 12 may be actuated by a hood deployment switch 120 located on the handle assembly 112 while dispensation of the fluid from reservoir 114 may be actuated by a fluid deployment switch 122, which can be electrically coupled to the controller 118. Controller 118 may also be electrically coupled to a wired or wireless antenna 124 optionally integrated with the handle assembly 112, as shown in the figure. The wireless antenna 124 can be used to wirelessly transmit images captured from the imaging hood 12 to a receiver, e.g., via Bluetooth® wireless technology (Bluetooth SIG, Inc., Bellevue, Wash.), RF, etc., for viewing on a monitor 128 or for recording for later viewing.

Articulation control of the deployment catheter 16, or a delivery catheter or sheath 14 through which the deployment catheter 16 may be delivered, may be accomplished by computer control, as described above, in which case an additional controller may be utilized with handle assembly 112. In the case of manual articulation, handle assembly 112 may incorporate one or more articulation controls 126 for manual manipulation of the position of deployment catheter 16. Handle assembly 112 may also define one or more instrument ports 130 through which a number of intravascular tools may be passed for tissue manipulation and treatment within imaging hood 12, as described further below. Furthermore, in certain procedures, fluid or debris may be sucked into imaging hood 12 for evacuation from the patient body by optionally fluidly coupling a suction pump 132 to handle assembly 112 or directly to deployment catheter 16.

Figure 9A:
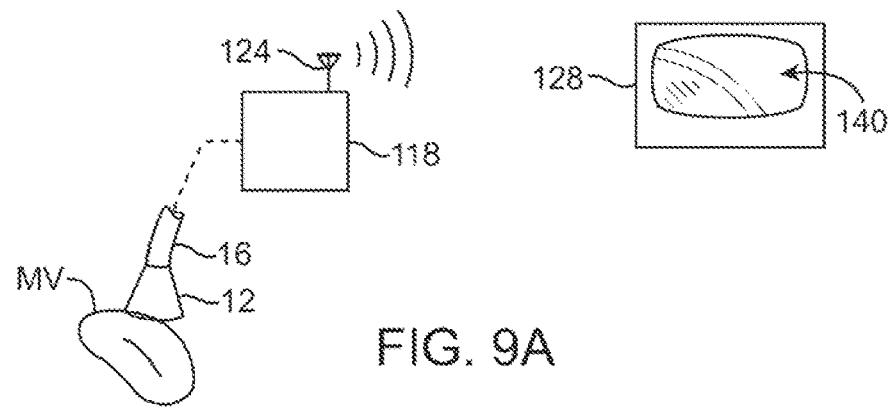
FIGS. 9A to 9C illustrate an example of capturing several images of the tissue at multiple regions.
Figure 9B:
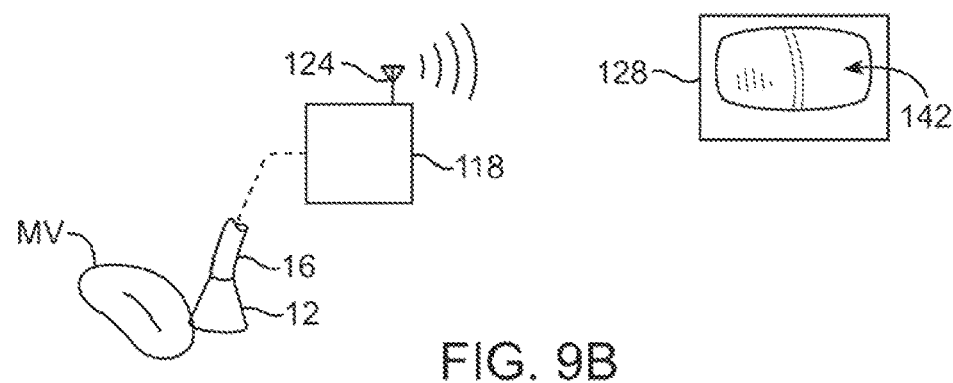
Figure 9C:
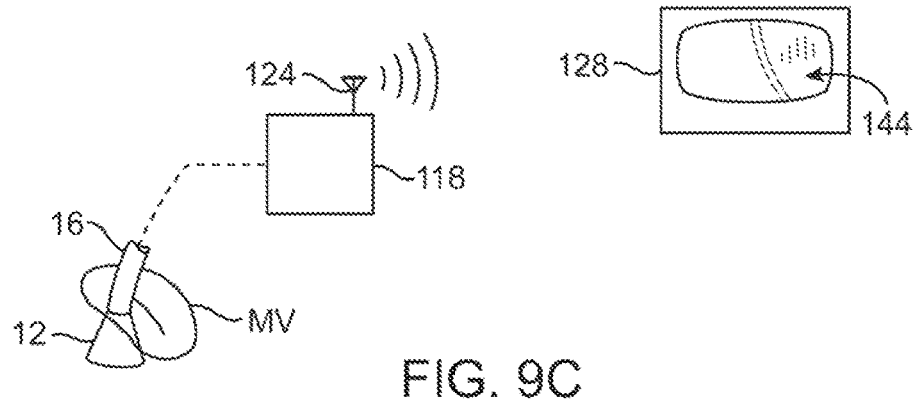

As described above, fluid may be pumped continuously into imaging hood 12 to provide for clear viewing of the underlying tissue. Alternatively, fluid may be pumped temporarily or sporadically only until a clear view of the tissue is available to be imaged and recorded, at which point the fluid flow may cease and the blood may be allowed to seep or flow back into imaging hood 12. FIGS. 9A to 9C illustrate an example of capturing several images of the tissue at multiple regions. Deployment catheter 16 may be desirably positioned and imaging hood 12 deployed and brought into position against a region of tissue to be imaged, in this example the tissue surrounding a mitral valve MV within the left atrium of a patient's heart. The imaging hood 12 may be optionally anchored to the tissue, as described above, and then cleared by pumping the imaging fluid into the hood 12. Once sufficiently clear, the tissue may be visualized and the image captured by control electronics 118. The first captured image 140 may be stored and/or transmitted wirelessly 124 to a monitor 128 for viewing by the physician, as shown in FIG. 9A.

The deployment catheter 16 may be then repositioned to an adjacent portion of mitral valve MV, as shown in FIG. 9B, where the process may be repeated to capture a second image 142 for viewing and/or recording. The deployment catheter 16 may again be repositioned to another region of tissue, as shown in FIG. 9C, where a third image 144 may be captured for viewing and/or recording. This procedure may be repeated as many times as necessary for capturing a comprehensive image of the tissue surrounding mitral valve MV, or any other tissue region. When the deployment catheter 16 and imaging hood 12 is repositioned from tissue region to tissue region, the pump may be stopped during positioning and blood or surrounding fluid may be allowed to enter within imaging hood 12 until the tissue is to be imaged, where the imaging hood 12 may be cleared, as above.

As mentioned above, when the imaging hood 12 is cleared by pumping the imaging fluid within for clearing the blood or other bodily fluid, the fluid may be pumped continuously to maintain the imaging fluid within the hood 12 at a positive pressure or it may be pumped under computer control for slowing or stopping the fluid flow into the hood 12 upon detection of various parameters or until a clear image of the underlying tissue is obtained. The control electronics 118 may also be programmed to coordinate the fluid flow into the imaging hood 12 with various physical parameters to maintain a clear image within imaging hood 12.

Figure 10A:
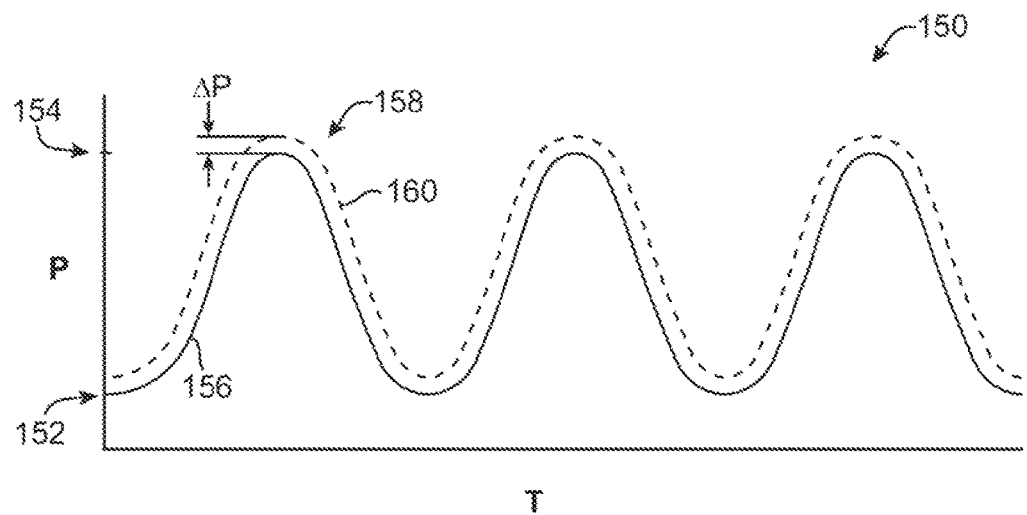
FIGS. 10A and 10B show charts illustrating how fluid pressure within the imaging hood may be coordinated with the surrounding blood pressure; the fluid pressure in the imaging hood may be coordinated with the blood pressure or it may be regulated based upon pressure feedback from the blood.

One example is shown in FIG. 10A which shows a chart 150 illustrating how fluid pressure within the imaging hood 12 may be coordinated with the surrounding blood pressure.

Chart 150 shows the cyclical blood pressure 156 alternating between diastolic pressure 152 and systolic pressure 154 over time T due to the beating motion of the patient heart. The fluid pressure of the imaging fluid, indicated by plot 160, within imaging hood 12 may be automatically timed to correspond to the blood pressure changes 160 such that an increased pressure is maintained within imaging hood 12 which is consistently above the blood pressure 156 by a slight increase ΔP, as illustrated by the pressure difference at the peak systolic pressure 158. This pressure difference, ΔP, may be maintained within imaging hood 12 over the pressure variance of the surrounding blood pressure to maintain a positive imaging fluid pressure within imaging hood 12 to maintain a clear view of the underlying tissue. One benefit of maintaining a constant ΔP is a constant flow and maintenance of a clear field.

Figure 10B:
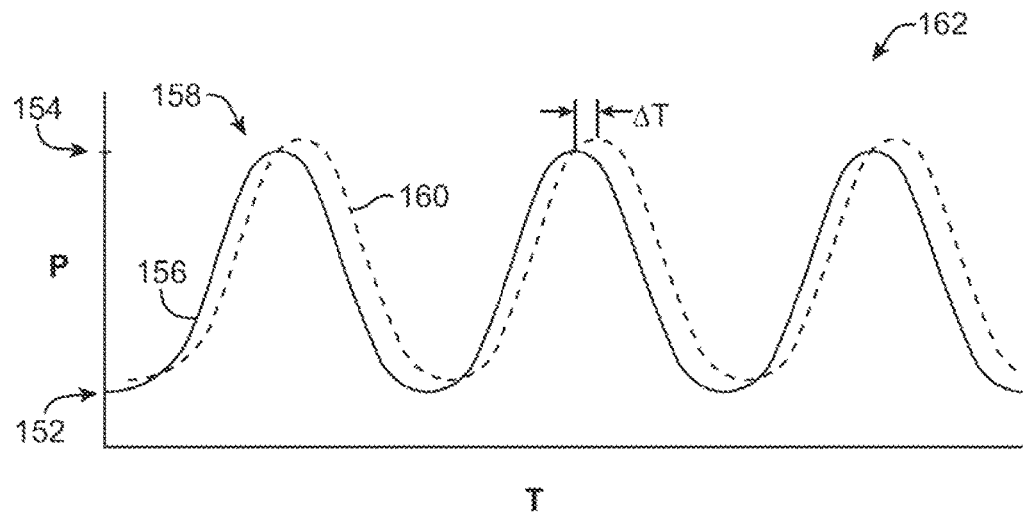

FIG. 10B shows a chart 162 illustrating another variation for maintaining a clear view of the underlying tissue where one or more sensors within the imaging hood 12, as described in further detail below, may be configured to sense pressure changes within the imaging hood 12 and to correspondingly increase the imaging fluid pressure within imaging hood 12. This may result in a time delay, ΔT, as illustrated by the shifted fluid pressure 160 relative to the cycling blood pressure 156, although the time delays ΔT may be negligible in maintaining the clear image of the underlying tissue. Predictive software algorithms can also be used to substantially eliminate this time delay by predicting when the next pressure wave peak will arrive and by increasing the pressure ahead of the pressure wave's arrival by an amount of time equal to the aforementioned time delay to essentially cancel the time delay out.

The variations in fluid pressure within imaging hood 12 may be accomplished in part due to the nature of imaging hood 12. An inflatable balloon, which is conventionally utilized for imaging tissue, may be affected by the surrounding blood pressure changes. On the other hand, an imaging hood 12 retains a constant volume therewithin and is structurally unaffected by the surrounding blood pressure changes, thus allowing for pressure increases therewithin. The material that hood 12 is made from may also contribute to the manner in which the pressure is modulated within this hood 12. A stiffer hood material, such as high durometer polyurethane or Nylon, may facilitate the maintaining of an open hood when deployed. On the other hand, a relatively lower durometer or softer material, such as a low durometer PVC or polyurethane, may collapse from the surrounding fluid pressure and may not adequately maintain a deployed or expanded hood.

As mentioned above, an imaging element, e.g., a CCD or CMOS imager or optical fiber, may be connected to, mounted to, or otherwise passed through deployment catheter 16 to provide for visualization off-axis relative to the longitudinal axis 186 defined by deployment catheter 16. In yet other variations for providing off-axis visualization, an imaging element may be advanced through or along deployment catheter 16 such that the imaging element and hood 12 are arranged to be delivered in a low-profile configuration within sheath 14. Upon deployment of hood 12, the imaging element may be introduced along or within hood 12 into an off-axis position relative to the longitudinal axis of catheter 16 for providing direct visualization of the underlying tissue to be visually examined and/or treated.

FIGS. 11A and 11B illustrate partial cross-sectional side and perspective views, respectively, of one variation of an imaging system which may be positioned off-axis relative to the longitudinal axis 186 of deployment catheter 16. As shown in its low-profile configuration, hood 12 may be collapsed within lumen 176 of sheath 14 and attached to catheter 16, which in this variation may include a flexible section 170 located at a distal end of catheter 16 and which may be configured from various flexible materials coupled or integrated with a relatively rigid section 172 located proximally of flexible section 170. Alternatively, the flexible section 170 may be coupled or integrated to a proximal portion of hood 12. The flexible section 170 may be made from various elastomers or conformable polymers such as silicone, polyvinyl chloride (PVC), polyurethane (PU), polyethylene terephthalate (PET), flexible polymeric tubes reinforced with Nitinol, etc.

In either case, imaging element 174 (e.g., CCD, CMOS, optical fiber, etc.) may be positioned and/or attached to a lateral inner wall of flexible section 170 such that when section 170 is collapsed within sheath 14, as shown, imaging element 174 may be placed in an in-line or axial positioned relative to the catheter 16 and hood 12 to provide for a low-profile delivery configuration, as also shown in the end view of FIG. 11C.

Upon deployment of hood 12 from the constraints of sheath 14, hood 12 and flexible section 170 may be advanced distal to sheath 14 such that hood 12 is free to expand or to be expanded and flexible section 170 is also unconstrained to expand or to be expanded as well such that a portion of flexible section 170 extends laterally relative to hood 12 and catheter 16 to form an imager retaining channel or pocket 178, as shown in the side and perspective views of FIGS. 12A and 12B. Retaining channel or pocket 178 may extend laterally a sufficient distance, either self-expanding or pushed open via imager 174 being urged laterally into the space, such that the space distal to catheter 16 is unobstructed by imager 174 or retaining channel 178, as shown in the end view of FIG. 12C. Alternatively, if flexible section 170 is self-expanding when pushed out of the sheath 14 such that it expands to its original lateral configuration when not constrained by sheath 14, section 170 may urge imager 174 into its off-axis position if attached to one another.

Because imager 174 is positioned laterally, catheter 16 and hood 12 may accommodate a variety of sizes for different types of imagers 174. For instance, relatively larger, more economical, and/or relatively more powerful CCD or CMOS imagers may be utilized with the system as hood 12 may accommodate a range of sizes and configurations for the imaging system. With the imager 174 positioned in its off-axis location relative to the hood 12 and/or catheter 16, the user may obtain a better angle of visualization of the entire operating landscape, including both the movements of the tools and the target tissue surface during any number of therapeutic and/or diagnostic procedures. Moreover, the unobstructed opening of catheter 16 may allow for various instruments, such as RF ablation probes 182, graspers, needles, etc., to be deployed through catheter 16 and past imager 174 into the open area defined by hood 12 for treatment upon the underlying imaged tissue.

Figure 13:
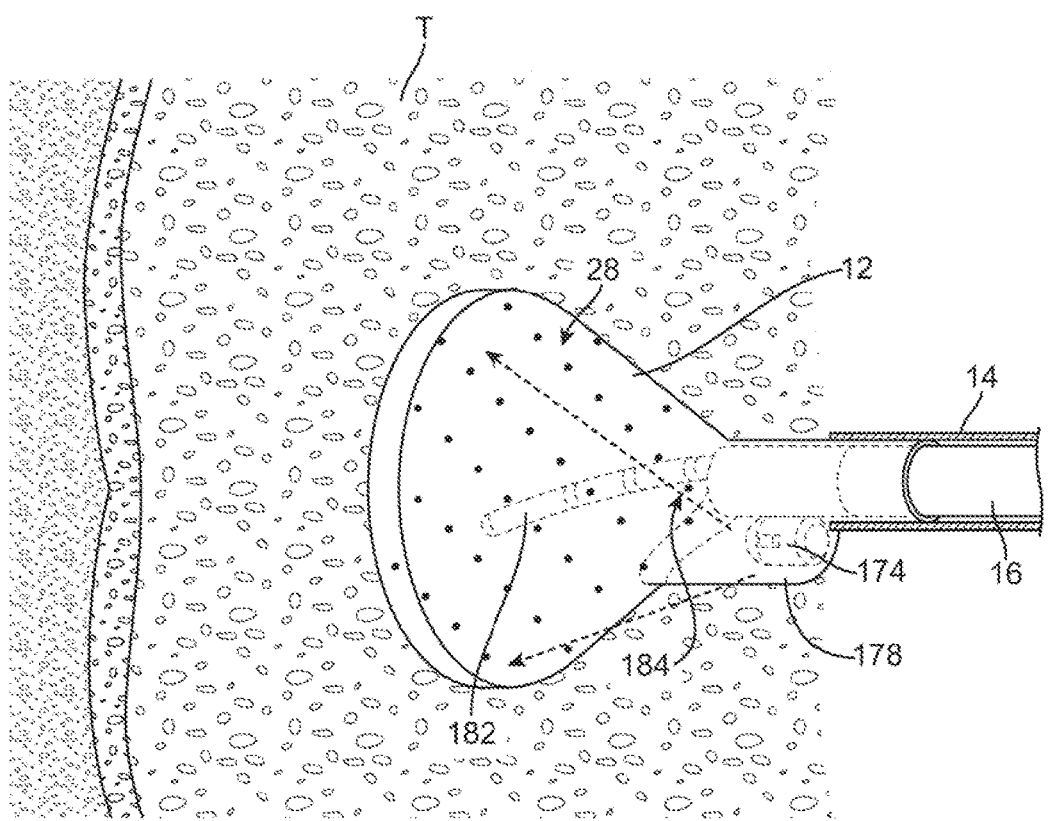
FIG. 13 illustrates a perspective view of the hood placed against a tissue region of interest with the imager providing direct visualization of the underlying tissue while positioned in its off-axis configuration.

FIG. 13 illustrates a perspective view of hood 12 placed against a tissue region of interest T with the imager 174 providing direct visualization of the underlying tissue T while positioned in its off-axis configuration. As described above, the clearing fluid 28 may be pumped into the open area defined by hood 12 to purge the surrounding blood from hood 12 and to provide a clear transparent imaging field (as indicated by the field of view 184) within hood 12, as provided by imager 174. Ablation probe 182 is illustrated as having been advanced through a working lumen of catheter 16, past the off-axis imager 174, and into the interior of hood 12 to treat the underlying tissue T while under direct visualization.

Another variation for an off-axis visualization system is shown in the partial cross-sectional side views of FIGS. 14A and 14B, which illustrate an imaging element 174 which is positionable in its off-axis configuration via an instrument such as a dilator 190 positioned proximal to the flexible segment 170, as shown in the perspective views of FIGS. 14C and 14D. Dilator may be translatable through deployment catheter 16 and may also define one or more working lumens 192, 194, 196 therethrough for the introduction of one or more instruments. With imaging element 174 attached laterally within channel or pocket 178, hood 12 and flexible section 170 may be advanced out of sheath 14 with imaging element 174 still in its low-profile axial position.

As shown in FIGS. 14E to 14G, which show side, perspective, and detail perspective views, respectively, dilator 190 may be pushed distally to expand the collapsed section 170 to its expanded volume to form channel or pocket 178, consequently pushing imaging element 174 laterally to the side where imaging element 174 may bulge out and stretch channel or pocket 178. With the distal end of the work channel unobstructed, various instruments such as RF ablation probe 182, graspers, needles, etc. can be deployed forward into the open area enclosed by the expanded hood 12.

A variety of dilators may also be used with deployment catheter 16 and/or sheath 14. Dilators may define single or multiple lumens according to the needs of the user and the size of the instruments to be used with the tissue visualization catheter. Accordingly, different dilators can be conveniently and quickly swapped while hood 12 is still in the patient's body. In addition, dilators which are preformed to have a curved or arcuate shape may also be used such that catheter 16 and/or sheath 14 may conform into the curved or arcuate shape imparted by the dilator, as shown in FIG. 15. This can be especially useful for procedures such as transseptal puncture of the septal wall.

In yet another variation, FIGS. 16A and 16B show partial cross-sectional side views of hood 12 in its retracted configuration within sheath 14 and in its expanded configuration. In this variation, imaging element 174 may be positioned upon an imager support member 200 which may comprise a wire frame or support fabricated from any number of materials, e.g., Nitinol, stainless steel, titanium, etc. which extends through catheter 16. In its low-profile configuration, imaging element 174 may be positioned distally of the collapsed hood 12 by extending support member 200. Having imaging element 174 positioned distal to hood 12 when retracted in sheath 14 may allow for hood 12 and sheath 14 to accommodate various configurations and sizes of imaging element 174.

Figure 17A:
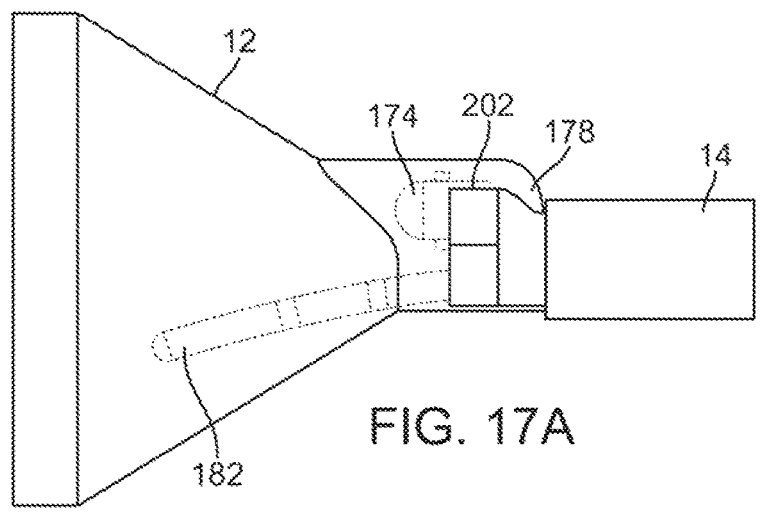
FIGS. 17A to 17C show side, perspective, and detailed perspective views, respectively, of the deployed hood and the imaging element pushed past the slit and positioned off-axis relative to the hood and catheter longitudinal axis.
Figure 17B:
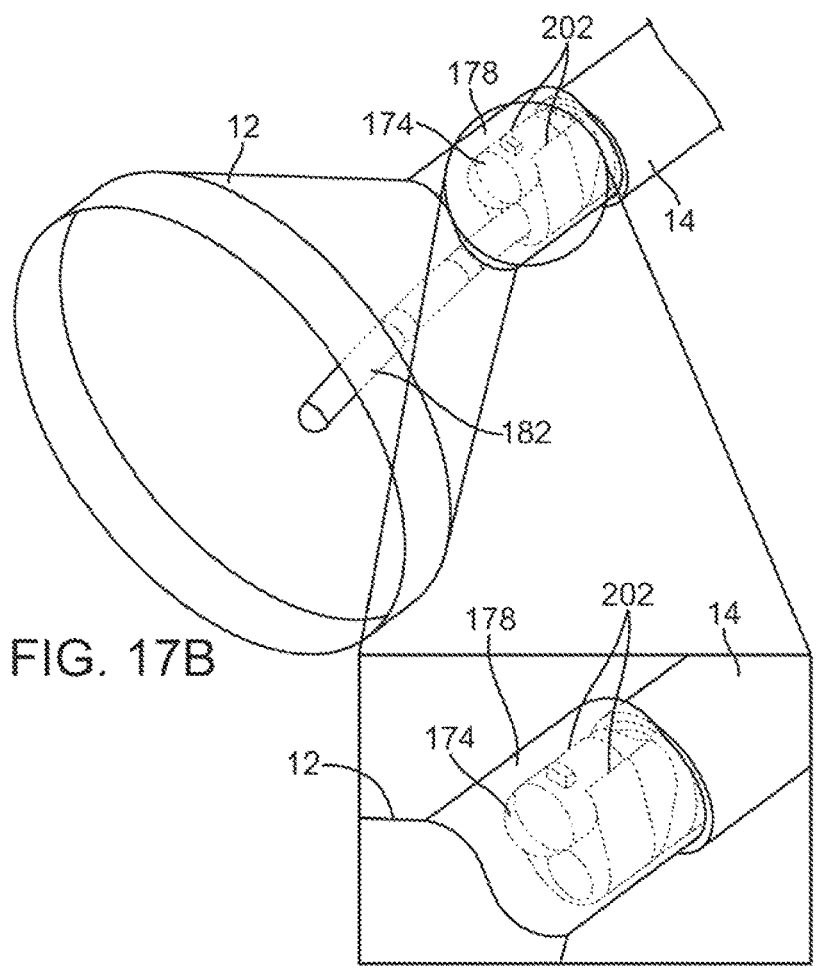
Figure 17C:
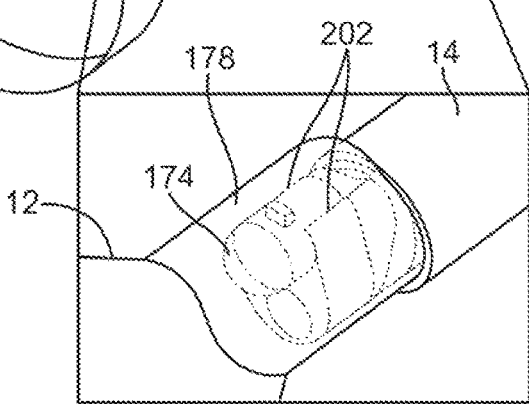

Once hood 12 has been expanded, support member 200 may be pulled proximally to bring imaging element 174 into hood 12 and into its off-axis position. To receive imaging element 174 within hood 12, the flexible section proximal to hood 12 may define a longitudinal slit 202 at least partially along the section, as shown in the perspective and detailed perspective views of FIGS. 16C and 16D. When imaging element 174 is pulled proximally into hood 12, imaging element 174 may slide in-between slit 202 consequently expanding the slit 202 to allow for imaging element 174 to bulge laterally into its off-axis position and form receiving channel or pocket 178, as shown in the side and perspective views of FIGS. 17A to 17C. Any number of instruments may then be advanced into and/or through hood 12 past the off-axis imaging element 174.

Figure 18A:
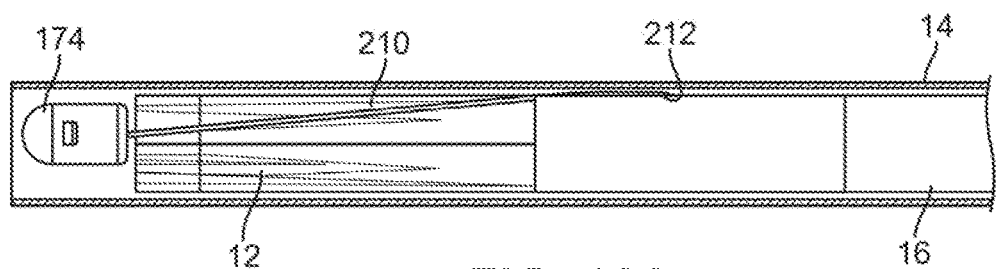
FIGS. 18A and 18B show side views of another variation of the tissue visualization catheter with an imaging element positioned distal to the collapsed hood in the retracted configuration within the sheath and also upon hood deployment.
Figure 18B:
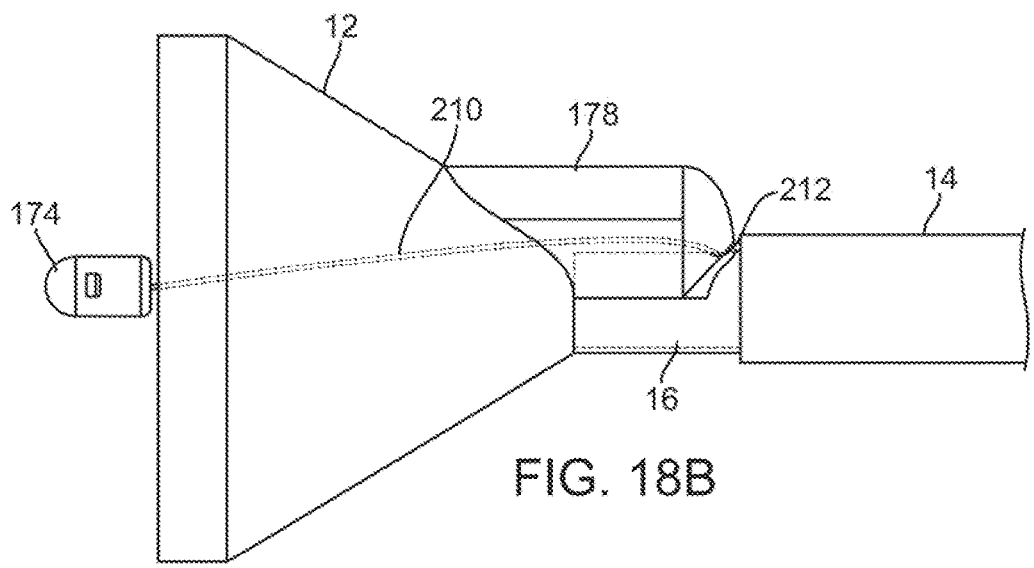
Figure 18C:
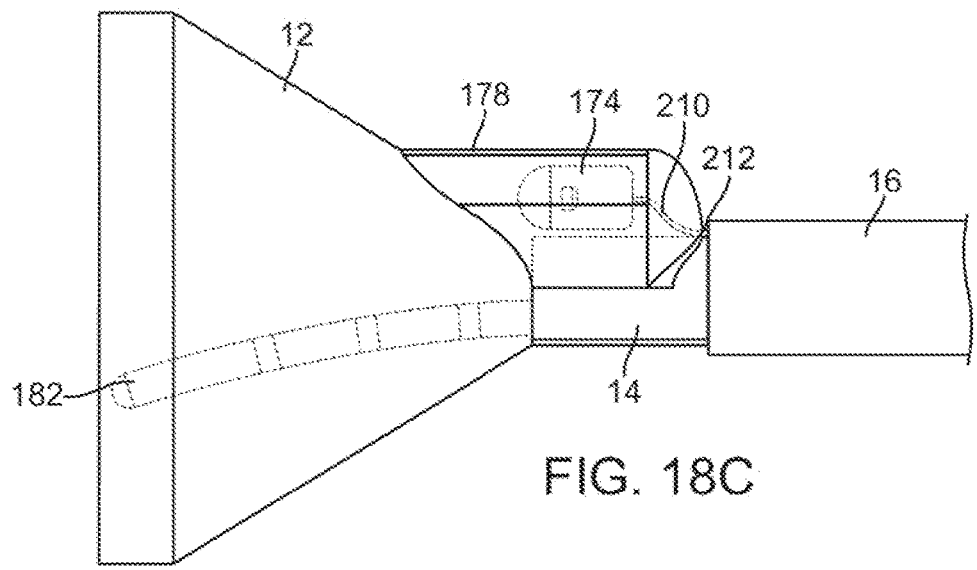
FIGS. 18C and 18D show side and perspective views of the imaging element urged into its off-axis configuration when pulled proximally through the hood and into the receiving channel or pocket.
Figure 18D:
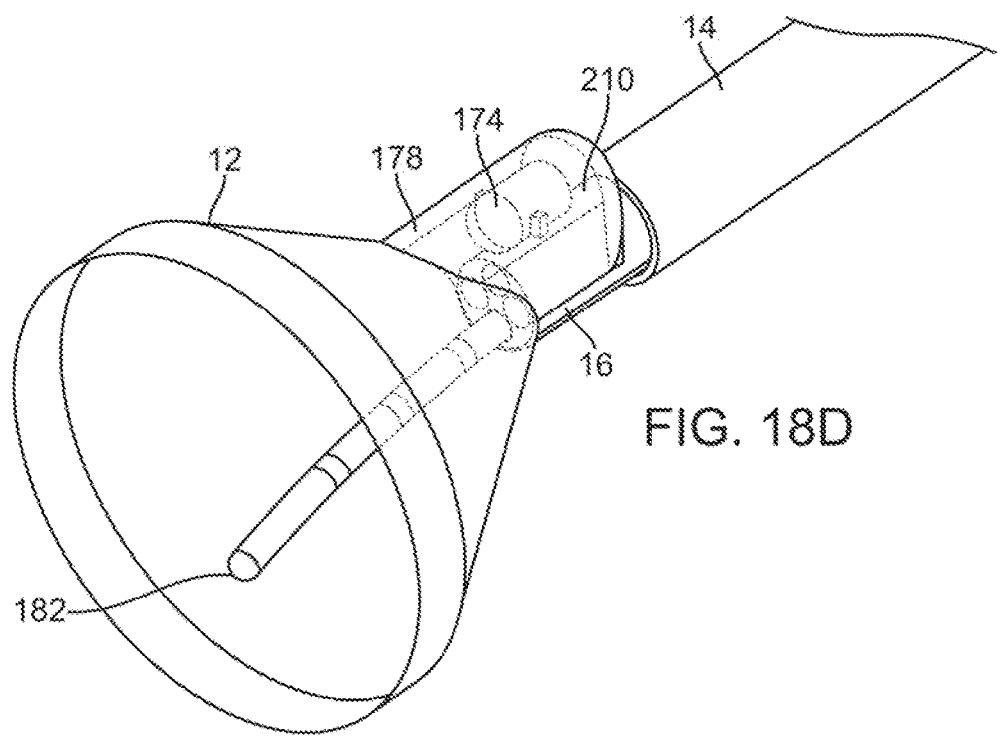

Another variation is illustrated in the side views of FIGS. 18A and 18B which show imaging element 174 attached to imager support member 210. In its low-profile configuration and its initial deployed configuration, imaging element 174 may be positioned distal to hood 12 while connected via support member 210 to allow for sheath 14 to accommodate relatively larger sized imaging elements. Support member 210 may pass proximally through side opening 212 defined along a side surface of catheter 16 adjacent to where receiving channel or pocket 178 is located. Thus, once hood 12 has been expanded, support member 210 may be pulled proximally through opening 212 to draw imaging element 174 proximally directly into receiving channel or pocket 178 such that imaging element 174 is positioned into its off-axis location, as shown in the side and perspective views of FIGS. 18C and 18D. With imaging element 174 and support member 210 withdrawn, any number of instruments such as ablation probe 182 may be advanced into hood 12 to treat the underlying tissue in an unobstructed field.

Figure 19A:
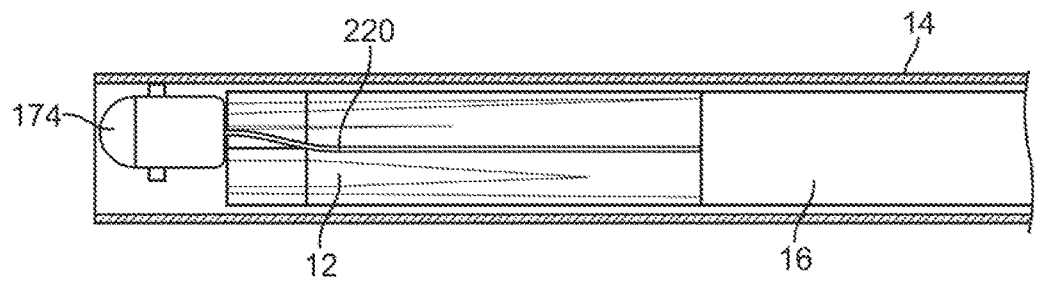
FIGS. 19A and 19B show side views of another variation of the tissue visualization catheter with an imaging element positioned distal to the collapsed hood within a sheath via an imager support member comprised of a shape memory alloy and in a deployed configuration where the support member articulates into an off-axis configuration.
Figure 19B:
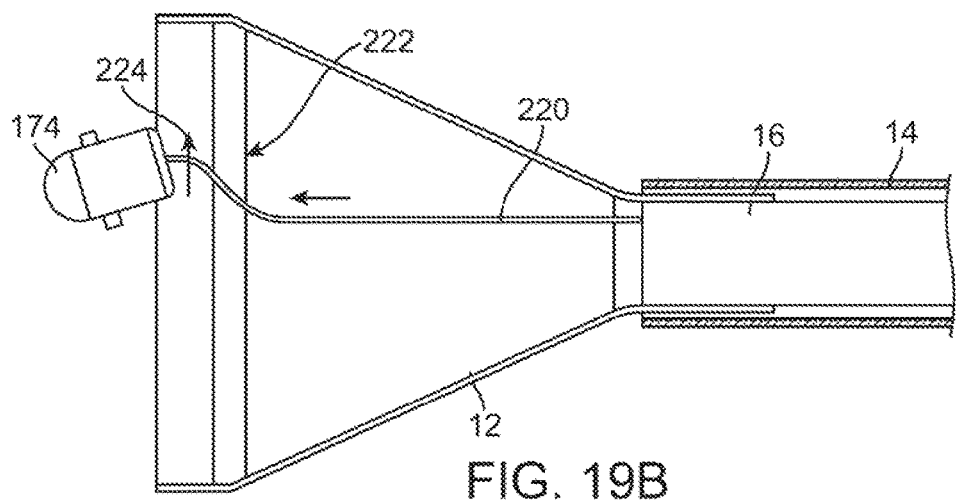
Figure 19C:
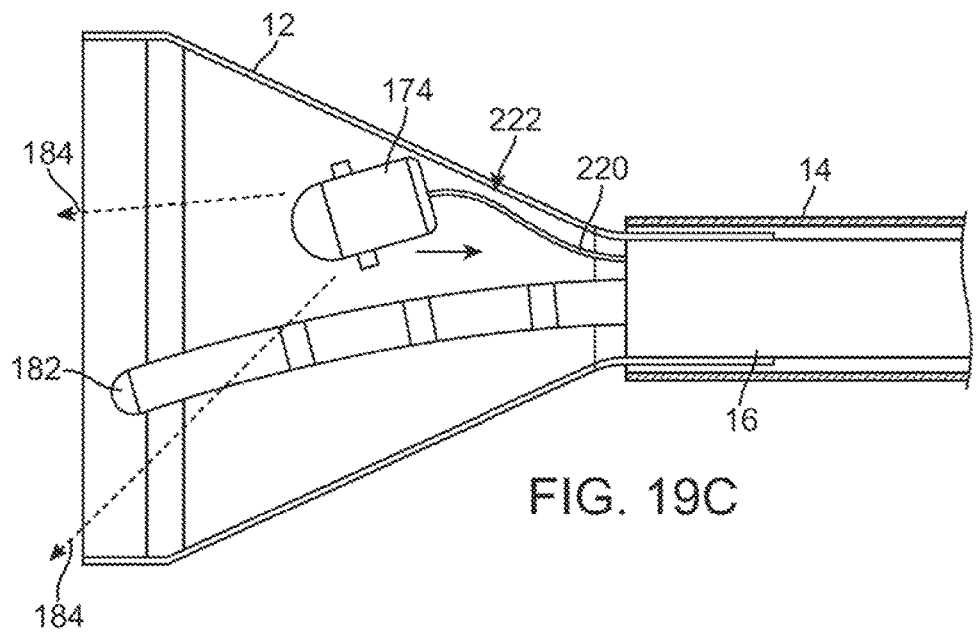
FIGS. 19C and 19D show partial cross-sectional side and perspective views, respectively, of the imaging element pulled proximally into the hood in its off-axis configuration.
Figure 19D:
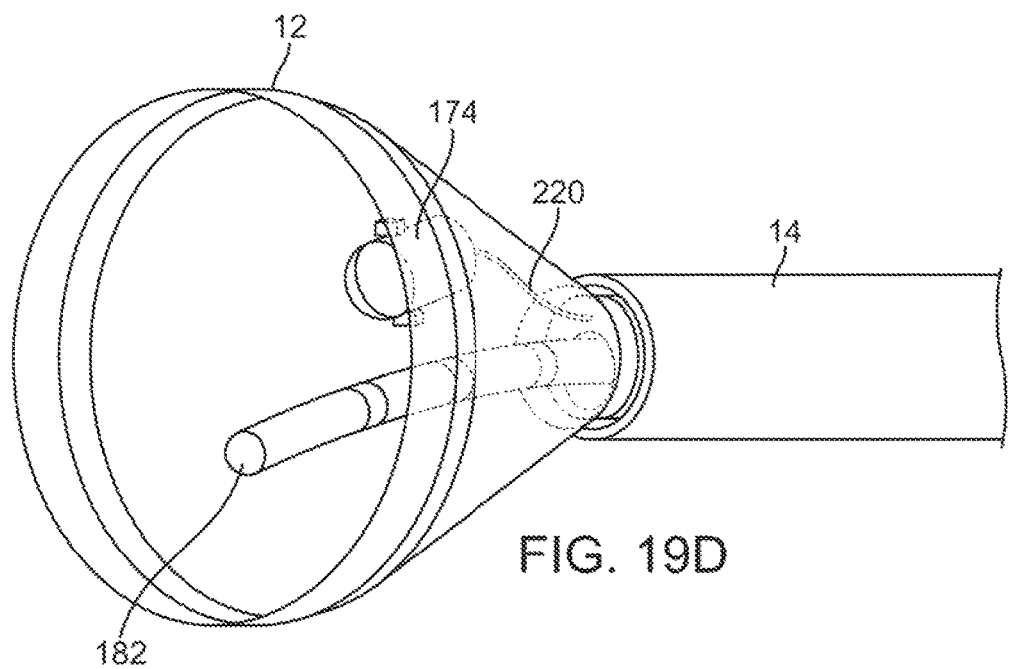

FIGS. 19A and 19B illustrate yet another variation where imaging element 174 may be positioned upon an imager support member 220 fabricated from a shape memory alloy, e.g., Nitinol, which is pre-shaped with an angled or off-axis segment 222 to position imaging element 174 into an off-axis position when freed from the constraints of sheath 14. FIG. 19A illustrates imaging element 174 positioned distally of the collapsed hood 12 with the support member 220 extended forward. Alignment of imaging element 174 in this manner allows for hood 12 to be collapsed completely and thus frees up additional space within the lumen of sheath 14. As hood 12 is expanded, angled or off-axis segment 222 may reconfigure into its relaxed shape where imaging element 174 is moved into its off-axis configuration, as indicated by the direction of movement 224 in FIG. 19B. Support member 220 may then be pulled proximally into hood 12 such that imaging element 174 is positioned along an inner surface of hood 12 in an off-axis configuration, as illustrated in the partial cross-sectional side and perspective views of FIGS. 19C and 19D. To withdraw imaging element 174, support member 220 may be advanced distally of hood 12, which may be collapsed proximally of imaging element 174 and both hood 12 and imaging element 174 may be pulled proximally into sheath 14, which may constrain angled or off-axis segment 222 back into its low-profile configuration.

Figure 20:
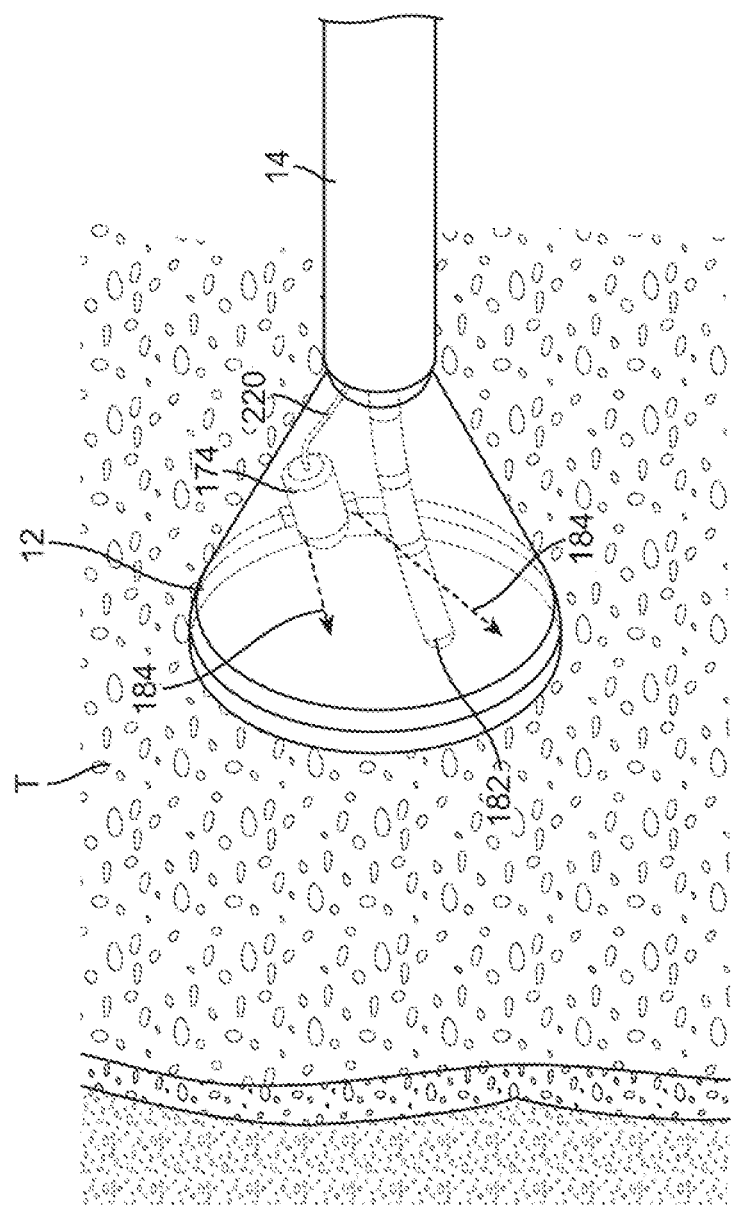
FIG. 20 shows a perspective view of the visualization catheter placed against a tissue surface for affecting a therapeutic procedure under off-axis visualization.

FIG. 20 illustrates a perspective view of deployed hood 12 positioned upon a tissue region of interest T with imaging element 174 positioned into its off-axis configuration via support member 220.

Figure 21A:
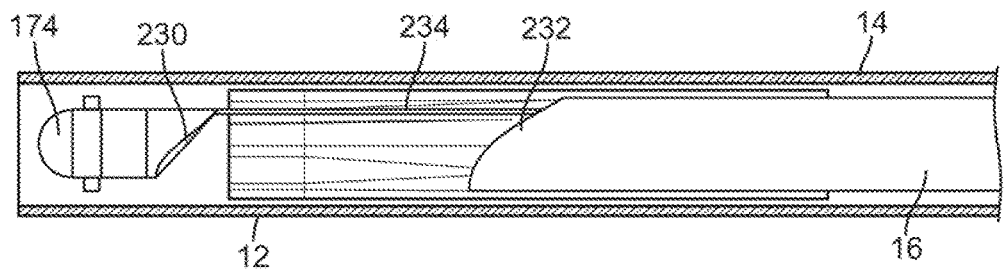
FIGS. 21A and 21B show partial cross-sectional side views of the visualization catheter with the imaging element disposed distally of the collapsed hood and pulled proximally against a tapered interface within the deployed hood.
Figure 21B:
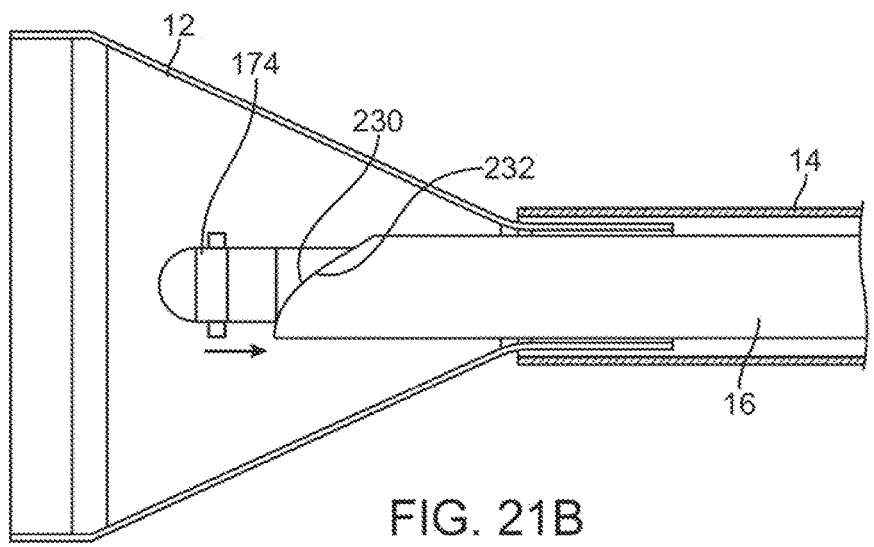

Yet another variation is illustrated in the partial cross-sectional side views of FIGS. 21A and 21B which illustrate imaging element 174 which is attached to imager support member 234 and positioned distal to collapsed hood 12. The proximal surface of imaging element 174 may have an angled or tapered surface 230 which extends at a first angle relative to deployment catheter 16. The distal end of catheter 16 may also define a receiving surface 232 which is angled or tapered at an angle complementary to surface 230. With hood 12 in its expanded configuration, support member 234 may be pulled proximally such that tapered surface 230 of imaging element 174 is drawn into contact against receiving surface 232, as illustrated in FIG. 21B.

Figure 21C:
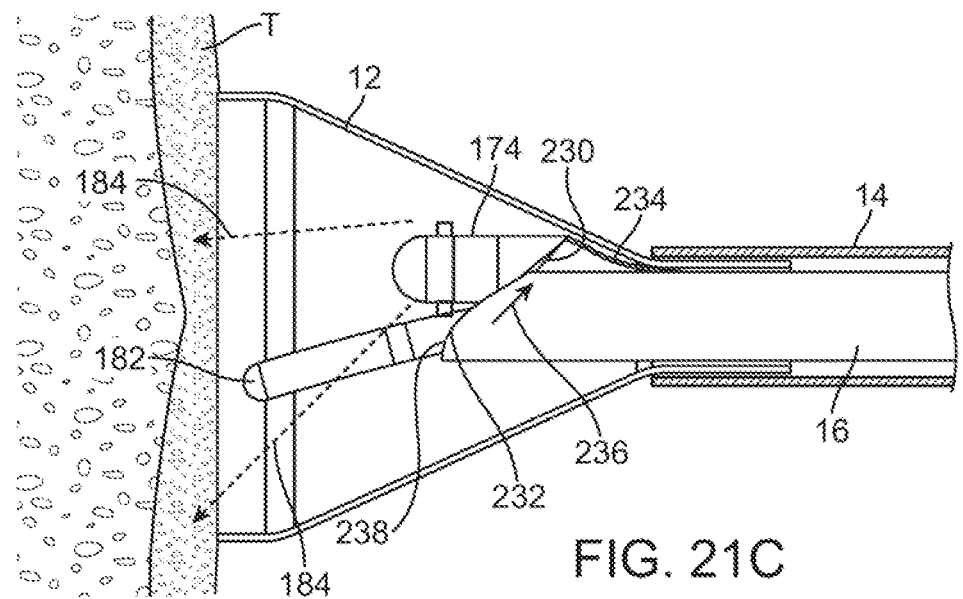
FIGS. 21C and 21D show side and perspective views, respectively, of the deployed hood and imaging element actuated into its off-axis configuration by the angled interface between the imaging element housing and distal end of the internal deployment catheter.
Figure 21D:
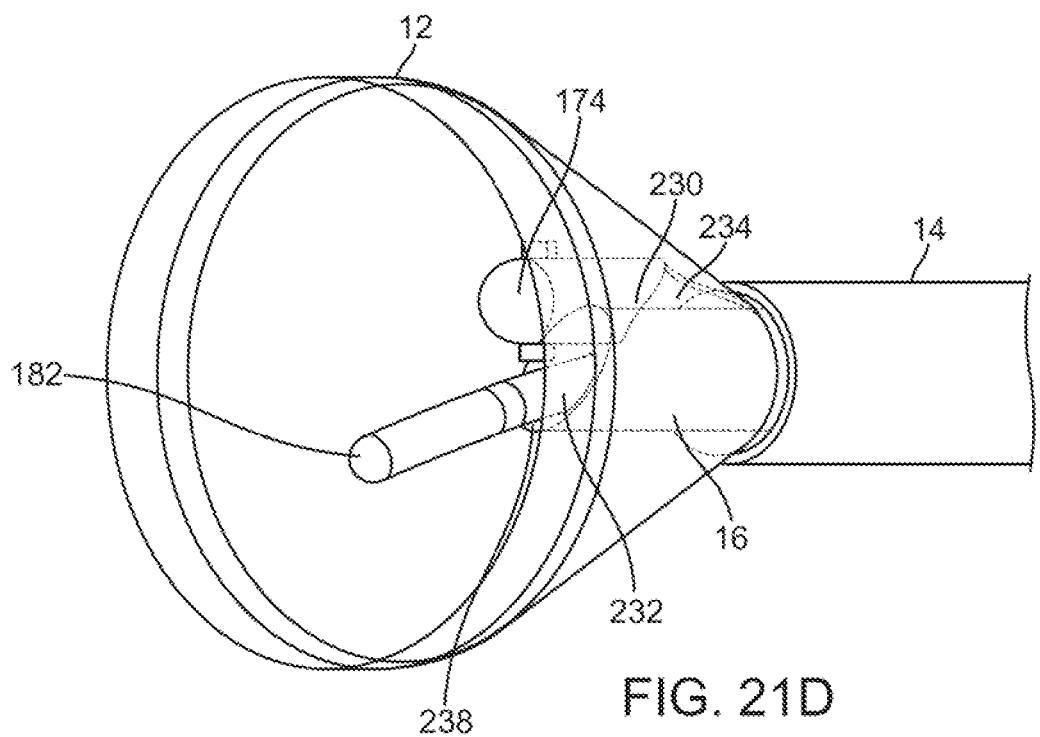
Figure 22:
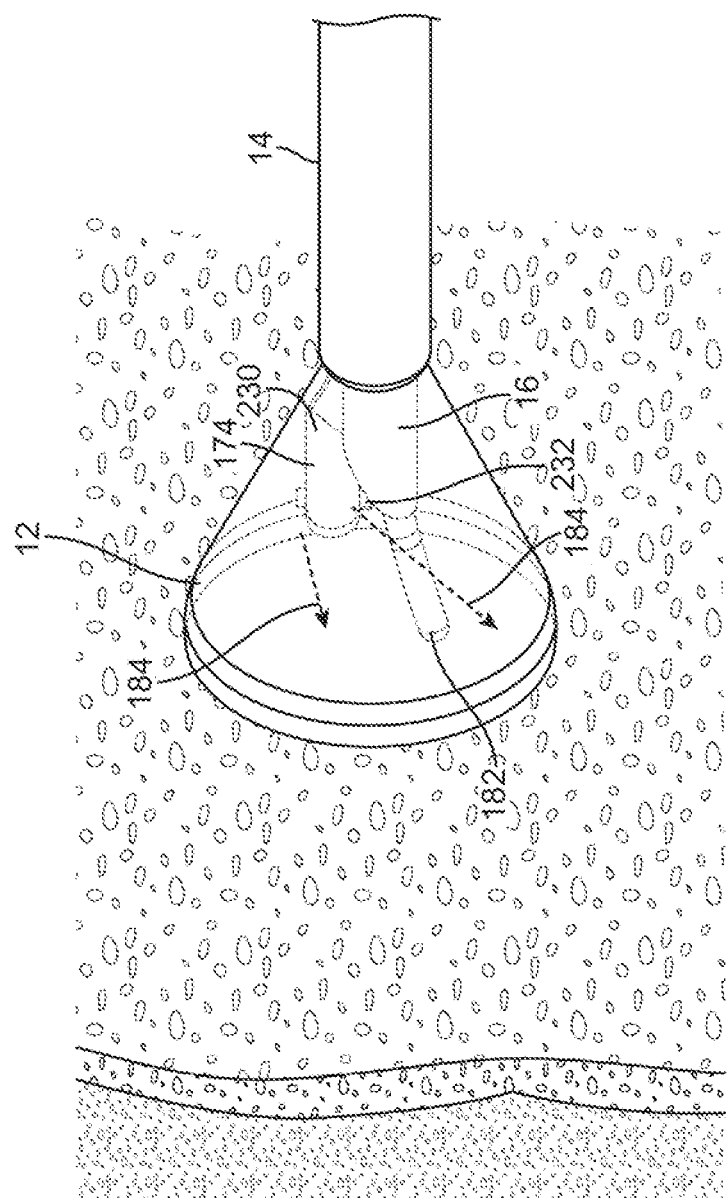
FIG. 22 shows a perspective view of the visualization catheter placed against a tissue surface with the off-axis camera providing an elevated off-axis image to better estimate tool movements during therapeutic procedures.

Upon further tensioning of support member 234, imaging element 174 may be forced to slide proximally along the tapered interface and into its off-axis location, as indicated by the angled direction of travel 236 in the cross-sectional side view of FIG. 21C. By moving the imaging element 174 off-axis, the area in front of the working lumen 238 of deployment catheter 16 is cleared for any number of instruments, such as ablation probe 182, to be deployed through as illustrated in the perspective view of FIG. 21D. FIG. 22 illustrates the imaging element 174 angled into its off-axis position via the tapered or angled interface between tapered surface 230 of imaging element 174 and receiving surface 232 while visualizing the underlying tissue to be treated via ablation probe 182.

Figure 23A:
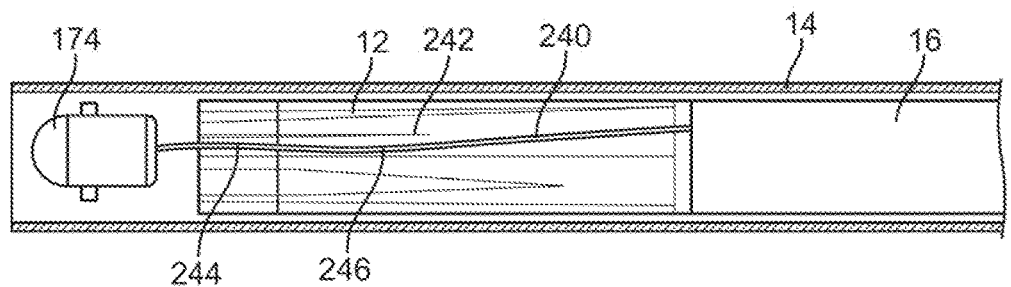
FIGS. 23A and 23B show partial cross-sectional side views of an imaging element attached to a hinged cantilever member and disposed distally of a collapsed hood and the deployed hood.
Figure 23B:
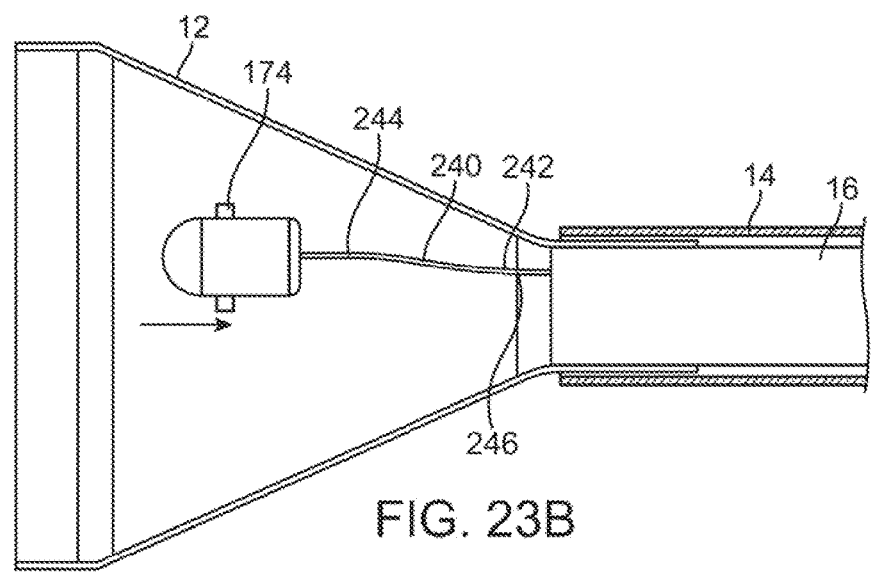
Figure 24A:
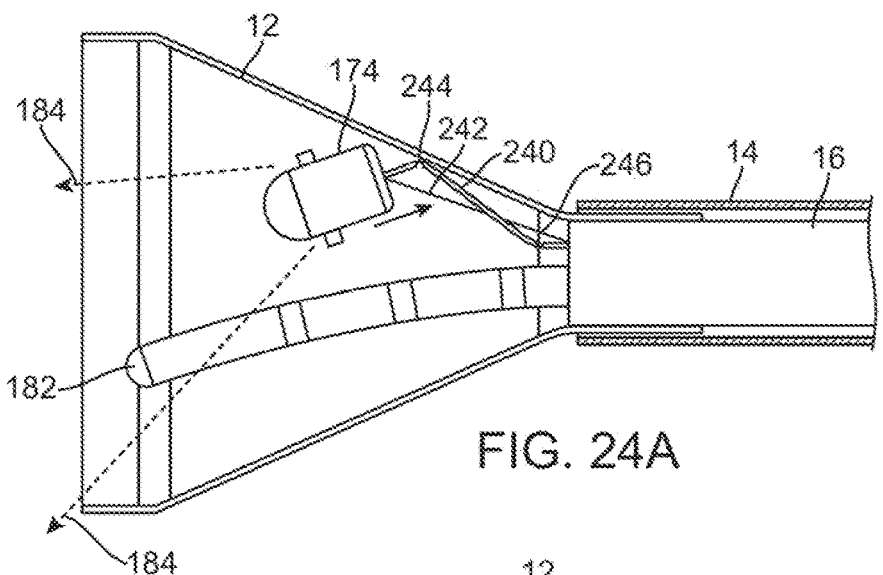
FIGS. 24A to 24C show side, detailed side, and perspective views, respectively, where the imaging element is positioned in an off-axis configuration by the hinged cantilever member actuated via a pullwire.
Figure 24B:
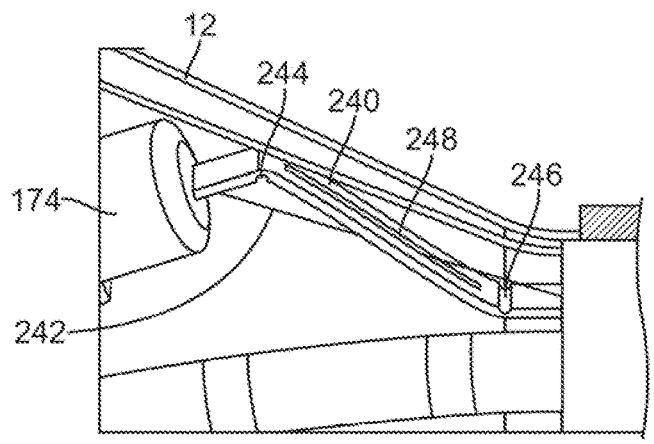
Figure 24C:
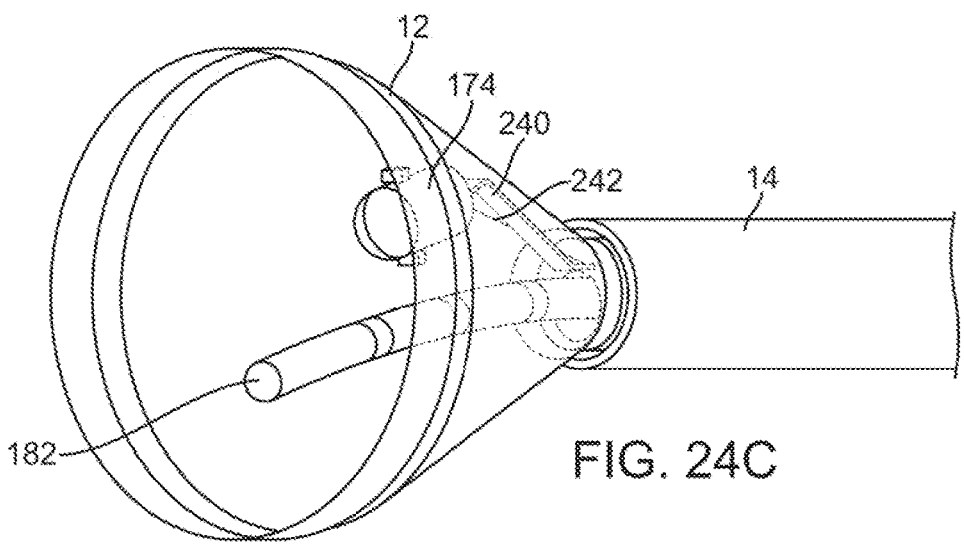

FIGS. 23A and 23B show yet another variation where imaging element 174 may be positioned distal to collapsed hood 12 while attached to a cantilevered support member 240. FIG. 23B shows how imaging element 174 may be withdrawn proximally into hood 12 from its distal position once hood 12 has been expanded. Once imaging element 174 has been sufficiently withdrawn, a pullwire 242 made from a material such as Nitinol, stainless steel, titanium, etc. and attached to imaging element 174 and passing through an opening or slot 248 defined through support member 240 may be tensioned through deployment catheter 16, as shown in the detailed perspective view of FIG. 24B. Cantilevered support member 240 may define a first notch or hinge 244, e.g., a living hinge, along a first side of member 240 and a second notch or hinge 246, e.g., also a living hinge, along a second side of member 240 along an opposite side to where first notch or groove 244 is defined and proximal to first notch or groove 244, as shown in FIG. 24A. Thus, when pullwire 242 is tensioned to pull imaging element 174 proximally, cantilevered support member 240 may be forced to reconfigure from its straightened configuration such that member 240 bends at notches 244, 246 into an angled configuration to reposition imaging element 174 into its off-axis position, as shown in the side and perspective views of FIGS. 24A and 24C. Upon relaxing pullwire 242, support member 240 may reconfigure back into its straightened low-profile shape.

FIG. 25 illustrates a perspective view of deployed hood 12 positioned upon a tissue region of interest T with imaging element 174 positioned into its off-axis configuration via cantilevered support member 240 with pullwire 242 under tension.

Figure 26A:
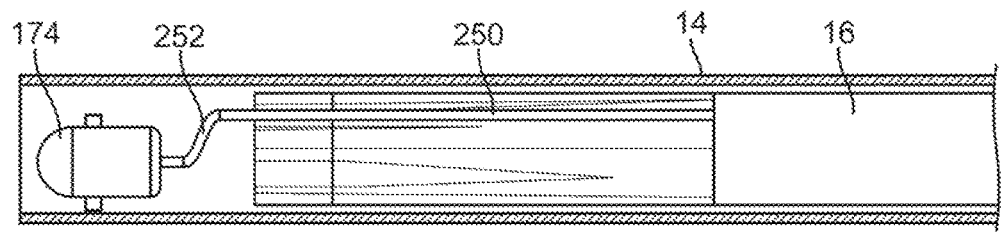
FIGS. 26A and 26B show partial cross-sectional side views of the visualization catheter with the imaging element disposed distally of the collapsed hood and being rotated into its off-axis configuration via its rotatable imager support member.
Figure 26B:
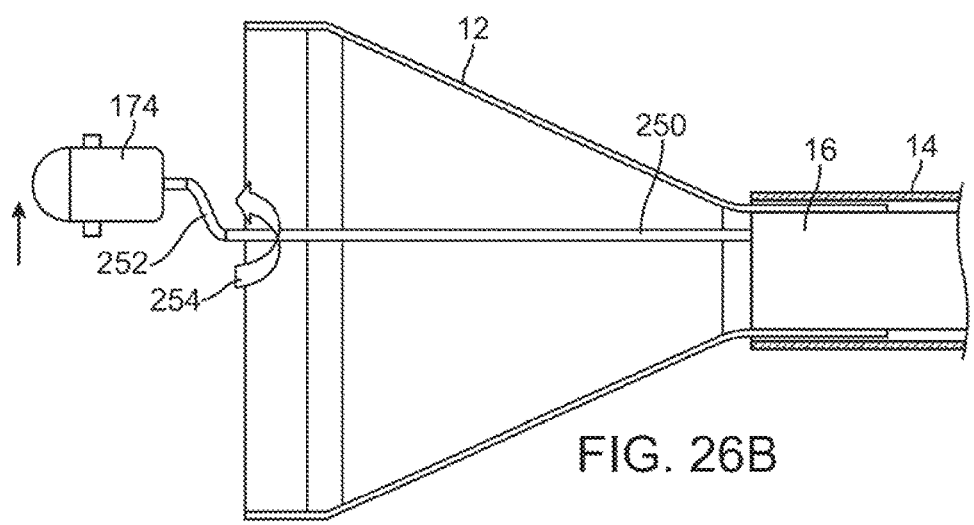

In yet another variation, FIGS. 26A and 26B illustrate partial cross-sectional side views of an imaging element 174 positioned distal to the collapsed hood 12 in a low-profile configuration shown in FIG. 26A where imaging element 174 is attached to imager support member 250 which is rotatable about its longitudinal axis. A distal portion of support member 250 may define a curved off-axis section 252 which aligns imaging element 174 eccentrically relative to catheter 16 such that when support member 250 is rotated, e.g., 180 degrees, imaging element 174 is rotated into an off-axis position, as indicated by the direction of rotation 254 illustrated in FIG. 26B. Off-axis section 252 of support member 250 may be angled along its length at two or more locations and it may be fabricated from any number of materials, such as Nitinol, stainless steel, titanium, etc.

Figure 27A:
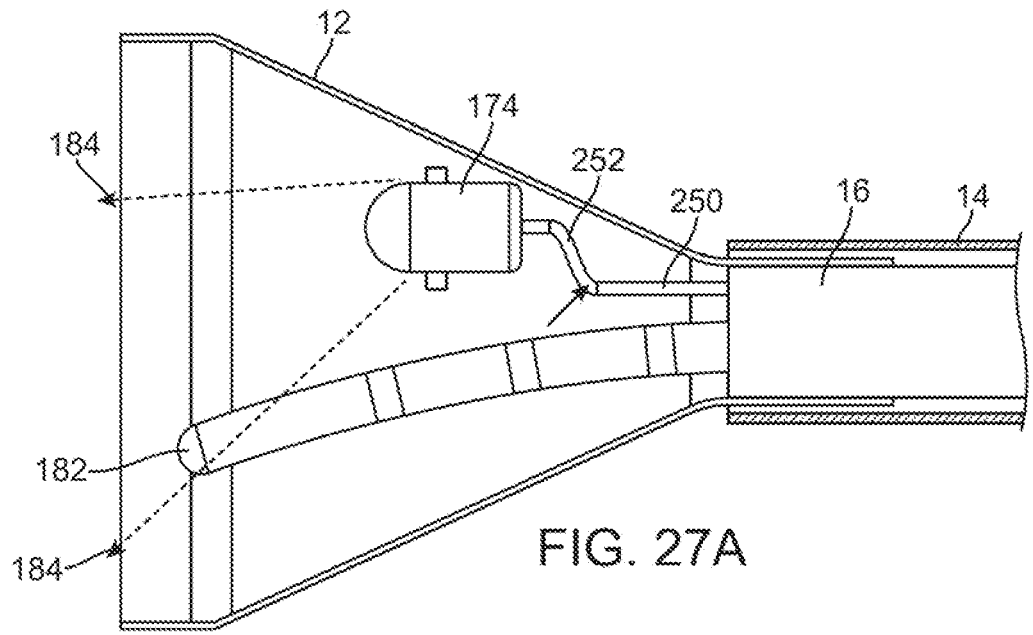
FIGS. 27A and 27B show side and perspective views, respectively, where the imaging element is positioned in an off-axis configuration by the rotated support member.
Figure 27B:
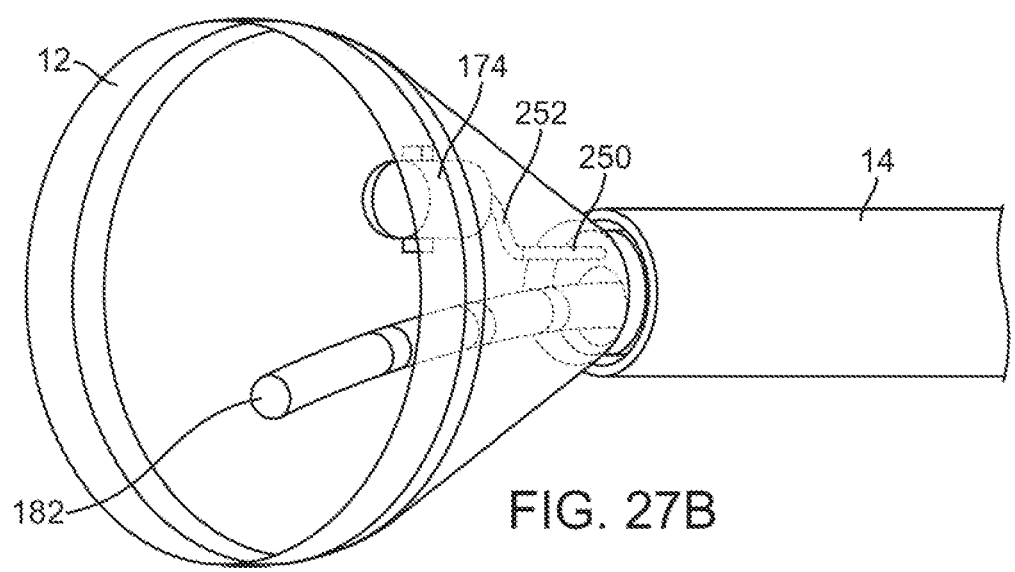

FIGS. 27A and 27B show side and perspective views of imaging element 174 having been rotated into its off-axis position with support member 250 withdrawn proximally into hood 12 such that imaging element 174 is positioned along an inner surface of hood 12. With the space distal to deployment catheter 16 unobstructed by imaging element 174, any number of instruments may be advanced into hood 12, such as ablation probe 182, to be utilized upon the underlying tissue while visualized via imaging element 174.

Figure 28:
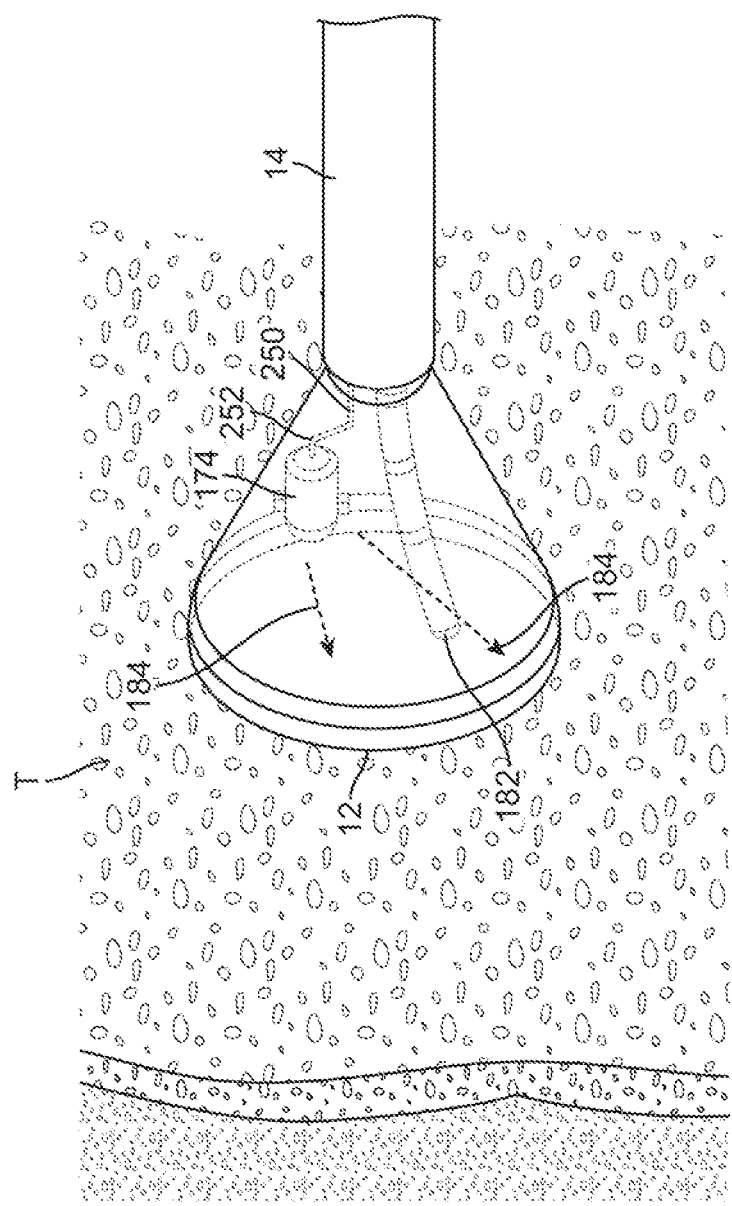
FIG. 28 shows a perspective view of the visualization catheter placed against a tissue surface with the imaging element providing an elevated off-axis image to better estimate tool movement during therapeutic procedures.

FIG. 28 illustrates a perspective view of deployed hood 12 positioned upon a tissue region of interest T with imaging element 174 positioned into its off-axis configuration via angled support member 250 imaging the underlying tissue within the open area of hood 12 through a transparent fluid while also treating the tissue with ablation probe 182.

Figure 29A:
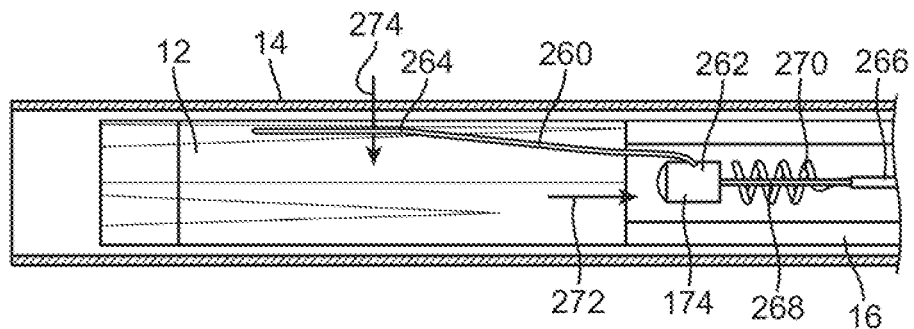
FIGS. 29A and 29B show partial cross-sectional side views of another variation of the visualization catheter where the imaging element may be attached to the hood via an elastic member such that retraction of the imaging element facilitates collapse of the hood and withdrawal of the imaging element facilitates deployment of the hood.
Figure 29B:
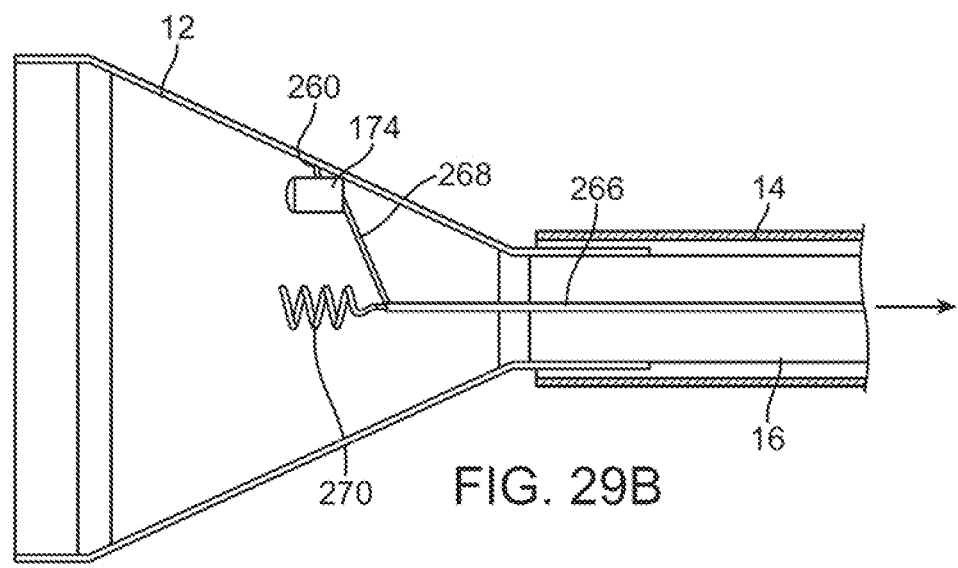

Another variation is illustrated in the partial cross-sectional side views of FIGS. 29A and 29B which show imaging element 174 coupled to the distal end of shaft 266, which may optionally also include an instrument 270 positioned upon its distal end, such as a helical tissue grasper, ablation probe, needle, or other instrument. Imaging element 174 may be coupled to the distal end of shaft 266 via linkage member 268 which is free to pivot relative to both imaging element 174 and shaft 266, e.g., via living hinges, pivots, etc. An elastic member 260 (e.g., silicone rubber, latex, polyurethane, or other common elastomers) may also couple imaging element 174 at attachment point 262 to the inner surface of hood 12 at attachment point 264. By pulling proximally on shaft 266 through catheter 16, as indicated by the direction of imager retraction 272, linkage member 268 may pull imaging element 174 proximally into a work channel of catheter 16. This may subsequently stretch elastic member 260 connecting imaging element 174 and hood 12 resulting in elastic member 260 pulling hood 12 into its low-profile collapsed configuration before or while hood 12 is retracted into sheath 14, as indicated by the direction of hood collapse 274. Hence imaging element 174 may be positioned proximal to and in line with hood 12, by positioning it within a working lumen rather than wrapped within the collapsed hood 12 when retracted into sheath 14.

To deploy hood 12, the process may be reversed where shaft 266 may be urged distally to push linkage member 268, which in turn may push imaging element 174 distally. As hood 12 is deployed, elastic member 260 may pull imaging element into its off-axis position along the inner surface of hood 12.

Figure 30A:
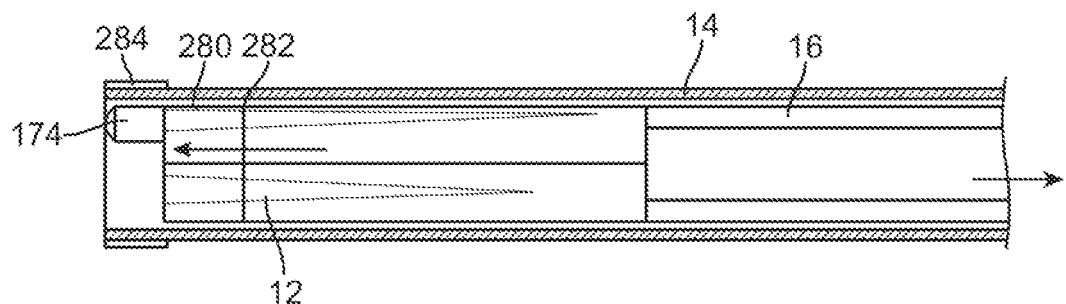
FIGS. 30A and 30B show partial cross-sectional side views of another variation of the tissue visualization catheter where the imaging element is translatably coupled or attached along a strut of the hood.
Figure 30B:
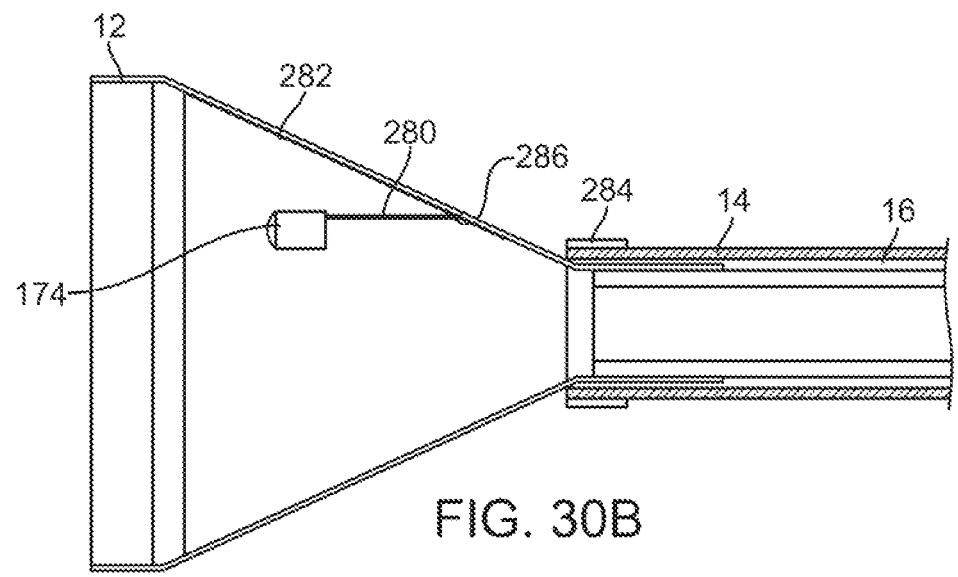

FIGS. 30A and 30B illustrate yet another variation in the partial cross-sectional side views where imaging element 174 is attached to linkage member 280, which is also slidingly connected to strut 282, which in turn is positioned along an inner surface of hood 12. When hood 12 is in its collapsed configuration, imaging element 174 may be positioned distal to hood 12 via linkage member 280, as shown in FIG. 30A. A magnet 284 (e.g., ferrous magnet or electromagnet) may be positioned along or at the distal end of sheath 14 such that magnet 284 is integrated with sheath 14 or placed along an outer or inner surface of sheath 14. The housing of imaging element 174 may be fabricated from a magnetically attractive and/or ferromagnetic material such that when hood 12 is deployed distally from sheath 14, the magnetic attraction between the housing of imaging element 174 and magnet 284 may magnetically pull imaging element 174. As hood 12 is deployed from sheath 14, imaging element 174 may slide or roll proximally along strut 282, which may be connected to one another via a translatable coupling 286, until imaging element 174 is slid to a proximal position along strut 282, as shown in FIG. 30B. In this proximal position, imaging element 174 may be positioned in its off-axis configuration relative to catheter 16 and hood 12.

When hood 12 is retracted into sheath 14, magnet 284 may magnetically attract imaging element 174 such that hood 12 is collapsed proximally of imaging element 174 and is positioned distally of the collapsed hood 12 when retained within sheath 14, thus freeing up additional space within sheath 14.

Figure 31A:
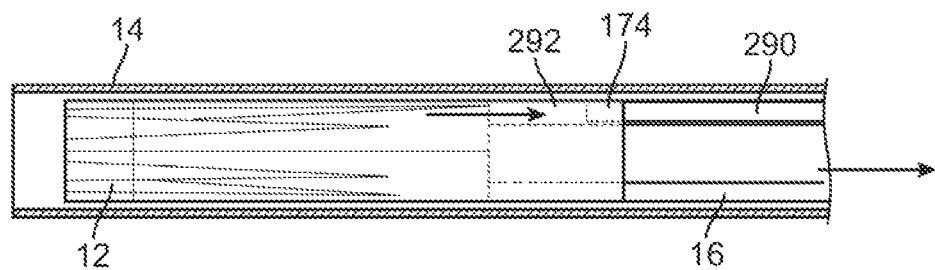
FIGS. 31A and 31B show a partial cross-sectional side view of another variation of the tissue visualization catheter where the imaging element may be attached upon a distal end of one or more inflatable balloons which may be inflated to position the imaging element along the hood.
Figure 31B:
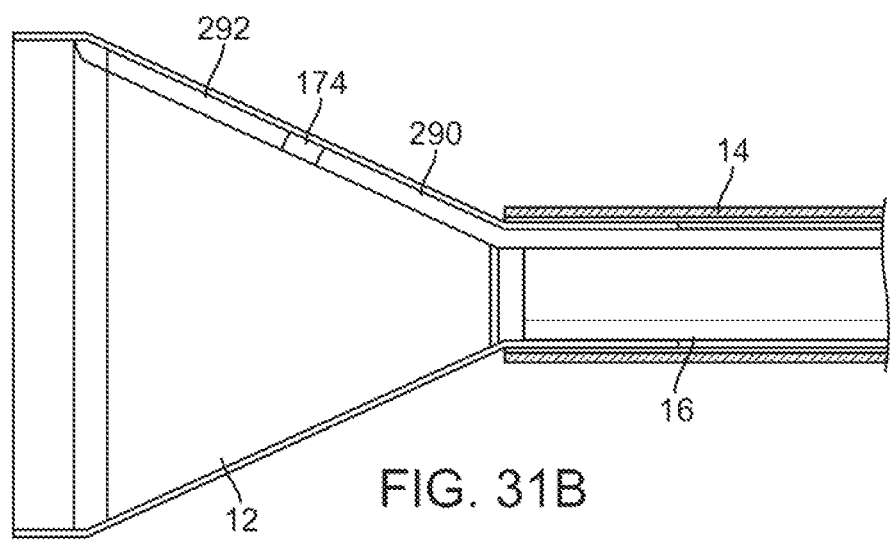

FIGS. 31A and 31B illustrate partial cross-sectional side views of another variation where hood 12 may define an elongate channel 292 within or along the length of hood 12. Once hood 12 has been deployed from sheath 14 into its expanded configuration, an elongate balloon 290 having imaging element 174 attached to its distal end may be inflated within channel 292 such that balloon 290 propagates distally and advances imaging element 174 into the hood 12, as shown in FIG. 31B. Balloon 290 may be fabricated from various elastomeric materials such as C-flex, ChronoPrene, silicone or polyurethene, etc. Moreover, channel 292 may be constructed by enclosing the balloon 290 between two layers of heat welded material, e.g., Mylar or PET sheets, such that the welded sheets form a cylindrical lumen through which balloon 290 may expand along the axis of channel 292 when inflated. The assembly of balloon 290, imaging element 174, and channel 292 may then be mounted on the inner wall of hood 12, e.g., by an adhesive.

Figure 32A:
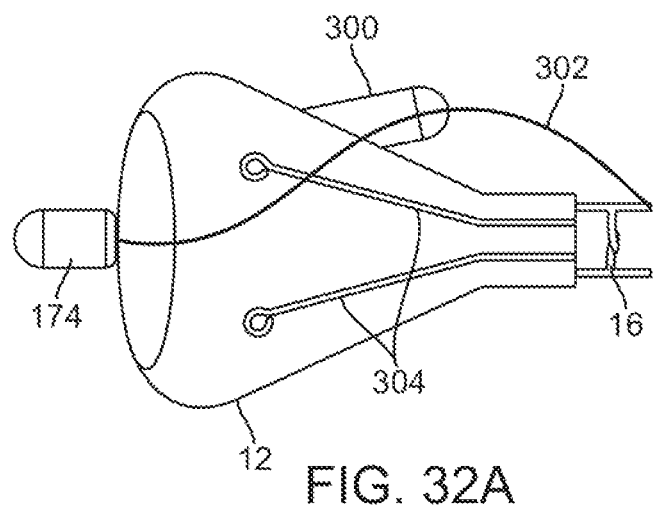
FIGS. 32A and 32B show side views of another variation of an imaging hood having an expandable channel or pocket positioned along the hood for accommodating the imaging element.
Figure 32B:
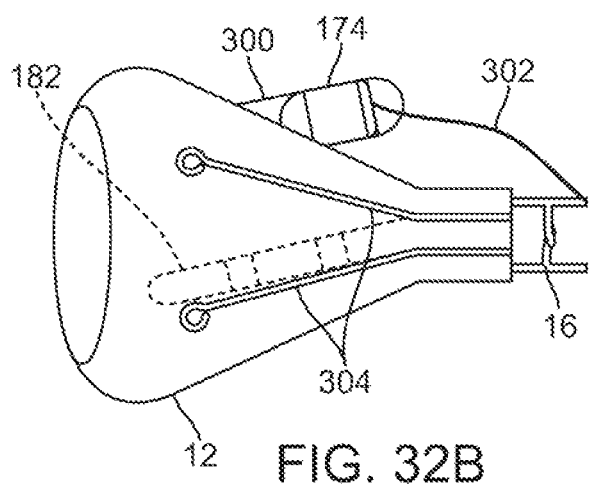

FIGS. 32A and 32B show side views, respectively, of another variation of imaging hood 12 modified to have an expandable channel or pocket 300 positioned along hood 12. In this configuration, one or more hood support struts or members 304 may be positioned along hood 12 to provide structural support. When imaging element 174 and hood 12 are collapsed in their low-profile configuration, imaging element 174 may be positioned distal to hood 12 with control member 302, e.g., cables, wires, etc., connected to imaging element 174 and passing through channel or pocket 300. With imaging element 174 positioned distal to expanded hood 12, as shown in FIG. 32A, imaging element 174 may be pulled proximally via member 302 into channel or pocket 300 such that the imager 174 slides and squeezes itself into pocket 300, which itself may bulge out laterally to the side of hood 12, as shown in FIG. 32B. With the camera positioned laterally of hood 12 when deployed, a clear field of visualization is provided.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A system for visualizing a tissue region of interest, comprising:
    a deployment catheter defining at least one lumen therethrough;
    a hood projecting distally from the deployment catheter and defining an open area therein, wherein the open area is in direct fluid communication with the at least one lumen;
    an elongate channel directly coupled to the hood such that the elongate channel terminates distally into the open area, the elongate channel extending proximally from an outer surface of the hood and bounded proximally at a proximal pocket surface;
    an imaging element for visualizing tissue adjacent to the open area, the imaging element sized to pass into the elongated channel at a distal end of the elongate channel, wherein proximal movement within the elongated channel is restricted by the proximal pocket surface; and
    a control member extending within the elongate channel and through the proximal pocket surface for moving the imaging element through the elongate channel.

2. The system of claim 1 further comprising a sheath slidably disposed over the deployment catheter.

3. The system of claim 1 wherein the deployment catheter has an elongated axis and wherein the elongate channel has a channel axis extending away from the elongated axis of the deployment catheter.

4. The system of claim 1 further comprising an ablation probe passing through the deployment catheter.

5. The system of claim 1 wherein the deployment catheter is steerable.

6. The system of claim 1 wherein the hood is comprised of a compliant material.

7. The system of claim 1 hood comprises a frame of superelastic or shape memory alloy.

8. The system of claim 1 wherein the hood is conically shaped.

9. The system of claim 1 wherein the hood comprises at least one support member.

10. The system of claim 1 wherein the imaging element comprises at least one optical fiber, CCD imager, or CMOS imager.

* * * * *